US008802921B2

(12) United States Patent
Ainley et al.

(10) Patent No.: US 8,802,921 B2
(45) Date of Patent: Aug. 12, 2014

(54) ENGINEERED LANDING PADS FOR GENE TARGETING IN PLANTS

(75) Inventors: William M. Ainley, Carmel, IN (US);
Ryan C. Blue, Fishers, IN (US);
Michael G. Murray, Rio Rancho, NM (US); David Corbin, Carmel, IN (US);
Rebecca R. Miles, Pendleton, IN (US);
Steven R. Webb, Westfield, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 659 days.

(21) Appl. No.: 13/011,735

(22) Filed: Jan. 21, 2011

(65) Prior Publication Data

US 2011/0191899 A1    Aug. 4, 2011

Related U.S. Application Data

(60) Provisional application No. 61/297,641, filed on Jan. 22, 2010.

(51) Int. Cl.
| | | |
|---|---|---|
| *C12N 15/87* | (2006.01) | |
| *C12N 15/82* | (2006.01) | |
| *C12N 15/05* | (2006.01) | |
| *C12N 5/04* | (2006.01) | |
| *C12N 5/10* | (2006.01) | |
| *C07H 21/04* | (2006.01) | |
| *A01H 5/10* | (2006.01) | |
| *A01H 5/00* | (2006.01) | |

(52) U.S. Cl.
USPC ........ 800/278; 800/295; 435/320.1; 435/419; 435/430; 435/468; 536/23.2; 536/24.1

(58) Field of Classification Search
None
See application file for complete search history.

(56) References Cited

U.S. PATENT DOCUMENTS

| | | | |
|---|---|---|---|
| 5,641,876 A | 6/1997 | McElroy et al. | |
| 6,384,207 B1 | 5/2002 | Ainley et al. | |
| 7,348,179 B2 | 3/2008 | Gleba et al. | |
| 7,625,755 B2 | 12/2009 | Askew et al. | |
| 2007/0134796 A1 | 6/2007 | Holmes et al. | |
| 2009/0093366 A1 | 4/2009 | Wright et al. | |

FOREIGN PATENT DOCUMENTS

| | | |
|---|---|---|
| WO | WO94/00977 | 1/1994 |
| WO | WO95/06722 | 3/1995 |
| WO | WO2005/107437 | 11/2005 |
| WO | WO2008/141154 | 11/2008 |
| WO | 2011082310 A2 | 7/2011 |

OTHER PUBLICATIONS

Cai et al 2009 Plant Molecular Biology 69: p. 699-709.*
Puchta et al 1996 PNAS 93: p. 5055-5060.*
Shetty et al 2008 Journal of Biological Engineering 2:5 p. 1-12.*
Moon et al Oct. 2009 Trends in Biotechnology 28:1 p. 3-8.*
European Search Report dated May 24, 2013, for Application No. 11735271.6, (5 pages).
Supplementary European Search Report dated May 15, 2013, for Application No. EP 11 73 5271, (3 pages).
Cai, C., et al., "Targeted transgene integration in plant cells using designed zinc finger nucleases," Plant Molecular Biology, vol. 69, Dec. 27, 2008, pp. 699-709.
D'Halluin, K., et al., "Homologous recombination: a basis for targeted genome optimization in crop species such as maize," Plant Biotechnology Journal, vol. 6, No. 1, Jan. 1, 2008, pp. 93-102.
Puchta, H., et al., "Homologous Recombination in Plant Cells is Enhanced by in Vivo Induction of Double Strand Breaks into DNA by Site-Specific Endonuclease," Nucleic Acids Research, vol. 21, No. 22, Nov. 11, 1993, pp. 5034-5040.
Salomon, S., et al., "Capture of genomic and T-DNA sequences during double-strand break repair in somatic plant cells," Embo Journal, vol. 17, No. 20, Oct. 15, 1998, pp. 6086-6095.
Siebert, R., et al., "Efficient Repair of Genomic Double-Strand Breaks by Homologous Recombination between Directly Repeated Sequences in the Plant Genome," The Plant Cell, vol. 14, May 1, 2002, pp. 1121-1131.
Srivastava, V., et al., "Biolistic mediated site-specific integration in rice," Molecular Breeding: New Strategies in Plant Improvement, vol. 8, No. 4, Jan. 1, 2001, pp. 345-350.
Srivastava, V., et al., "Site-specific gene integration technologies for crop improvement," In Vitro Cellular & Developmental Biology—Plant, vol. 46, No. 3, Jun. 1, 2010, pp. 219-232.
Kandavelou, Karthikeyan et al., "Targeted manipulation of mammalian genomes using designed zinc finger nucleases", Biochemical and Biophysical Research Communications, 2009, pp. 56-61, vol. 388.
Tovkach, Andriy et al., "A toolbox and procedural notes for characterizing novel zinc finger nucleases for genome editing in plant cells",The Plant Journal, 2009, pp. 747-757, vol. 57.
Townsend, Jeffrey A. et al., "High-frequency modification of plant genes using engineered zinc-finger nucleases", Nature, May 21, 2009, pp. 442-446, vol. 459.
Wu et al, "Custom-designed zinc finger nucleases: what is next," Cell. Mol. Life Sci. 2007, pp. 2933-2944, vol. 64.
International Search Report for International Application No. PCT/US2011/022145, mailed Sep. 28, 2011.
Written Opinion for International Application No. PCT/US2011/022145, mailed Sep. 28, 2011.

* cited by examiner

*Primary Examiner* — David T Fox
*Assistant Examiner* — Matthew Keogh
(74) *Attorney, Agent, or Firm* — James Daly; TraskBritt, P.C.

(57) ABSTRACT

A method for producing a transgenic plant includes providing a nucleic acid molecule comprising at least two regions of nucleic acid sequence that lack sequence homology with genomic DNA of the plant cell, and at least two zinc finger nuclease recognition sites, wherein the at least two regions of nucleic acid sequence that lack sequence homology with genomic DNA of the plant cell flank the at least two zinc finger nuclease recognition sites. A plant cell or tissue having the nucleic acid molecule stably integrated into the genome of the plant cell is transformed. A plant is regenerated from the plant cell. Transgenic plants are produced by the method. Seeds are produced by the transgenic plants.

20 Claims, 25 Drawing Sheets

SEQUENCE LISTING

```
<160> NUMBER OF SEQ ID NOS: 38

<210> SEQ ID NO 1
<211> LENGTH: 1000
<212> TYPE: DNA
<213> ORGANISM: Artificial
<220> FEATURE:
<223> OTHER INFORMATION: Example sequence flanking at least one
      targeting endonuclease binding site

<400> SEQUENCE: 1
ttcatctttg gacaagggaa taaagactcc ccacttgcta ctaagaacaa tacctaagtt      60
gcccagacat gactgtaccc attcagagac ctaccaccca ttagggctat gacactaaca     120
ctagcccctg gaggttgacc atgctaggca gtggggtct cacctatgac ccactcagat      180
aggggattgg tccagtgggt gggatctcag cctcatatag gtgtttgtgg tgagctttct     240
cctagacaag agaaccctga agaacagcaa gaaccagcta atatgatatg tagacatagt    300
gggttgctca aattttgtgt ttagtcatat tagaattgac ctcagtgacc actcagaaag    360
tgcccaagcc catctatagg ggccaaagtg ctattgactg gtgtgtctgt gaattgttcc     420
tccctacaga gttggtgctg atatatccta gcattctttg gaaaacctag ctagggactg     480
tcaagtgtaa gatacctcct gaattggagg gaacactagc tgccctgtac cttctggcta     540
gtaccttaca ccctgaatgg gttaggggt ctattatttg ctggaaatat accagtttca      600
gtagggctgc tgccttaggt cccacaaggt gtaacatgtg ctcaatagtt gcactaccac    660
atgcacgtga acttaatgat gttatagcca caacaccaac cttggtttgc agtttgacat    720
ccctctggaa tgggtgtagt catcttgctc tggatctgcc tgaatcattg gggctgtatg    780
cagcctgggc ttaaagtgaa gaatgggatg tcccagaaat attttgggtg agaagaatcc    840
tggagtagat ggtgacctga ctatccctgt cctatgggca caatctatca tcagatattg    900
cattcaaagg gctatcatgg gatcaagtcc taagtcaact gttgtttacc tggcagacat     960
tcatctagga gttctctttt atgccacccc acagtgatcc                         1000

<210> SEQ ID NO 2
<211> LENGTH: 1000
```

```
<212> TYPE: DNA
<213> ORGANISM: Artificial
<220> FEATURE:
<223> OTHER INFORMATION: Example sequence flanking at least one
      targeting endonuclease binding site

<400> SEQUENCE: 2
taaaatatag agtatagggg ttatcatcac agagaagcta ttgctggagg gcctctgtta      60
tttcctctcc atgccactcc cattttttaac ctaccaactg aaatcccaag ggagactcca    120
ccctgtaact agagtcctca gaggtgagcc atcccatatt aacaaatggg cattagggct    180
aggatgccaa gggatacctg aaatgggaag ttgtggggct gagtcctcct gggaatcaga    240
gataatatgt aaacagtttg ttgagagatt gatgagagct gactttgaga ggtggccatg    300
ctccctggtc ctcaataggg aaggcactac acaagaaacc tgggtttgat caactgcact    360
gtgtcctact cacacattgt gtgcctggaa aaatgttact tagtatttgg agggcctcca    420
gaacccccct gggtgcaaga ctgggtgcta gtgactgggt gaatgagtct tggacacagt    480
ggccttgtct aggttgtgtg aggtggctag gcatcatggc aatacctcat aattgatgag    540
tgaggaaaca agactaagtc cttgactcct cttattacat gacctggtgg atattatgct    600
ctcaatctgc aagctggaat gagtactggg tgcagatccc ctgggattct ggctacaaag    660
gtgaatgata gctagtctgt ttattagtag ccaaaaaagt cagtgagggg tgagtgccct    720
gggatgttgt taagttcaca ttgcacactt ggagaccctc tccatccagt aacataccag    780
agaaaactga ccaagccctc atgggtgtat gggaacaaca aacctcctgg ctacttcaag    840
ggcacataac accagcaagg agcctgtcat aaccaccatc tcaaacaata gaacttccta    900
agtgaagcaa tgacttcaaa tctacttgaa ggcatggagt ataagccatg ttcctttcag    960
aggggactgt acttctgtag attactttcc ctcattaacc                         1000

<210> SEQ ID NO 3
<211> LENGTH: 1000
<212> TYPE: DNA
<213> ORGANISM: Artificial
<220> FEATURE:
<223> OTHER INFORMATION: Example sequence flanking at least one
      targeting endonuclease binding site

<400> SEQUENCE: 3
tgcactcatg ttcatatcca tcacacccac tgaggcagat attgcagtga gagggttgca     60
tgtagggtcc tgctacctgg ccatgtaggt tttgggctgg gaaacaagga aaataatcca    120
aggtcccacc acacacaaga gcttctaaag gtcatggtgt gctggatgag aaggccatta    180
agaatctgga cctgttagag gaaccagtac cttacaaggg gatggtccac cctttaatca    240
tcagcttgac caaccccttt agtattcacc tctggcagac accagctttg ggattcctat    300
ctaaccattt ggccagtacc tgcactcac accagtggag actacagagc tacatgaatg    360
ggtcagatcc ccactccata gtgcatagct ggccacatga tactttaccc tagatatttg    420
ccataccgga gagtctgttc cctggttttcg accgggagtg ggccaccttg tctttgggc    480 ctaagctgtg gagtgatggt tctggcacca cctgtgggtc tgatagcaca tgccccctcc    540
tgcttatcca gtggtctgtt ctcatggata ttcaaggctt gtatagatgg aaaggatga    600 ggtgggtgaa ggctgttggg aagtgtgcct atgaagcccc aacaaagaga ttagacagta    660
cagctgatta cctaactcct tgggatgtct caaacaaatg tttcaaggcc cttttccctt    720
ggagcatgaa cctggcaata taaagtattt catctaaggg tcttatacaa attacccttt    780
```

| | |
|---|---|
| tacaccatta tggaccctga ggcaagctgt ctggcccact ctagctacct ggcaaatgtc | 840 |
| cacctgtagc tcataccaat ctttaagctc agagcaaagt tcagaagccc ttcagtgaca | 900 |
| gtggcaatgg ctatccagtg aacctgaccc aattagtggc ccattggatt attgaaaact | 960 |
| ggcagtgctg agtccatcac cccaaatact gtccataggc | 1000 |

<210> SEQ ID NO 4
<211> LENGTH: 1000
<212> TYPE: DNA
<213> ORGANISM: Artificial
<220> FEATURE:
<223> OTHER INFORMATION: Example sequence flanking at least one
      targeting endonuclease binding site

<400> SEQUENCE: 4

| | |
|---|---|
| tcagaccacc tcaccaccac aaagccttgc cctgaccacc ttgtaggctg gcctagacaa | 60 |
| tggtcatctt tggtgtcctc ctacccatta gagagagcca ctttcatacc agcatccagt | 120 |
| acctgaggaa taatggcctc aatggcatcc acaagtctca ctgggttggc ctgaggagca | 180 |
| gcccatgcct gtgccctagt ttaaagagga gtgatggtgc ttcctgcctc ttgagtggaa | 240 |
| cccttgttc catagtgaga atgggaggtg tgggccattc tgacaaagga ttttggacaa | 300 |
| gtccagctat taacacctgg ctagggatta acacagtgat acctggttga aggtgggagg | 360 |
| gcaagtgatc taacaaatct gttttgcaaa ggacatcaga atctgaggt gcctatagag | 420 |
| aacatcccca aggtttagca gaaagaactc tttaggctga ctcctggata tctttccaa | 480 |
| ggtggagcca ttaggcacac aactgggata cttgtcagta gggattaaag acctttataa | 540 |
| gtctcaaggt ctgggtgtta aggacagag tttattccaa gagggaatag agcaaaggca | 600 |
| tatatgggag tgtgggactg atccctgacc tctataatgg gagaggacat taggacctaa | 660 |
| ggtgcagaat agtggccttc cttagcctct ggaagtaatg gtgggattcc ccttaacata | 720 |
| ccctcctaaa aactgagaag tgggggaccc tgggggtgg tcaaaagatt agggactggt | 780 |
| gtgtaaggtg aacatgtgct gcaaggatca tcctggctgt ggttgcctca tcagctagag | 840 |
| aaagcccctg ccactaagcc atctgcaatg cctaatcttg gaacaaggaa gctgggactg | 900 |
| atccattatt gtcaaaacaa ctggtgaggg tgtgccctaa ggttggtgtt tactgattgt | 960 |
| ggtcttgggt ctagggactt ccagatatgg aaaaaattag | 1000 |

<210> SEQ ID NO 5
<211> LENGTH: 1000
<212> TYPE: DNA
<213> ORGANISM: Artificial
<220> FEATURE:
<223> OTHER INFORMATION: Example sequence flanking at least one
      targeting endonuclease binding site

<400> SEQUENCE: 5

| | |
|---|---|
| tgtaccaatg ttgtctccct taactaggga atatctggcc agccctcatg tataggtgtt | 60 |
| ttagtacact ctggtgagtg cattgctcag tcaactggtg gaacctgtcc ccccatccta | 120 |
| agggcaaccc cttgtaccca atttgaagat agggttgcta gagcagtgca atgaggtccc | 180 |
| ttgagtaagc agatggcctg ctaggcttca aacctcagac ctggtttttt gtatggcctg | 240 |
| ggatcagttg attatctacc ccatcatcaa taacttgccc ttaatactta aacatagggc | 300 |
| caatcattgt ggggcctcta gggaaactgt ttggtcctgg cactgtttct aaaaggggaa | 360 |
| cacatcataa tcagtaggaa acagaaaagc aagagtggag cctaccctag ttgcccagtg | 420 |
| tgggagcaaa attgatgtaa ggctacatag aaccccctata ccctagtagg tttacctgat | 480 |

| | |
|---|---|
| cattaggctg gctcccctg tcccatagag cacactcaat ctcatggcca agacttgaag | 540 |
| gttaaaatct catggggctg ctgatcagat tgcccacaaa aggtgttacc tgatacagtc | 600 |
| taacttctta cctgccagca aaaattttga tggaagtatc ctggcaactg taatcctcta | 660 |
| ccacttaaag attctagtat tgattaactt ctctccatac ctaaacagca gaatgtagca | 720 |
| taggttcata ggcttccttt ggaggttcac tatggaactt accactggat gacaaccctc | 780 |
| acctgtgcta ctctccctac cttggaggac cattgttgac ctagagactt atctgagtgc | 840 |
| taacccatga cattaacctc tgggggcttc cccatccctg acatgtggc tggagaaaat | 900 |
| ataggtcaaa acattgagc acattaggtt gccaatggtg aggctctcta agggtctggg | 960 |
| ttacaccaga ttagcagttc ttgacatggg agagtgtgat | 1000 |

<210> SEQ ID NO 6
<211> LENGTH: 1000
<212> TYPE: DNA
<213> ORGANISM: Artificial
<220> FEATURE:
<223> OTHER INFORMATION: Example sequence flanking at least one
    targeting endonuclease binding site

<400> SEQUENCE: 6

| | |
|---|---|
| tcgtctcacg cttgctgaat ctgatcagac tattaggccc ctcatcttga acatctttgc | 60 |
| catccttta gcttggttgt cagtggaaac tagggtccaa tggtttagag tccagccaga | 120 |
| tggaggttgg gcacaatgcc cctgcactat ccaccctagc tgtagaagtt atgcttgtcc | 180 |
| aaaggttatg caactgctgt ctgttgggct tgagccaaga gattggtggg aaatcttgcc | 240 |
| agagttggcc agttgtctcc tgtccaccaa catgatccta tatatgggtc cccaccctgg | 300 |
| ttcccaagcc actcttgtag gctgaagagg aaacacctca gaagctgagt agtccaagac | 360 |
| tgcttgcacc aagtttccac cccttacctg tcctgaaatt aaaggcacca gtgttccggt | 420 |
| tcccttggac tttctacttg tagtgtagca ctgggtggac ctactccctt tatcctggga | 480 |
| tcatggcact ttctattaca gtgggtcaca acttgaggca gccctgtagt tgagtatata | 540 |
| gtggagagca ccagatgatg attttacttg gtgtaggttg tccctggccc ttagctgtgg | 600 |
| tgaccccatt gtcatcctcc agttccaact ttccatttcc tgcaatgagt ggtccacatt | 660 |
| gctggctggg ggtggatcta tccctccatt tgggaagaaa cagtgatatg gacactaacc | 720 |
| accataagtg gatggattct tcatagagtg gttgcttttg cccaagtctg tgcagcagag | 780 |
| gtgtcaacct ggtccccaat tagtgaaata atctcacagc ctgggggcta ctcgtattag | 840 |
| gaccagtacc cattccagcc tggcccaaaa ctttagttga gcctagacct tcccacttac | 900 |
| atggactgat tgtggcggtt ccagatgact gttgacttcc tatccatttg gacttttgga | 960 |
| ggggccagaa acctattcct ccagtatagt cctccacatt | 1000 |

<210> SEQ ID NO 7
<211> LENGTH: 1000
<212> TYPE: DNA
<213> ORGANISM: Artificial
<220> FEATURE:
<223> OTHER INFORMATION: Example sequence flanking at least one
    targeting endonuclease binding site

<400> SEQUENCE: 7

| | |
|---|---|
| tgtcacccag aggttccctc tgtacagctg aaaatccatt agtaaagcca tataactccc | 60 |
| acccagaggg tggcagtatc ctatctcaat accactgctg ggtgatagct tctcatccct | 120 |

| | |
|---|---|
| tattactgag gcccaaggct atttgaccaa tagagctggt ctcccccact tcatcaaccc | 180 |
| tcactattaa ccctgtatct actagccact tgaaaccagt gccattctta aaatgtagga | 240 |
| tggttttagc catagagaac tggcatagtg gagggagtgt aggggcctct gcctggtggg | 300 |
| aaggaaccct gattcagagc tttaagcctg tagggcctta aaagtacctt gatgacttgg | 360 |
| gtccctaaag tcccttgggc caatgctgat ggatacctct tggtcccccaa aggattccct | 420 |
| tgaattacat ctgataggga ctccattgga cagcagcaca aaagtctgat ctaaactcac | 480 |
| ctgagatagt tactctgcat ccattgctgg ccattacaag tccatcacaa tgtggaaggt | 540 |
| tttggagggt gaacagagcc aaggacagct taatgacttt tcccaaggag ggctaggcac | 600 |
| tcacaagtgt tgtttgtaca ccatctggct atggcaaaac ccaaaacact ttatgcctgg | 660 |
| tggaaaagaa gtggccatga actttgttg atgggcagtt caagaaagag tgggtgatat | 720 |
| gaccctcttg ttaggcagag tttcaaggat tacctcctcc agcagatggg accatgttcc | 780 |
| ctcaaggtga gtagggccta aatcatgcct ggagttggag tttgtagggt ctatgagaca | 840 |
| ttttcatact gtagaaacat cctattgtag gaggcaagcc acaagtggat tgtttaaagt | 900 |
| ggtgtcagtt gaattgaata gaactccatg ttagagggtc cctagtgttg tccctgcatg | 960 |
| tattttagtg ccatccatct agtctataat atcacctagt | 1000 |

<210> SEQ ID NO 8
<211> LENGTH: 1000
<212> TYPE: DNA
<213> ORGANISM: Artificial
<220> FEATURE:
<223> OTHER INFORMATION: Example sequence flanking at least one
      targeting endonuclease binding site

<400> SEQUENCE: 8

| | |
|---|---|
| ttccaccctg acagagttaa tcctagctta cccaagggca gtaacatgca gtggatggca | 60 |
| gtagggcaca actctgctgt ttatccacct ttgagtgtct ggcatcctag cataactggc | 120 |
| tacatgagag ggttaatggt ccctggcagc cctggtggtt gcagcctgtc ctggctccaa | 180 |
| gttaatacec ctatattggg atctattgga cttgctgggc actgctgat ggttcaccag | 240 |
| ctatgtcaca tggttgggag tggacaccca agtgatacct cctaagtgag aggagcaaat | 300 |
| tacaatgcca cttatgggc cactgggtgc atttgaggag cctagtgttg ctttttcttg | 360 |
| ggacccattg gtgctgggaa agggattcca cacagtggga gggtgcctta aactcctcat | 420 |
| gtgggggttg gagctggaac taggagtggc tgactacaag cctggcttat tgacatcatt | 480 |
| agtggtgaat ggtttccaga gcttgacaaa gctgaactgt taggaggacc tgggaccaat | 540 |
| cagagataat cttctaactg gcattggtgc tattaagtaa accatctcac cagtcagcca | 600 |
| aggggttctt tcactgtcta cttgtgggac cttggccaca ctggtggacc catctattgg | 660 |
| tgttcaactg atcctgacat ttctcagctt aacagatgga cctacttggc accacattgg | 720 |
| ggggcttctt gacagttaag gtgacaccct tagttggctga catgtaaact ccagtgatcc | 780 |
| ttgggcactt gtgattccca ccttactgtc cacattgcca ccagtttgct accaaggctt | 840 |
| tactgtccca taaggttgtg gcctaacctt tgggctgcaa attaacatga atatccatag | 900 |
| aagatcaaga acctagtcac ttctgtagtg agtatgcag tgataagcag cttgactcct | 960 |
| agatggcagt tgggcttatg gaggatctac tgcctacagt | 1000 |

<210> SEQ ID NO 9
<211> LENGTH: 1000
<212> TYPE: DNA

<213> ORGANISM: Artificial
<220> FEATURE:
<223> OTHER INFORMATION: Example sequence flanking at least one
      targeting endonuclease binding site

<400> SEQUENCE: 9

```
tgcttgactc ttgcatagtg tacttccacc cacacactca aaccttaata taggccatcc      60
ctgaggcaag aactccagtg gcacttattc tatgatccca aactaggcaa gggactagca     120
caagccacca gcactggcta accctgaagg caaggatatt acatccagac acctcggacg     180
tagcacacct cttactgttc taatggactt aatctacgat ctcacgatca tgggggggtc     240
ttttggagtc ctacaatcct cttagaacaa cctatgggca tatatccatt cttctctcaa     300
cctgaggaga ctgggccaca acttccttat agggcattgt gagacctgct atgagggagt     360
agctggtggg ttggttccct ggcagtttag tagggccaaa tagcagatac gtcctttcat     420
ggaagtggga tagggaag agaaatgtag cattggagca tgttaaacta aaaagacttt       480
ttccagcatc ttgacccaaa agattacagt atttgaacta agtgtggagc accaaaaaac     540
aaccagtacc tcttacaatt ccccactctt tctgctactg tgccttatgc cctgcgttga     600
aagatattgc cattctgctc actgattatt tggtcagct ggattggcat gggaaaacaa      660
tcagtgtcca ccttacagag gccatgtaga tagtcactat attactcagc tcatagacct     720
gttaatcaag tttatctggt cactagggac tgcaaacaca atgcccatca ttcccacgct     780
agtgtaaacc tcactatttc tgtcaaaccc tgacatcatg ctagaggagc aacactgcct     840
ggatggtatc agaagaggat cgcccaagcc cccttccact gacttctgga gttgtgaagg     900
caacagctga taatggaagt cacctccttg accacgctac taaatgctta tcaattcacc     960
taccccttgga ttcaaggagc acttaccaaa gcccagaccc                         1000
```

<210> SEQ ID NO 10
<211> LENGTH: 1001
<212> TYPE: DNA
<213> ORGANISM: Artificial
<220> FEATURE:
<223> OTHER INFORMATION: Example sequence flanking at least one
      targeting endonuclease binding site

<400> SEQUENCE: 10

```
tttcataggg atatgtgagg actaaccttg gccaaaggag ctggaactgc ttatgtaagg      60
gccttagtcc aaattgctcc accctctggg aagctaatgg tccctccttg ggccttatag     120
tgaagcggaa tgggcatacc tagttgtctg ttctggggttg accctgctgg actcctcagt    180
tttagttcca ctaccaaaga ccttgagtct acagatgtgt tgctaaatcc tcacaaacct     240
ccaacaattt ttatgccctc tatcttctcc aaagttgctg ctgatccctg ccctcttatt     300
aagagccata gcaacaatac ctgaggtgag ggtttcacca ccaccatcta cctggaaaca     360
tcagccctcc tacatcttac cactcccaat aggggggctta gccactcttg aggtggtcat     420
cctttagcac ctttggttct aggataggct gggcaccctg gcagatgccc actgacagcc     480
ctagaggaac ccaaggggaa acaagccact acatacaact tggcaagcaa gtcaaggcaa     540
ggcttgacta atctatagat caaggttagt accacttaat tggggaagtc cagaaagtga     600
gcactaagta tgagcaaccc tctaatgact cagactaaag ggtgacaagc caagtaaatg     660
ttttctacat tagaggttcc tgggggcttg atttctactt ccttaggatt ccctggtctt     720
agggagaata tgtcctctta ggtgtcctag ccaaggacca gtaacaattc ttcctggacc     780
tctattttgc tttataccac actcaatcac tttgggattc attccatgcc tcaagagaca     840
```

```
ccaagataga gggaaattgg ggacccaagt ggggagcatt ttttgtctct ccttgagggc      900
aactctggac agtgaggaac taggagggtg tgatctctat atagatggag tgttgtacct      960
aagggtgaaa gctggcacat ccattggttc aagtttgccc t                        1001
```

<210> SEQ ID NO 11
<211> LENGTH: 1000
<212> TYPE: DNA
<213> ORGANISM: Artificial
<220> FEATURE:
<223> OTHER INFORMATION: Modified example sequence flanking at least one
      targeting endonuclease binding site

<400> SEQUENCE: 11

```
ttcatctttg gacaagggaa taaagactcc ccacttgcta ctaagaacaa tacctaagtt       60
gcccagacat gactgtaccc attcagagac ctaccaccca ttagggctat gacactaaca      120
ctagcccctg gaggttgacc atgctaggca gtggggtct cacctatgac ccactcagat      180
aggggtttaa accagtgggt gggatctcag cctcatatag gtgtttgtgg tgagctttct      240
cctagacaag agaaccctga agaacagcaa gaaccagcta atatgatatg tagacatagt      300
gggttgctca aattttgtgt ttagtcatat tagaattgac ctcagtgacc actcagaaag      360
tgcccaagcc catctatagg ggccaaagtg ctattgactg gtgtgtctgt gaattgttcc      420 tcctacaga gttggtgctg atatatccta gcattctttg gaaaacctag ctagggactg      480
tcaagtgtaa gatacctcct gaattggagg gaacactagc tgccctgtac cttctggcta      540
gtaccttaca ccctgaatgg gttagggggt ctattatttg ctggaaatat accagtttca      600
gtagggctgc tgccttaggt cccacaaggt gtaacatgtg ctcaatagtt gcactaccac      660
atgcacgtga acttaatgat gttatagcca caacaccaac cttggtttgc agtttgacat      720
ccctctggaa tgggtgtagt catcttgctc tggatctgcc tgaatcattg gggctgtatg      780
cagcctgggc ttaaagtgaa gaatgggatg tcccagaaat attttgggtg agaagaatcc      840
tggagtagat ggtgacctga ctatccctgt cctatgggca caatctatca tcagatattg      900
cattcaaagg gctatcatgg gatcaagtcc taagtcaact gttgtttacc tggcagacat      960
tcatctagga gttctctttt atgccacccc acagtgatcc                          1000
```

<210> SEQ ID NO 12
<211> LENGTH: 1000
<212> TYPE: DNA
<213> ORGANISM: Artificial
<220> FEATURE:
<223> OTHER INFORMATION: Modified example sequence flanking at least one
      targeting endonuclease binding site

<400> SEQUENCE: 12

```
tgcactcatg ttcatatcca tcacacccac tgaggcagat attgcagtga gagggttgca       60
tgtagggtcc tgctacctgg ccatgtaggt tttgggctgg gaaacaagga aaataatcca      120
aggtcccacc acacacaaga gcttctaaag gtcatggtgt gctggatgag aaggccatta      180
agtttaaaca cctgttagag gaaccagtac cttacaaggg gatggtccac cctttaatca      240
tcagcttgac caacccctttt agtattcacc tctggcagac accagctttg ggattcctat      300
ctaaccattt ggccagtacc tgcactcac accagtggag actacagagc tacatgaatg      360
ggtcagatcc ccactccata gtgcatagct ggccacatga actttaccc tagatatttg      420 ccataccgga gagtctgttc cctggtttcg accgggagtg ggccaccttg tctttggggc      480
```

| | |
|---|---|
| ctaagctgtg gagtgatggt tctggcacca cctgtgggtc tgatagcaca tgcccctcc | 540 |
| tgcttatcca gtggtctgtt ctcatggata ttcaaggctt gtatagatgg aaaaggatga | 600 |
| ggtgggtgaa ggctgttggg aagtgtgcct atgaagcccc aacaaagaga ttagacagta | 660 |
| cagctgatta cctaactcct tgggatgtct caaacaaatg tttcaaggcc ctttcccctt | 720 |
| ggagcatgaa cctggcaata taaagtattt catctaaggg tcttatacaa attaccctt | 780 |
| tacaccatta tggaccctga ggcaagctgt ctggcccact ctagctacct ggcaaatgtc | 840 |
| cacctgtagc tcataccaat ctttaagctc agagcaaagt tcagaagccc ttcagtgaca | 900 |
| gtggcaatgg ctatccagtg aacctgaccc aattagtggc ccattggatt attgaaaact | 960 |
| ggcagtgctg agtccatcac cccaaatact gtccataggc | 1000 |

<210> SEQ ID NO 13
<211> LENGTH: 1000
<212> TYPE: DNA
<213> ORGANISM: Artificial
<220> FEATURE:
<223> OTHER INFORMATION: Modified example sequence flanking at least one
      targeting endonuclease binding site

<400> SEQUENCE: 13

| | |
|---|---|
| taaaatatag agtataggg ttatcatcac agagaagcta ttgctggagg gcctctgtta | 60 |
| tttcctctcc atgccactcc catttttaac ctaccaactg aaatcccaag ggagactcca | 120 |
| ccctgtaact agagtcctca gaggtgagcc atccatatt aacaaatggg cattagggct | 180 |
| aggatgccaa gggatacctg aaatgggaag ttgtggggct gagtcctcct gggaatcaga | 240 |
| gataatatgt aaacagttg ttgagagatt gatgagagct gactttgaga ggtggccatg | 300 |
| ctccctggtc tcaataggg aaggcactac acaagaaacc tgggtttgat caactgcact | 360 |
| gtgtcctact cacacattgt gtgcctggaa aaatgttact tagtatttgg agggcctcca | 420 |
| gaacccccct gggtgcaaga ctgggtgcta gtgactgggt gaatgagtct tggacacagt | 480 |
| ggccttgtct aggttgtgtg aggtggctag gcatcatggc aatacctcat aattgatgag | 540 |
| tgaggaaaca agactaagtc cttgactcct cttattacat gacctggtgg atattatgtt | 600 |
| taaactctgc aagctggaat gagtactggg tgcagatccc ctgggattct ggctacaaag | 660 |
| gtgaatgata gctagtctgt ttattagtag ccaaaaaagt cagtgagggg tgagtgccct | 720 |
| gggatgttgt taagttcaca ttgcacactt ggagaccctc tccatccagt aacataccag | 780 |
| agaaaactga ccaagccctc atgggtgtat gggaacaaca aacctcctgg ctacttcaag | 840 |
| ggcacataac accagcaagg agcctgtcat aaccaccatc tcaaacaata gaacttccta | 900 |
| agtgaagcaa tgacttcaaa tctacttgaa ggcatggagt ataagccatg ttcctttcag | 960 |
| aggggactgt acttctgtag attactttcc ctcattaacc | 1000 |

<210> SEQ ID NO 14
<211> LENGTH: 1000
<212> TYPE: DNA
<213> ORGANISM: Artificial
<220> FEATURE:
<223> OTHER INFORMATION: Modified example sequence flanking at least one
      targeting endonuclease binding site

<400> SEQUENCE: 14

| | |
|---|---|
| tcagaccacc tcaccaccac aaagccttgc cctgaccacc ttgtaggctg gcctagacaa | 60 |
| tggtcatctt tggtgtcctc ctacccatta gagagagcca ctttcatacc agcatccagt | 120 |
| acctgaggaa taatggcctc aatggcatcc acaagtctca ctgggttggc ctgaggagca | 180 |

```
gcccatgcct gtgccctagt ttaaagagga gtgatggtgc ttcctgcctc ttgagtggaa        240 cccctttgttc catagtgaga atgggaggtg tgggccattc tgacaaagga ttttggacaa       300
gtccagctat taacacctgg ctagggatta acacagtgat acctggttga aggtgggagg        360
gcaagtgatc taacaaatct gttttgcaaa ggacatcaga atctgaggt gcctatagag         420 aacatcccca aggtttagca gaaagaactc tttaggctga ctcctggata atctttccaa        480
ggtggagcca ttaggcacac aactgggata cttgtcagta gggattaaag acctttataa       540
gtctcaaggg tttaaactta aggacagag tttattccaa gagggaatag agcaaaggca        600
tatatgggag tgtgggactg atccctgacc tctataatgg gagaggacat taggacctaa       660
ggtgcagaat agtggccttc cttagcctct ggaagtaatg gtgggattcc ccttaacata       720
ccctcctaaa aactgagaag tggggaccc tgggtggga tcaaaagatt agggactggt        780
gtgtaaggtg aacatgtgct gcaaggatca tcctggctgt ggttgcctca tcagctagag       840
aaagcccctg ccactaagcc atctgcaatg cctaatcttg gaacaaggaa gctgggactg       900
atccattatt gtcaaaacaa ctggtgaggg tgtgccctaa ggttggtgtt tactgattgt       960
ggtcttgggt ctagggactt ccagatatgg aaaaaattag                             1000

<210> SEQ ID NO 15
<211> LENGTH: 2099
<212> TYPE: DNA
<213> ORGANISM: Artificial
<220> FEATURE:
<223> OTHER INFORMATION: Example engineered landing pad

<400> SEQUENCE: 15
ggccggccgg atccttcatc tttggacaag ggaataaaga ctccccactt gctactaaga        60
acaataccta agttgcccag acatgactgt acccattcag agacctacca cccattaggg       120
ctatgacact aacactagcc cctggaggtt gaccatgcta ggcagtgggg gtctcaccta       180
tgacccactc agatagggggt ttaaaccagt gggtgggatc tcagcctcat ataggtgttt      240
gtggtgagct ttctcctaga caagagaacc ctgaagaaca gcaagaacca gctaatatga       300
tatgtagaca tagtggggttg ctcaaatttt gtgtttagtc atattagaat tgacctcagt      360
gaccactcag aaagtgccca agcccatcta taggggccaa agtgctattg actggtgtgt       420
ctgtgaattg ttcctcccta cagagttggt gctgatatat cctagcattc tttgaaaaac       480
ctagctaggg actgtcaagt gtaagatacc tcctgaattg gagggaacac tagctgccct       540
gtaccttctg gctagtacct tacaccctga atgggttagg gggtctatta tttgctggaa       600
atataccagt ttcagtaggg ctgctgcctt aggtcccaca aggtgtaaca tgtgctcaat       660
agttgcacta ccacatgcac gtgaacttaa tgatgttata gccacaacac caaccttggt      720
ttgcagtttg acatccctct ggaatgggtg tagtcatctt gctctggatc tgcctgaatc       780
attggggctg tatgcagcct gggcttaaag tgaagaatgg gatgtcccag aaatattttg       840
ggtgagaaga atcctggagt agatggtgac ctgactatcc ctgtcctatg gcacaatct        900 atcatcagat attgcattca aagggctatc atgggatcaa gtcctaagtc aactgttgtt      960
tacctggcag acattcatct aggagttctc ttttatgcca ccccacagtg atccgccttt      1020
tgcagtttat ccactaggga caggattgcc accccacagt ggggcctcta tgcccgggac     1080
aagtgtaaaa tatagagtat aggggttatc atcacagaga agctattgct ggagggcctc     1140
tgttatttcc tctccatgcc actcccattt ttaacctacc aactgaaatc ccaagggaga     1200
```

```
ctccaccctg taactagagt cctcagaggt gagccatccc atattaacaa atgggcatta    1260
gggctaggat gccaagggat acctgaaatg ggaagttgtg gggctgagtc ctcctgggaa    1320
tcagagataa tatgtaaaca gtttgttgag agattgatga gagctgactt tgagaggtgg    1380
ccatgctccc tggtcctcaa tagggaaggc actacacaag aaacctgggt ttgatcaact    1440
gcactgtgtc ctactcacac attgtgtgcc tggaaaaatg ttacttagta tttggagggc    1500
ctccagaacc cccctgggtg caagactggg tgctagtgac tgggtgaatg agtcttggac    1560
acagtggcct tgtctaggtt gtgtgaggtg gctaggcatc atggcaatac ctcataattg    1620
atgagtgagg aaacaagact aagtccttga ctcctcttat tacatgacct ggtggatatt    1680
atgtttaaac tctgcaagct ggaatgagta ctgggtgcag atccctgggg attctggcta    1740
caaaggtgaa tgatagctag tctgtttatt agtagccaaa aaagtcagtg aggggtgagt    1800
gccctgggat gttgttaagt tcacattgca cacttggaga ccctctccat ccagtaacat    1860
accagagaaa actgaccaag ccctcatggg tgtatgggaa caacaaacct cctggctact    1920
tcaagggcac ataacaccag caaggagcct gtcataacca ccatctcaaa caatagaact    1980
tcctaagtga agcaatgact tcaaatctac ttgaaggcat ggagtataag ccatgttcct    2040
ttcagagggg actgtacttc tgtagattac tttccctcat taaccagatc tggccggcc    2099

<210> SEQ ID NO 16
<211> LENGTH: 2103
<212> TYPE: DNA
<213> ORGANISM: Artificial
<220> FEATURE:
<223> OTHER INFORMATION: Example engineered landing pad

<400> SEQUENCE: 16
ggccggccgg atcctgcact catgttcata tccatcacac ccactgaggc agatattgca      60
gtgagagggt tgcatgtagg gtcctgctac ctggccatgt aggttttggg ctgggaaaca     120
aggaaaataa tccaaggtcc caccacacac aagagcttct aaaggtcatg gtgtgctgga     180
tgagaaggcc attaagttta aacacctgtt agaggaacca gtaccttaca aggggatggt     240
ccacccttta atcatcagct tgaccaaccc ctttagtatt cacctctggc agacaccagc     300
tttgggattc ctatctaacc atttggccag tacctggcac tcacaccagt ggagactaca     360
gagctacatg aatgggtcag atccccactc catagtgcat agctggccac atgatacttt     420
accctagata tttgccatac cggagagtct gttccctggt ttcgaccggg agtgggccac     480
cttgtctttg gggcctaagc tgtggagtga tggttctggc accacctgtg ggtctgatag     540
cacatgcccc ctcctgctta ccagtggtc tgttctcatg gatattcaag gcttgtatag     600
atggaaaagg atgaggtggg tgaaggctgt tgggaagtgt gcctatgaag ccccaacaaa     660
gagattagac agtacagctg attacctaac tccttgggat gtctcaaaca aatgtttcaa     720
ggcccttttc ccttggagca tgaacctggc aatataaagt atttcatcta agggtcttat     780
acaaattacc cttttacacc attatggacc ctgaggcaag ctgtctggcc cactctagct     840
acctggcaaa tgtccaccct tagctcatac caatctttaa gctcagagca agttcagaa      900
gcccttcagt gacagtggca atggctatcc agtgaacctg acccaattag tgcccattg      960
gattattgaa aactggcagt gctgagtcca tcaccccaaa tactgtccat aggcaagact    1020
cccgcccatc tctctatgcc cgggacaagt ggagtccatg ctcaacaccg tgcactaggg    1080
acaggattgt cagaccacct caccaccaca aagccttgcc ctgaccacct tgtaggctgg    1140
cctagacaat ggtcatcttt ggtgtcctcc tacccattag agagagccac tttcatacca    1200
```

```
gcatccagta cctgaggaat aatggcctca atggcatcca caagtctcac tgggttggcc      1260
tgaggagcag cccatgcctg tgccctagtt taaagaggag tgatggtgct tcctgcctct      1320
tgagtggaac cccttgttcc atagtgagaa tgggaggtgt gggccattct gacaaaggat      1380
tttggacaag tccagctatt aacacctggc tagggattaa cacagtgata cctggttgaa      1440
ggtgggaggg caagtgatct aacaaatctg ttttgcaaag gacatcagaa atctgaggtg      1500
cctatagaga acatccccaa ggtttagcag aaagaactct ttaggctgac tcctggataa      1560
tctttccaag gtggagccat taggcacaca actgggatac ttgtcagtag ggattaaaga      1620
cctttataag tctcaagggt ttaaacttaa aggacagagt ttattccaag agggaataga      1680
gcaaaggcat atatgggagt gtgggactga tccctgacct ctataatggg agaggacatt      1740
aggacctaag gtgcagaata gtggccttcc ttagcctctg gaagtaatgg tgggattccc      1800
cttaacatac cctcctaaaa actgagaagt gggggaccct ggggtgggat caaaagatta      1860
gggactggtg tgtaaggtga acatgtgctg caaggatcat cctggctgtg gttgcctcat      1920
cagctagaga aagcccctgc cactaagcca tctgcaatgc ctaatcttgg aacaaggaag      1980
ctgggactga tccattattg tcaaaacaac tggtgagggt gtgccctaag gttggtgttt      2040
actgattgtg gtcttgggtc tagggacttc cagatatgga aaaaattaga gatctggccg      2100
gcc                                                                    2103

<210> SEQ ID NO 17
<211> LENGTH: 990
<212> TYPE: DNA
<213> ORGANISM: Artificial
<220> FEATURE:
<223> OTHER INFORMATION: Modified example sequence flanking at least one
      targeting endonuclease binding site

<400> SEQUENCE: 17
tgtaccaatg ttgtctccct taactaggga atatctggcc agccctcatg tataggtgtt        60
ttagtacact ctggtgagtg cattgctcag tcaactggtg gaacctgtcc ccccatccta       120
agggcaaccc cttgtaccca atttgaagat agggttgcta gagcagtgca atgaggtccc       180
ttgagtaagc agatggcctg ctaggcttca aacctcagac ctggtttttt gtatggcctg       240
ggatcagttg attatctacc ccatcatcaa taacttgccc ttaatactta aacatagggc       300
caatcattgt ggggcctcta gggaaactgt ttggtcctgg cactgtttct aaaaggggaa       360
cacatcataa tcagtaggaa acagaaaagc aagagtggag cctaccctag ttgcccagtg       420
tgggagcaaa attgatgtaa ggctacatag aaccccctata cctagtagg gtttaaacct       480 gatcattagg ctggctcccc ctgtcccata gagcacactc aatctcatgg ccaagacttg       540
aaggttaaaa tctcatgggg ctgctgatca gattgcccac aaaaggtgtt acctgataca       600
gtctaacttc ttacctgcca gcaaaaattt tgatggaagt atcctggcaa ctgtaatcct       660
ctaccactta aagattctag tattgattaa cttctctcca tacctaaaca gcagaatgta       720
gcataggttc ataggcttcc tttggaggtt cactatggaa cttaccactg atgacaacc       780 ctcacctgtg ctactctccc taccttggag gaccattgtt gacctagaga cttatctgag       840
tgctaaccca tgacattaac ctctgggggc ttccccatcc ctggacatgt ggctggagaa       900
aatataggtc aaaaacattg agcacattag gtcgactgcc aatggtgagg ctctctaagg       960
gtctgggtta caccagatta gcagttcttg                                        990
```

```
<210> SEQ ID NO 18
<211> LENGTH: 1022
<212> TYPE: DNA
<213> ORGANISM: Artificial
<220> FEATURE:
<223> OTHER INFORMATION: Modified example sequence flanking at least one
      targeting endonuclease binding site

<400> SEQUENCE: 18
catgggagag tgtgattcgt ctcacgcttg ctgaatctcg agtcagacta ttaggcccct    60
catcttgaac atctttgcca tccttttagc ttggttgtca gtggaaacta gggtccaatg   120
gtttagagtc cagccagatg gaggttgggc acaatgcccc tgcactatcc acctagctg   180 tagaagttat gcttgtccaa aggttatgca actgctgtct gttgggcttg agccaagaga   240
ttggtgggaa atcttgccag agttggccag ttgtctcctg tccaccaaca tgatcctata   300
tatgggtccc caccctggtt cccaagccac tcttgtaggc tgaagaggaa acacctcaga   360
agctgagtag tccaagactg cttgcaccaa gtttccaccc cttacctgtc ctgaaattaa   420
aggcaccagt gttccggttc ccttggactt tctacttgta gtgtagcact gggtggacct   480
actcccgttt aaactcctgg gatcatggca cttctctatta cagtgggtca caacttgagg   540
cagccctgta gttgagtata tagtggagag caccagatga tgattttact tggtgtaggt   600
tgtccctggc ccttagctgt ggtgaccca ttgtcatcct ccagttccaa ctttccattt    660
cctgcaatga gtggtccaca ttgctggctg ggggtggatc tatccctcca tttgggaaga   720
aacagtgata tggacactaa ccaccataag tggatggatt cttcatagag tggttgcttt   780
tgcccaagtc tgtgcagcag aggtgtcaac ctggtcccca attagtgaaa taatctcaca   840
gcctgggggc tactcgtatt aggaccagta cccattccag cctggcccaa aactttagtt   900
gagcctagac cttcccactt acatggactg attgtggcgg ttccagatga ctgttgactt   960
cctatccatt tggacttttg gaggggccag aaacctattc ctccagtata gtcctccaca  1020
tt                                                                  1022

<210> SEQ ID NO 19
<211> LENGTH: 2082
<212> TYPE: DNA
<213> ORGANISM: Artificial
<220> FEATURE:
<223> OTHER INFORMATION: Example engineered landing pad

<400> SEQUENCE: 19
tgtaccaatg ttgtctccct taactaggga atatctggcc agccctcatg tataggtgtt    60
ttagtacact ctggtgagtg cattgctcag tcaactggtg gaacctgtcc ccccatccta   120
agggcaaccc cttgtaccca atttgaagat agggttgcta gagcagtgca atgaggtccc   180
ttgagtaagc agatggcctg ctaggcttca aacctcagac ctggtttttt gtatggcctg   240
ggatcagttg attatctacc ccatcatcaa taacttgccc ttaatactta aacatagggc   300
caatcattgt ggggcctcta gggaaactgt ttggtcctgg cactgtttct aaaaggggaa   360
cacatcataa tcagtaggaa acagaaaagc aagagtggag cctaccctag ttgcccagtg   420
tgggagcaaa attgatgtaa ggctacatag aaccccctata ccctagtagg gtttaaacct   480
gatcattagg ctggctcccc ctgtcccata gagcacactc aatctcatgg ccaagacttg   540
aaggttaaaa tctcatgggg ctgctgatca gattgcccac aaaaggtgtt acctgataca   600
gtctaacttc ttacctgcca gcaaaaattt tgatggaagt atcctggcaa ctgtaatcct   660
ctaccactta aagattctag tattgattaa cttctctcca tacctaaaca gcagaatgta   720
```

```
gcataggttc ataggcttcc tttggaggtt cactatggaa cttaccactg gatgacaacc      780
ctcacctgtg ctactctccc taccttggag gaccattgtt gacctagaga cttatctgag      840
tgctaaccca tgacattaac ctctgggggc ttccccatcc ctggacatgt ggctggagaa      900 aataggtc aaaaacattg agcacattag gtcgactgcc aatggtgagg ctctctaagg        960
gtctgggtta caccagatta gcagttcttg gccttttgca gtttatctct atgcccggga     1020
caagtgaaga ctcccgccca tccaggatga ggatgaccaa catgggagag tgtgattcgt     1080
ctcacgcttg ctgaatctcg agtcagacta ttaggcccct catcttgaac atctttgcca     1140 tcctttagc ttggttgtca gtggaaacta gggtccaatg gtttagagtc cagccagatg      1200
gaggttgggc acaatgcccc tgcactatcc accctagctg tagaagttat gcttgtccaa     1260
aggttatgca actgctgtct gttgggcttg agccaagaga ttggtgggaa atcttgccag     1320
agttggccag ttgtctcctg tccaccaaca tgatcctata tatgggtccc caccctggtt     1380
cccaagccac tcttgtaggc tgaagaggaa acacctcaga agctgagtag tccaagactg     1440
cttgcaccaa gtttccaccc cttacctgtc ctgaaattaa aggcaccagt gttccggttc     1500
ccttggactt tctacttgta gtgtagcact gggtggacct actcccgttt aaactcctgg     1560
gatcatggca ctttctatta cagtgggtca caacttgagg cagccctgta gttgagtata     1620
tagtggagag caccagatga tgattttact tggtgtaggt tgtccctggc ccttagctgt     1680
ggtgacccca ttgtcatcct ccagttccaa ctttccattt cctgcaatga gtggtccaca     1740
ttgctggctg ggggtggatc tatccctcca tttgggaaga aacagtgata tggacactaa     1800
ccaccataag tggatggatt cttcatagag tggttgcttt tgcccaagtc tgtgcagcag     1860
aggtgtcaac ctggtcccca attagtgaaa taatctcaca gcctggggc tactcgtatt      1920 aggaccagta cccattccag cctggcccaa aactttagtt gagcctagac cttcccactt     1980
acatggactg attgtggcgg ttccagatga ctgttgactt cctatccatt tggacttttg     2040
gaggggccag aaacctattc ctccagtata gtcctccaca tt                        2082
```

<210> SEQ ID NO 20
<211> LENGTH: 530
<212> TYPE: DNA
<213> ORGANISM: Artificial
<220> FEATURE:
<223> OTHER INFORMATION: ZFN module 2:4-MCS-2:4

<400> SEQUENCE: 20

```
actagtctcg agtgtccgat actggatcgt tctttcatgt agcagagcgg ttggcccaaa       60
tgtttattgg gatatcgtga gtcagatgtt cacttggtca atgggtacag tccgccgcca      120
gtgtctattt gagcctctct gcaagactcc cgcccatctc tctatgcccg ggacaagtgt      180
ggacgacaag cgagtgcagc cggcttacag cctttgcag tttatctcta tgcccgggac       240
aagtgattaa taagctttta attaacctgc agggcatgcg tcgacaagac tcccgcccat      300
ctctctatgc ccgggacaag tgtcgagagg aatggccatg agtatttggt ttgccttttg      360
cagtttatct ctatgcccgg gacaagtgca gagcggttgg cccaaatgtt tattgggata     420
tcgtgagtca gatgttcact tggtcaatgg gtacagtccg ccgccagtgt ctatttgagc     480
ctctctgcgt acatgataac ctcagttggc gagcgttgct cgagactagt                 530
```

<210> SEQ ID NO 21
<211> LENGTH: 26
<212> TYPE: DNA

```
<213> ORGANISM: Artificial
<220> FEATURE:
<223> OTHER INFORMATION: Oligonucleotide 610F

<400> SEQUENCE: 21
gctactaaga acaataccta agttgc                                              26

<210> SEQ ID NO 22
<211> LENGTH: 19
<212> TYPE: DNA
<213> ORGANISM: Artificial
<220> FEATURE:
<223> OTHER INFORMATION: Oligonucleotide 611F

<400> SEQUENCE: 22
tgcactcatg ttcatatcc                                                      19

<210> SEQ ID NO 23
<211> LENGTH: 19
<212> TYPE: DNA
<213> ORGANISM: Artificial
<220> FEATURE:
<223> OTHER INFORMATION: Oligonucleotide 611R

<400> SEQUENCE: 23
tgtacaagaa agctgggtg                                                      19

<210> SEQ ID NO 24
<211> LENGTH: 19
<212> TYPE: DNA
<213> ORGANISM: Artificial
<220> FEATURE:
<223> OTHER INFORMATION: Oligonucleotide YFPF_3302

<400> SEQUENCE: 24
tatggtccag agttgaagg                                                      19

<210> SEQ ID NO 25
<211> LENGTH: 19
<212> TYPE: DNA
<213> ORGANISM: Artificial
<220> FEATURE:
<223> OTHER INFORMATION: Oligonucleotide YFPR_4577

<400> SEQUENCE: 25
tcatctgcac aactggtga                                                      19

<210> SEQ ID NO 26
<211> LENGTH: 19
<212> TYPE: DNA
<213> ORGANISM: Artificial
<220> FEATURE:
<223> OTHER INFORMATION: Oligonucleotide YFPF_4302

<400> SEQUENCE: 26
tctttcccaa cacatgacc                                                      19

<210> SEQ ID NO 27
<211> LENGTH: 29
<212> TYPE: DNA
<213> ORGANISM: Artificial
<220> FEATURE:
<223> OTHER INFORMATION: Primer TQPATS

<400> SEQUENCE: 27
acaagagtgg attgatgatc tagagaggt                                           29
```

<210> SEQ ID NO 28
<211> LENGTH: 29
<212> TYPE: DNA
<213> ORGANISM: Artificial
<220> FEATURE:
<223> OTHER INFORMATION: Primer TQPATA

<400> SEQUENCE: 28
ctttgatgcc tatgtgacac gtaaacagt                               29

<210> SEQ ID NO 29
<211> LENGTH: 29
<212> TYPE: DNA
<213> ORGANISM: Artificial
<220> FEATURE:
<223> OTHER INFORMATION: Primer TQPATFQ

<400> SEQUENCE: 29
ggtgttgtgg ctggtattgc ttacgctgg                               29

<210> SEQ ID NO 30
<211> LENGTH: 21
<212> TYPE: DNA
<213> ORGANISM: Artificial
<220> FEATURE:
<223> OTHER INFORMATION: Primer ZGP3S

<400> SEQUENCE: 30
cctgctccac taccagtaca a                                       21

<210> SEQ ID NO 31
<211> LENGTH: 21
<212> TYPE: DNA
<213> ORGANISM: Artificial
<220> FEATURE:
<223> OTHER INFORMATION: Primer ZGP3A

<400> SEQUENCE: 31
gtccaagaag gtgaccttct c                                       21

<210> SEQ ID NO 32
<211> LENGTH: 23
<212> TYPE: DNA
<213> ORGANISM: Artificial
<220> FEATURE:
<223> OTHER INFORMATION: Primer TQZGP3

<400> SEQUENCE: 32
agatcaccga ctttgcgctc ttt                                     23

<210> SEQ ID NO 33
<211> LENGTH: 20
<212> TYPE: DNA
<213> ORGANISM: Artificial
<220> FEATURE:
<223> OTHER INFORMATION: Primer GAAD1F

<400> SEQUENCE: 33
tgttcggttc cctctaccaa                                         20

<210> SEQ ID NO 34
<211> LENGTH: 22
<212> TYPE: DNA
<213> ORGANISM: Artificial
<220> FEATURE:

```
<223> OTHER INFORMATION: Primer GAAD1R

<400> SEQUENCE: 34
caacatccat caccttgact ga                                        22

<210> SEQ ID NO 35
<211> LENGTH: 24
<212> TYPE: DNA
<213> ORGANISM: Artificial
<220> FEATURE:
<223> OTHER INFORMATION: Primer GAAD1P

<400> SEQUENCE: 35
cacagaaccg tcgcttcagc aaca                                      24

<210> SEQ ID NO 36
<211> LENGTH: 18
<212> TYPE: DNA
<213> ORGANISM: Artificial
<220> FEATURE:
<223> OTHER INFORMATION: Primer IVF-Taq

<400> SEQUENCE: 36
tggcggacga cgacttgt                                             18

<210> SEQ ID NO 37
<211> LENGTH: 19
<212> TYPE: DNA
<213> ORGANISM: Artificial
<220> FEATURE:
<223> OTHER INFORMATION: Primer INR-Taq

<400> SEQUENCE: 37
aaagtttgga ggctgccgt                                            19

<210> SEQ ID NO 38
<211> LENGTH: 26
<212> TYPE: DNA
<213> ORGANISM: Artificial
<220> FEATURE:
<223> OTHER INFORMATION: Primer IV-Probe

<400> SEQUENCE: 38
cgagcagacc gccgtgtact tctacc                                    26
```

ENGINEERED LANDING PADS FOR GENE TARGETING IN PLANTS

FIELD OF THE DISCLOSURE

The invention generally relates to compositions and methods for generating transgenic organisms, for example, plants. In certain embodiments, methods of the invention allow the incorporation of engineered landing pads (ELPs) into a genomic site, thereby facilitating the introduction of further nucleic acid molecules of interest into a defined genomic site containing one or more ELPs. In some embodiments, the ELPs may comprise regions of nucleotide sequence comprising essentially random sequence flanking zinc finger nuclease (ZFN) binding sites.

BACKGROUND

Many plants are genetically transformed with genes from other species to introduce desirable traits, such as to improve agricultural value through, for example, improving nutritional value quality, increasing yield, conferring pest or disease resistance, increasing drought and stress tolerance, improving horticultural qualities such as pigmentation and growth, and/or imparting herbicide resistance, enabling the production of industrially useful compounds and/or materials from the plant, and/or enabling the production of pharmaceuticals. The introduction of cloned genes into plant cells and recovery of stable fertile transgenic plants can be used to make such modifications of a plant and has allowed the genetic engineering of plants for (e.g., for crop improvement). In these methods, foreign DNA is typically randomly introduced into the nuclear or plastid DNA of the eukaryotic plant cell, followed by isolation of cells containing the foreign DNA integrated into the cell's DNA, to produce stably transformed plant cells.

The first generations of transgenic plants were typically generated by *Agrobacterium*-mediated transformation technology. Successes with these techniques spurred the development of other methods to introduce a nucleic acid molecule of interest into the genome of a plant, such as PEG-mediated DNA uptake in protoplasts, microprojectile bombardment, and silicon whisker-mediated transformation.

In all of these plant transformation methods, however, the transgenes incorporated in the plant genome are integrated in a random fashion and in unpredictable copy number. Frequently, the transgenes can be integrated in the form of repeats, either of the whole transgene or of parts thereof. Such a complex integration pattern may influence the expression level of the transgenes (e.g., by destruction of the transcribed RNA through posttranscriptional gene silencing mechanisms, or by inducing methylation of the introduced DNA), thereby down-regulating transcription of the transgene. Also, the integration site per se can influence the level of expression of the transgene. The combination of these factors results in a wide variation in the level of expression of the transgenes or foreign DNA of interest among different transgenic plant cell and plant lines. Moreover, the integration of the foreign DNA of interest may have a disruptive effect on the region of the genome where the integration occurs and can influence or disturb the normal function of that target region, thereby leading to often undesirable side-effects.

The foregoing necessitate that, whenever the effect of introduction of a particular foreign DNA into a plant is investigated, a large number of transgenic plant lines are generated and analyzed in order to obtain significant results. Likewise, in the generation of transgenic crop plants, where a particular DNA of interest is introduced in plants to provide the transgenic plant with a desired phenotype, a large population of independently created transgenic plant lines is created to allow the selection of those plant lines with optimal expression of the transgenes, and with minimal or no side-effects on the overall phenotype of the transgenic plant. Particularly in this field, more directed transgenic approaches are desired, for example, in view of the burdensome regulatory requirements and high costs associated with the repeated filed trials required for the elimination of the unwanted transgenic events. Furthermore, it will be clear that the possibility of targeted DNA insertion would also be beneficial in the process of transgene stacking.

Several methods have been developed in an effort to control transgene insertion in plants. See, e.g., Kumar and Fladung (2001) Trends Plant Sci. 6:155-9. These methods rely on homologous recombination-based transgene integration. This strategy has been successfully applied in prokaryotes and lower eukaryotes. Paszkowski et al. (1988) EMBO J. 7:4021-6. However, for plants, until recently the predominant mechanism for transgene integration is based on illegitimate recombination which involves little homology between the recombining DNA strands. A major challenge in this area is therefore the detection of the rare homologous recombination events, which are masked by the far more efficient integration of the introduced foreign DNA via illegitimate recombination.

Custom-designed zinc finger nucleases (ZFNs) are proteins designed to deliver a targeted site-specific double-strand break in DNA, with subsequent recombination of the cleaved ends. ZFNs combine the non-specific cleavage domain of a restriction endonuclease, such as for example FokI, with zinc finger DNA-binding proteins. See, e.g., Huang et al. (1996) J. Protein Chem. 15:481-9; Kim et al. (1997) Proc. Natl. Acad. Sci. USA 94:3616-20; Kim et al. (1996) Proc. Natl. Acad. Sci. USA 93:1156-60; Kim et al. (1994) Proc Natl. Acad. Sci. USA 91:883-7; Kim et al. (1997b) Proc. Natl. Acad. Sci. USA 94:12875-9; Kim et al. (1997c) Gene 203:43-9; Kim et al. (1998) Biol. Chem. 379:489-95; Nahon and Raveh (1998) Nucleic Acids Res. 26:1233-9; Smith et al. (1999) Nucleic Acids Res. 27:674-81. Individual zinc finger motifs can be designed to target and bind to a large range of DNA sites. Canonical $Cys_2His_2$ as well as non-canonical $Cys_3His$ zinc finger proteins bind DNA by inserting an α-helix into the major groove of the double helix. Recognition of DNA by zinc fingers is modular: each finger contacts primarily three consecutive base pairs in the target, and a few key residues in the protein mediate recognition. It has been shown that FokI restriction endonuclease must dimerize via the nuclease domain in order to cleave DNA, inducing a double-strand break. Similarly, ZFNs also require dimerization of the nuclease domain in order to cut DNA. Mani et al. (2005) Biochem. Biophys. Res. Commun. 334:1191-7; Smith et al. (2000) Nucleic Acids Res. 28:3361-9. Dimerization of the ZFN is facilitated by two adjacent, oppositely oriented binding sites. Id.

SUMMARY OF THE DISCLOSURE

Disclosed herein are methods of introducing a nucleic acid molecule into the genome of a host organism exhibiting a low rate of homologous recombination, e.g., a plant or animal species. In particular examples, "engineered landing pads" (ELPs) are used, wherein the ELPs may comprise regions of nucleotide sequence comprising nucleotide sequences substantially lacking homology with the genome of the host organism (e.g., randomly-generated sequences) flanking binding sites for DNA-binding domains (e.g., zinc finger proteins (ZFPs), meganucleases, or leucine zippers). The DNA-binding domains that target the binding sites of the ELPs may naturally include DNA-cleaving functional domains or may be part of fusion proteins that further comprise a functional domain, for example an endonuclease cleavage domain or cleavage half-domain (e.g., a ZFN, a recombinase, a transposase, or a homing endonuclease, including a homing endonuclease with a modified DNA-binding domain). This class of DNA-binding and cleaving proteins is collectively referred to herein as "targeting endonucleases." In particular examples, non-randomized nucleotide sequence from biological sources other than the host organism may also be used; non-homology to the genome of the target organism is suitable. Thus, in some examples, the nucleotide sequences may be designed to ensure substantially no homology to regions of any sequenced target plant genome.

In some examples, ELPs may provide regions of homology and binding sites for high-activity for targeting endonucleases (e.g., ZFNs) for homology-directed gene targeting. Consequently, ELPs may reduce or eliminate the need to use other nucleotide sequences, external or internal, in a nucleic acid insert. ELPs may be designed to lack any spurious open reading frames, and contain or lack restriction enzyme sites, as preferred, for construction of vectors or analysis of plants transformed with a nucleic acid molecule of interest. In some examples, ELPs may be flanked by non-identical restriction sites which generate compatible ends upon restriction enzyme digestion, but the hybrid ligated sites are not cleavable by either of the restriction enzymes. In these and other examples, this allows concatenation of the ELPs into larger arrays, each with unique regions of homology and targeting endonuclease binding sites (e.g., ZFN binding sites).

In some examples, ELPs can be incorporated randomly into a target genome, or targeted to genomic sites that have been shown to accommodate transgenic inserts without any, or with acceptable, detrimental impact to the resultant transgenic plants. Regions of homology in the genomic target site may be identical to the regions of homology in the targeted donor nucleic acid molecule, thereby facilitating homology-directed recombination after double stranded cleavage by targeting endonucleases (e.g., ZFNs).

Accordingly, methods of designing and generating ELPs are disclosed, as well as methods of using ELPs to transform a plant with a nucleic acid molecule of interest. Also disclosed are nucleic acid molecules useful in the invention, and genetically modified plants produced by methods according to the invention.

The foregoing and other features will become more apparent from the following detailed description of several embodiments, which proceeds with reference to the accompanying figures.

DETAILED DESCRIPTION

I. Overview of Several Embodiments

Figure 1:
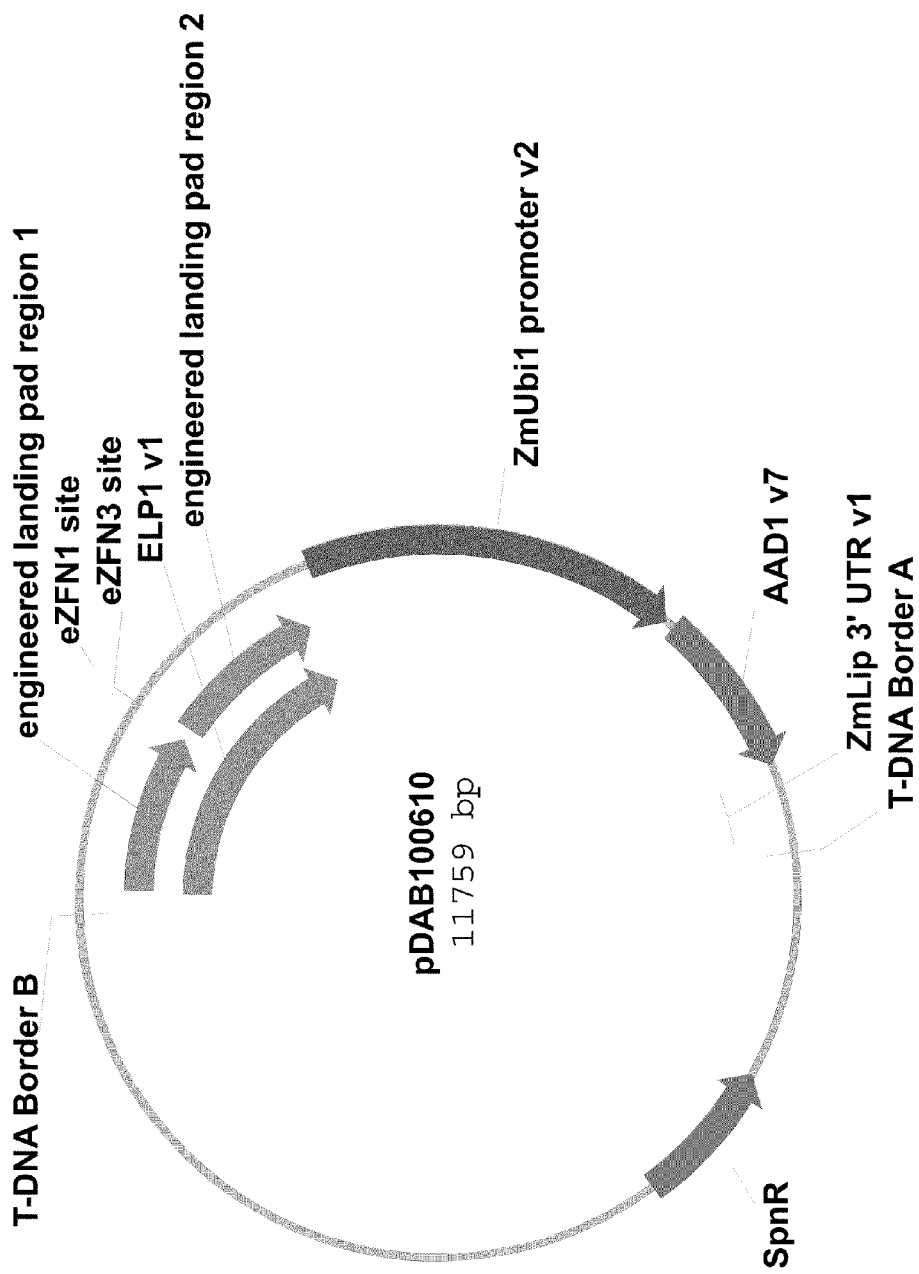
FIG. 1 includes a depiction of a representative vector comprising an ELP, pDAB100610.

In some embodiments, methods are provided for introducing nucleic acid molecules comprising "engineered landing pads" (ELPs) into a host organism, such that the integration of further nucleic acid molecules of interest into the host organism is facilitated. In embodiments, ELPs may comprise regions of nucleic acid sequence that are not homologous to native sequences of the host organism (e.g., essentially randomly generated nucleic acid sequences, which may then be selected for insertion based on certain desirable criteria as disclosed herein), flanking targeting endonuclease recognition sites (e.g., ZFN recognition sites). Sites for integration of the ELPs may be random, may be determined by identifying, for example, a structural gene within the host genome that has a level expression desired for a nucleic acid molecule of interest to be introduced at the site of the ELP, or may be determined by identifying locations within the host genome that do not impart a metabolic, functional, agronomic (if a plant) or other penalty to the transformed host organism when the ELP is introduced at the site. ELPs may be introduced in tandem into the genome, such that, for example, ELPs are present as concatemers in an organism produced according to methods of the invention.

In some embodiments, integration of a nucleic acid molecule of interest is performed at an ELP site. In embodiments, a nucleic acid molecule of interest to be introduced at an ELP site is associated with one or more targeting endonucleases, provided as polypeptides or expressed from introduced RNA or DNA. In addition, the introduced nucleic acid molecule can include an ELP different from that already incorporated into the host genome. Those of skill in the art will appreciate that a nucleic acid sequence introduced into the host genome at a site where a native nucleic acid sequence is expressed in the wild-type organism will be expected to be expressed in a similar manner as the native nucleic acid sequence. For example, if the native nucleic acid sequence is expressed in the wild-type organism under the control of regulatory elements (e.g., such that, for example, the nucleic acid sequence is expressed in a tissue-specific or development-specific manner), the introduced nucleic acid sequence will be expected to undergo the same or similar regulatory control. Thus, ELPs may facilitate desired temporal and/or spatial expression of a nucleic acid molecule of interest introduced at the ELP site.

II. Abbreviations

| | |
|---|---|
| ELISA | enzyme-linked immunosorbent assay |
| ELP | engineered landing pad |
| ZFN | zinc finger nuclease |

III. Terms

Gene expression: The process by which the coded information of a nucleic acid transcriptional unit (including, e.g., genomic DNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

Hybridization: Oligonucleotides and their analogs hybridize by hydrogen bonding, which includes Watson-Crick, Hoogsteen or reversed Hoogsteen hydrogen bonding, between complementary bases. Generally, nucleic acid molecules consist of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide and the DNA or RNA target. The oligonucleotide need not be 100% complementary to its target sequence to be specifically hybridizable. An oligonucleotide is specifically hybridizable when binding of the oligonucleotide to the target DNA or RNA molecule interferes with the normal function of the target DNA or RNA, and there is sufficient degree of complementarity to avoid non-specific binding of the oligonucleotide to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the chosen hybridization method and the composition and length of the hybridizing nucleic acid sequences. Generally, the temperature of hybridization and the ionic strength (especially the $Na^+$ and/or $Mg^{2+}$ concentration) of the hybridization buffer will contribute to the stringency of hybridization, though wash times also influence stringency. Calculations regarding hybridization conditions required for attaining particular degrees of stringency are discussed in Sambrook et al. (ed.), *Molecular Cloning: A Laboratory Manual,* 2nd ed., vol. 1-3, Cold Spring Harbor Laboratory Press, Cold Spring Harbor, N.Y., 1989, chs. 9 and 11.

For purposes of the present disclosure, "stringent conditions" encompass conditions under which hybridization will occur if there is less than 25% mismatch between the hybridization molecule and the target sequence. "Stringent conditions" can be further defined into particular levels of stringency. Thus, as used herein, "moderate stringency" conditions are those under which molecules with more than 25% mismatch will not hybridize. Conditions of "medium stringency" are those under which molecules with more than 15% mismatch will not hybridize, and conditions of "high stringency" are those under which sequence with more than 10% mismatch will not hybridize. Conditions of "very high stringency" are those under which sequences with more than 6% mismatch will not hybridize.

In particular embodiments, stringent conditions can include hybridization at 65° C., followed by sequential washes at 65° C. with 0.1×SSC/0.1% SDS for 40 minutes.

Isolated: An "isolated" biological component (such as a nucleic acid or protein) has been substantially separated, produced apart from, or purified away from other biological components in the cell of the organism in which the component naturally occurs, i.e., other chromosomal and extra-chromosomal DNA and RNA, and proteins. Nucleic acid molecules and proteins that have been "isolated" include nucleic acid molecules and proteins purified by standard purification methods. The term also embraces nucleic acids and proteins prepared by recombinant expression in a host cell, as well as chemically-synthesized nucleic acid molecules, proteins, and peptides.

Nucleic acid molecule: A polymeric form of nucleotides, which can include both sense and anti-sense strands of RNA, cDNA, genomic DNA, and synthetic forms and mixed polymers of the above. A nucleotide refers to a ribonucleotide, deoxynucleotide, or a modified form of either type of nucleotide. A "nucleic acid molecule" as used herein is synonymous with "nucleic acid" and "polynucleotide." The term includes single- and double-stranded forms of DNA. A nucleic acid molecule can include either or both naturally occurring and modified nucleotides linked together by naturally occurring and/or non-naturally occurring nucleotide linkages.

Nucleic acid molecules may be modified chemically or biochemically, or may contain non-natural or derivatized nucleotide bases, as will be readily appreciated by those of skill in the art. Such modifications include, for example, labels, methylation, and substitution of one or more of the naturally occurring nucleotides with an analog. Other modifications include internucleotide modifications, such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., peptides), intercalators (e.g., acridine, psoralen, etc.), chelators, alkylators, and modified linkages (e.g., alpha anomeric nucleic acids, etc.). The term "nucleic acid molecule" also includes any topological conformation, including single-stranded, double-stranded, partially duplexed, triplexed, hairpinned, circular, and padlocked conformations.

Operably linked: A first nucleic acid sequence is operably linked with a second nucleic acid sequence when the first nucleic acid sequence is in a functional relationship with the second nucleic acid sequence. For instance, a promoter is operably linked with a coding sequence when the promoter affects the transcription or expression of the coding sequence. When recombinantly produced, operably linked nucleic acid sequences are generally contiguous and, where necessary to join two protein-coding regions, in the same reading frame. However, elements need not be contiguous to be operably linked.

Promoter: A region of DNA that generally is located upstream (towards the 5' region of a gene) that is needed for transcription. Promoters permit the proper activation or repression of the gene which they control. A promoter contains specific sequences that are recognized by transcription factors. These factors bind to the promoter DNA sequences and result in the recruitment of RNA polymerase, the enzyme that synthesizes the RNA from the coding region of the gene. In some embodiments, tissue-specific promoters are used. A tissue-specific promoter is a DNA sequence that directs a higher level of transcription of an associated gene in the tissue for which the promoter is specific relative to the other tissues of the organism. Examples of tissue-specific promoters include tapetum-specific promoters; anther-specific promoters; pollen-specific promoters (See, e.g., U.S. Pat. No. 7,141,424, and International PCT Publication No. WO 99/042587); ovule-specific promoters; (See, e.g., U.S. Patent Application No. 2001/047525 A1); fruit-specific promoters (See, e.g., U.S. Pat. Nos. 4,943,674, and 5,753,475); and seed-specific promoters (See, e.g., U.S. Pat. Nos. 5,420,034, and 5,608,152). In some embodiments, developmental stage-specific promoters are also used, e.g., a promoter active at a later stage in development.

Transformed: A virus or vector "transforms" or "transduces" a cell when it transfers nucleic acid molecules into the cell. A cell is "transformed" by a nucleic acid molecule transduced into the cell when the nucleic acid molecule becomes stably replicated by the cell, either by incorporation of the nucleic acid molecule into the cellular genome or by episomal replication. As used herein, the term "transformation" encompasses all techniques by which a nucleic acid molecule can be introduced into such a cell. Examples include, but are not limited to, transfection with viral vectors, transformation with plasmid vectors, electroporation (Fromm et al. (1986) Nature 319:791-3), lipofection (Felgner et al. (1987) Proc. Natl. Acad. Sci. USA 84:7413-7), microinjection (Mueller et al. (1978) Cell 15:579-85), Agrobacterium-mediated transfer (Fraley et al. (1983) Proc. Natl. Acad. Sci. USA 80:4803-7), direct DNA uptake, and microprojectile bombardment (Klein et al. (1987) Nature 327:70).

Transgene: An exogenous nucleic acid sequence. In one example, a transgene is a gene sequence (e.g., an herbicide-resistance gene), a gene encoding an industrially or pharmaceutically useful compound, or a gene encoding a desirable agricultural trait. In yet another example, the transgene is an antisense nucleic acid sequence, wherein expression of the antisense nucleic acid sequence inhibits expression of a target nucleic acid sequence. A transgene may contain regulatory sequences operably linked to the transgene (e.g., a promoter). In some embodiments, a nucleic acid molecule of interest to be introduced by ELP-targeted recombination is a transgene. However, in other embodiments, a nucleic acid molecule of interest is an endogenous nucleic acid sequence, wherein additional genomic copies of the endogenous nucleic acid sequence are desired, or a nucleic acid molecule that is in the antisense orientation with respect to a target nucleic acid molecule in the host organism.

Vector: A nucleic acid molecule as introduced into a cell, thereby producing a transformed cell. A vector can include nucleic acid sequences that permit it to replicate in the host cell, such as an origin of replication. Examples include, but are not limited to, a plasmid, cosmid, bacteriophage, or virus that carries exogenous DNA into a cell. A vector can also include one or more genes, antisense molecules, and/or selectable marker genes and other genetic elements known in the art. A vector can transduce, transform, or infect a cell, thereby causing the cell to express the nucleic acid molecules and/or proteins encoded by the vector. A vector may optionally include materials to aid in achieving entry of the nucleic acid molecule into the cell (e.g., a liposome, protein coding, etc.).

IV. Engineered Landing Pads for Gene Targeting in Plants

A. Overview

In some embodiments, ELPs are introduced into plants, for example, to facilitate the introduction of one or more further nucleic acid molecule(s) of interest. The further nucleic acid molecule(s) of interest may comprise, for example, any nucleic acid sequence encoding a protein to be expressed in the host organism. In additional embodiments, ELPs are used to facilitate the introduction of nucleic acid molecules of unknown function to discern their function based on ectopic gene expression. Regions flanking the ELP(s) may be homologous to genomic nucleic acid sequence of the host plant, such that the ELP(s) are integrated into the host plant genome in a site-specific manner. ELPs can be used to incorporate nucleic acid molecules of various lengths.

In some embodiments, a nucleic acid molecule targeted to a transgenic ELP target may contain a second ELP to allow continued gene addition at the target site. One or more targeting endonucleases (e.g., ZFNs) may be used sequentially or simultaneously in this process. If desired, more than one targeting endonuclease binding site (e.g., ZFN binding site) may additionally be incorporated internal to regions of the ELP(s) that are homologous to genomic nucleic acid sequence of the host plant. In some embodiments, targeting endonuclease binding sites may be added so that they flank the ELPs. In this latter and further embodiments, expression of a targeting endonuclease (e.g., ZFN) that cleaves at the added binding sites in the plant leads to excision of the ELPs.

In some embodiments, regions homologous to genomic nucleic acid sequence of the host plant may also be used in combination with other flanking DNAs to allow insertion of nucleic acid molecules adjacent to a nucleic acid molecule of interest introduced at an ELP target, such as, for example, a gene expression element or gene of interest. DNA cleavage may be used to enhance homologous recombination at this site. In some embodiments, regions of homology in ELPs that are homologous to genomic nucleic acid sequence may also be used for targeted insertion of nucleic acid molecules that is facilitated by enzymes that cleave DNA, such as ZFNs, meganucleases or other targeting endonucleases.

In some embodiments, ELPs may be incorporated into modified chromosomal regions, such as may be generated by the DNA amplification processes or in minichromosomes. In some embodiments, regions of homology and appropriately placed targeting endonucleases (e.g., ZFNs) are used to facilitate modification of sequences internal to the flanking regions homologous to genomic nucleic acid sequence of the host plant.

B. Design of ELPs

In some embodiments, ELPs may be designed to facilitate homologous recombination in plant chromosomal locations. ELPs may have a neutral impact on surrounding genes or DNA sequences. ELPs may represent unique, targetable sequences within the plant genome. In certain embodiments, the size (e.g., 1 kb) for each 5' and 3' region of homology to a desired chromosomal location is selected to meet the minimal size considered desirable for facilitating homology-directed recombination. In specific embodiments, the size for each 5' and 3' region of homology is about 50 bp; 100 bp; 200 bp; 400 bp; 600 bp; 700 bp; 750 bp; 800 bp; 1 kb; 1.2 kb; 1.4 kb; 1.6 kb; 1.8 kb; 2 kb; or 3 kb. The 5' and 3' regions of homology are not required to be the same sizes in particular embodiments. ELP sequences may be produced, for example, using a computer program for random number generation. ELP sequences produced, for example, by random sequence generation may then be selected for use as ELPs based on desirable characteristics, including but not limited to sequences substantially or completely lacking homology to native genomic sequences of the target organism. Selected ELPs may also be modified as further detailed below.

In some embodiments, criteria for designing ELPs and/or modifying selected ELPs may include one or more of the following: removal of restriction sites used routinely for cloning; reduction in the number of potential methylation sites (e.g., CG and CNG); and absence of any open reading frame greater than 300 bp. Additionally, during the design of ELPs, other sites in nucleic acid sequences may be removed, including, for example: exon:intron junctions (5' or 3'); poly A addition signals; RNA polymerase termination signals; and highly stable intrastrand secondary structures. Sequences may also be analyzed and modified to reduce the frequency of TA or CG doublets. Sequence blocks that have more than about six consecutive residues of [G+C] or [A+T] may also be removed from a sequence during ELP design.

In embodiments, ELPs may include, for example, nucleotide sequences of the formula $X_1$-Y-$X_2$, wherein Y is at least one targeting endonuclease binding site (e.g., a ZFN binding site), wherein $X_1$ is a selected nucleotide sequence lacking homology with the genome of the host organism and positioned 5' of Y, and wherein $X_2$ is a selected nucleotide sequence lacking homology with the genome of the host organism that is different from $X_1$.

Exemplary $X_1$ and $X_2$ nucleotide sequences may be independently selected from the following sequences: SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; and SEQ ID NO: 10. Additional modifications, deletions, or additions to these sequences (e.g., removal or addition of restriction sites) may be made in some embodiments to provide for added or different functionality. For example, in certain embodiments: SEQ ID NO: 1 may be modified to generate SEQ ID NO: 11; SEQ ID NO: 3 may be modified to generate SEQ ID NO: 12; SEQ ID NO: 2 may be modified to generate SEQ ID NO: 13; SEQ ID NO: 4 may be modified to generate SEQ ID NO: 14; SEQ ID NO: 5 may be modified to generate SEQ ID NO: 17; and SEQ ID NO: 6 may be modified to generate SEQ ID NO: 18.

In particular embodiments, exemplary ELPs include, but are not limited to the following sequences: SEQ ID NO: 15; SEQ ID NO: 16; and SEQ ID NO: 19.

Restriction enzyme sites (e.g., FseI restriction enzyme sites) may be introduced flanking an ELP to enable cloning of the ELP into an appropriate vector. Restriction enzyme sites may also be introduced flanking an ELP that produce compatible ends upon restriction enzyme digestion (e.g., BglII and BamHI sites), to allow chaining of the ELPs together, for example, as a concatemer, in the host plant genome. Restriction enzyme sites may also be introduced to allow analysis in the host plant of nucleic acid sequences of interest subsequently targeted to the ELPs by recombination. Two or more restriction enzyme sites may be introduced flanking a single ELP. For example, BglII and BamHI sites may be included internal to FseI sites. Restriction enzyme sites may also be introduced to allow analysis in the host plant of nucleic acid sequences of interest targeted to the ELP for insertion by recombination. For example, PmeI sites may be introduced to flank the insertion site.

C. Delivery of Nucleic Acid Molecules into Plant Cells Containing an ELP

In order to enable targeting endonuclease-mediated integration of a nucleic acid molecule of interest (e.g., ELP(s) and/or exogenous nucleic acid molecules targeted to a previously integrated ELP) into a plant genome via targeted integration, delivery of targeting endonucleases or targeting endonuclease-encoding nucleic acid molecules followed by expression of a functional targeting endonuclease protein in the plant cell is required. A nucleic acid molecule of interest should also be present in the plant cell at the same time as the targeting endonuclease is delivered or expressed therein, such that functional targeting endonuclease protein may induce double-stranded breaks at the target site(s) which are then repaired via homology-driven integration of the nucleic acid molecule of interest into the target locus. One skilled in the art may envision that expression of functional targeting endonuclease protein may be achieved by several methods, including, but not limited to, transgenesis of a targeting endonuclease-encoding construct, or transient expression of a targeting endonuclease-encoding construct. In both these cases, expression of functional targeting endonuclease protein and delivery of donor DNA in the plant cell may be simultaneously achieved in order to drive targeted integration.

Thus, in particular embodiments, targeting endonucleases (e.g., ZFNs) are expressed from nucleic acid molecules in transformed plants to introduce double-stranded breaks in the genome of transformed plants, e.g., in one or more ELPs previously introduced to the plant. Targeting endonucleases may be used that target one or more recognition sequence(s) designed to be present in ELPs. Design and selection approaches for constructing an ELP of the invention may therefore begin by determining one or more specific nucleic acid sequence(s) that are recognized by targeting endonuclease(s) to be used subsequently to introduce a nucleic acid molecule of interest at the ELP. The flexibility and specificity of the ZFN system provides a level of control previously unachievable by known recombinase-mediated gene excision strategies.

As one example, ZFNs can be easily engineered, for example, to recognize specific nucleic acid sequences (e.g., ELPs). Wu et al. (2007) Cell. Mol. Life. Sci. 64:2933-44. Randomization of the codons for zinc finger recognition residues allows the selection of new fingers that have high affinity for arbitrarily chosen DNA sequences. Furthermore, zinc fingers are natural DNA-binding molecules, and engineered zinc fingers have been shown to act on their designed targets in living cells. Thus, nucleases based on zinc fingers are targetable to specific but arbitrary recognition sites.

The requirement for dimerization of cleavage domains of chimeric zinc finger nucleases imparts a high level of sequence specificity. Since each set of three fingers binds nine consecutive base pairs, two chimeric nucleases effectively demand an 18 bp target if each zinc finger domain has perfect specificity. Any given sequence of this length is predicted to be unique within a single genome (assuming approximately $10^9$ bp). Bibikova et al. (2001) Mol. Cell. Biol. 21(1):289-97; Wu et al. (2007), supra. Furthermore, additional fingers provide enhanced specificity, Beerli et al. (1998) Proc. Natl. Acad. Sci. USA 95:14628-33; Kim and Pabo (1998) Proc. Natl. Acad. Sci. USA 95:2812-7; Liu et al. (1997) Proc. Natl. Acad. Sci. USA 94:5525-30, so the number of zinc fingers in each DNA-binding domain may be increased to provide even further specificity. For example, specificity may be further increased by using a pair of 4-finger ZFNs that recognize a 24 bp sequence. Urnov et al. (2005) Nature 435:646-51. Thus, ZFNs may be used such that a recognition sequence in an ELP introduced into the host plant genome is unique within the genome.

A nucleic acid molecule of interest that is introduced by targeted recombination at an ELP may be operably linked to one or more plant promoter(s) driving expression of the gene in an amount sufficient to confer a desired trait or phenotype. Promoters suitable for this and other uses are well known in the art. Non-limiting examples describing such promoters include U.S. Pat. No. 6,437,217 (maize RS81 promoter); U.S. Pat. No. 5,641,876 (rice actin promoter); U.S. Pat. No. 6,426,446 (maize RS324 promoter); U.S. Pat. No. 6,429,362 (maize PR-1 promoter); U.S. Pat. No. 6,232,526 (maize A3 promoter); U.S. Pat. No. 6,177,611 (constitutive maize promoters); U.S. Pat. Nos. 5,322,938, 5,352,605, 5,359,142, and 5,530,196 (35S promoter); U.S. Pat. No. 6,433,252 (maize L3 oleosin promoter); U.S. Pat. No. 6,429,357 (rice actin 2 promoter, and rice actin 2 intron); U.S. Pat. No. 5,837,848 (root-specific promoter); U.S. Pat. No. 6,294,714 (light-inducible promoters); U.S. Pat. No. 6,140,078 (salt-inducible promoters); U.S. Pat. No. 6,252,138 (pathogen-inducible promoters); U.S. Pat. No. 6,175,060 (phosphorous deficiency-inducible promoters); U.S. Pat. No. 6,388,170 (bidirectional promoters); U.S. Pat. No. 6,635,806 (gamma-coixin promoter); and U.S. patent application Ser. No. 09/757,089 (maize chloroplast aldolase promoter). Additional promoters include the nopaline synthase (NOS) promoter (Ebert et al. (1987) Proc. Natl. Acad. Sci. USA 84(16):5745-9); the octopine synthase (OCS) promoter (which is carried on tumor-inducing plasmids of *Agrobacterium tumefaciens*); the caulimovirus promoters such as the cauliflower mosaic virus (CaMV) 19S promoter (Lawton et al. (1987) Plant Mol. Biol. 9:315-24); the CaMV 35S promoter (Odell et al. (1985) Nature 313:810-2; the figwort mosaic virus 35S-promoter (Walker et al. (1987) Proc. Natl. Acad. Sci. USA 84(19): 6624-8); the sucrose synthase promoter (Yang and Russell (1990) Proc. Natl. Acad. Sci. USA 87:4144-8); the R gene complex promoter (Chandler et al. (1989) Plant Cell 1:1175-83); the chlorophyll a/b binding protein gene promoter; CaMV35S (U.S. Pat. Nos. 5,322,938, 5,352,605, 5,359,142, and 5,530,196); FMV35S (U.S. Pat. Nos. 6,051,753, and 5,378,619); a PC1SV promoter (U.S. Pat. No. 5,850,019); the SCP1 promoter (U.S. Pat. No. 6,677,503); and AGRtu.nos promoters (GenBank Accession No. V00087; Depicker et al. (1982) J. Mol. Appl. Genet. 1:561-73; Bevan et al. (1983) Nature 304:184-7), and the like.

Additional genetic elements that may optionally be operably linked to a nucleic acid molecule of interest include sequences coding for transit peptides. For example, incorporation of a suitable chloroplast transit peptide, such as the *A. thaliana* EPSPS CTP (Klee et al. (1987) Mol. Gen. Genet. 210:437-42), and the *Petunia hybrida* EPSPS CTP (della-Cioppa et al. (1986) Proc. Natl. Acad. Sci. USA 83:6873-7) has been shown to target heterologous EPSPS protein sequences to chloroplasts in transgenic plants. Dicamba monooxygenase (DMO) may also be targeted to chloroplasts, as described in International PCT Publication No. WO 2008/105890.

Additional genetic elements that may optionally be operably linked to a nucleic acid molecule of interest also include 5' UTRs located between a promoter sequence and a coding sequence that function as a translation leader sequence. The translation leader sequence is present in the fully processed mRNA upstream of the translation start sequence. The translation leader sequence may affect processing of the primary transcript to mRNA, mRNA stability, and/or translation efficiency. Examples of translation leader sequences include maize and petunia heat shock protein leaders (U.S. Pat. No. 5,362,865), plant virus coat protein leaders, plant rubisco leaders, and others. See, e.g., Turner and Foster (1995) Molecular Biotech. 3(3):225-36. Non-limiting examples of 5' UTRs include GmHsp (U.S. Pat. No. 5,659,122); PhDnaK (U.S. Pat. No. 5,362,865); AtAnt1; TEV (Carrington and Freed (1990) J. Virol. 64:1590-7); and AGRtunos (GenBank Accession No. V00087; and Bevan et al. (1983) Nature 304: 184-7).

Additional genetic elements that may optionally be operably linked to a nucleic acid molecule of interest also include 3' non-translated sequences, 3' transcription termination regions, or poly-adenylation regions. These are genetic elements located downstream of a polynucleotide molecule, and include polynucleotides that provide polyadenylation signal, and/or other regulatory signals capable of affecting transcription, mRNA processing, or gene expression. The polyadenylation signal functions in plants to cause the addition of polyadenylate nucleotides to the 3' end of the mRNA precursor. The polyadenylation sequence can be derived from the natural gene, from a variety of plant genes, or from T-DNA genes. A non-limiting example of a 3' transcription termination region is the nopaline synthase 3' region (nos 3'; Fraley et al. (1983) Proc. Natl. Acad. Sci. USA 80:4803-7). An example of the use of different 3' nontranslated regions is provided in Ingelbrecht et al., (1989) Plant Cell 1:671-80. Non-limiting examples of polyadenylation signals include one from a

*Pisum sativum* RbcS2 gene (Ps.RbcS2-E9; Coruzzi et al. (1984) EMBO J. 3:1671-9) and AGRtu.nos (GenBank Accession No. E01312).

D. Transformation of Host Cells with Nucleic Acid Molecules

Any of the techniques known in the art for introduction of nucleic acid molecules into plants may be used to produce a transformed plant according to the invention, for example, to introduce one or more ELPs into the host plant genome, and/or to further introduce a nucleic acid molecule of interest. Suitable methods for transformation of plants include any method by which DNA can be introduced into a cell, such as: by electroporation, as illustrated in U.S. Pat. No. 5,384,253; by microprojectile bombardment, as illustrated in U.S. Pat. Nos. 5,015,580, 5,550,318, 5,538,880, 6,160,208, 6,399,861, and 6,403,865; by *Agrobacterium*-mediated transformation as illustrated in U.S. Pat. Nos. 5,635,055, 5,824,877, 5,591,616; 5,981,840, and 6,384,301; and by protoplast transformation, as set forth in U.S. Pat. No. 5,508,184. Through the application of techniques such as these, the cells of virtually any plant species may be stably transformed, and these cells may be developed into transgenic plants by techniques known to those of skill in the art. For example, techniques that may be particularly useful in the context of cotton transformation are disclosed in U.S. Pat. Nos. 5,846,797, 5,159,135, 5,004,863, and 6,624,344; techniques for transforming *Brassica* plants in particular are disclosed, for example, in U.S. Pat. No. 5,750,871; techniques for transforming soybean are disclosed, for example, in U.S. Pat. No. 6,384,301; and techniques for transforming corn are disclosed, for example, in U.S. Pat. No. 7,060,876, U.S. Pat. No. 5,591,616, and International PCT Publication WO 95/06722.

After effecting delivery of exogenous DNA to recipient cells, transformed cells are generally identified for further culturing and plant regeneration. In order to improve the ability to identify transformants, one may desire to employ a selectable or screenable marker gene with the transformation vector used to generate the transformant. In this case, the potentially transformed cell population can be assayed by exposing the cells to a selective agent or agents, or the cells can be screened for the desired marker gene trait.

Cells that survive the exposure to the selective agent, or cells that have been scored positive in a screening assay, may be cultured in media that supports regeneration of plants. In some embodiments, any suitable plant tissue culture media (e.g., MS and N6 media) may be modified by including further substances, such as growth regulators. Tissue may be maintained on a basic media with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturity.

To confirm the presence of a nucleic acid molecule of interest in the regenerating plants, a variety of assays may be performed. Such assays include, for example: molecular biological assays, such as Southern and Northern blotting and PCR; biochemical assays, such as detecting the presence of a protein product, e.g., by immunological means (ELISA and/ or Western blots) or by enzymatic function; plant part assays, such as leaf or root assays; and analysis of the phenotype of the whole regenerated plant.

Targeted integration events may be screened, for example, by PCR amplification using, e.g., oligonucleotide primers specific for nucleic acid molecules of interest. PCR genotyping is understood to include, but not be limited to, polymerase-chain reaction (PCR) amplification of genomic DNA derived from isolated host plant callus tissue predicted to contain a nucleic acid molecule of interest integrated into the genome, followed by standard cloning and sequence analysis of PCR amplification products. Methods of PCR genotyping have been well described (for example, Rios, G. et al. (2002) Plant J. 32:243-53) and may be applied to genomic DNA derived from any plant species or tissue type, including cell cultures. Combinations of oligonucleotide primers that bind to both target sequence and introduced sequence may be used sequentially or multi-plexed in PCR amplification reactions. Oligonucleotide primers designed to anneal to the target site, introduced nucleic acid sequences, and/or combinations of the two are feasible. Thus, PCR genotyping strategies may include (but are not limited to) amplification of specific sequences in the plant genome, amplification of multiple specific sequences in the plant genome, amplification of non-specific sequences in the plant genome, or combinations thereof. One skilled in the art may devise additional combinations of primers and amplification reactions to interrogate the genome. For example, a set of forward and reverse oligonucleotide primers may be designed to anneal to nucleic acid sequence(s) specific for the target outside the boundaries of the introduced nucleic acid sequence.

Forward and reverse oligonucleotide primers may be designed to anneal specifically to an introduced nucleic acid molecule of interest, for example, at a sequence corresponding to a coding region within the nucleic acid molecule of interest, or other parts of the nucleic acid molecule of interest. These primers may be used in conjunction with the primers described above. Oligonucleotide primers may be synthesized according to a desired sequence, and are commercially available (e.g., from Integrated DNA Technologies, Inc., Coralville, Iowa). Amplification may be followed by cloning and sequencing, or by direct sequence analysis of amplification products. One skilled in the art might envision alternative methods for analysis of amplification products generated during PCR genotyping. In one embodiment, oligonucleotide primers specific for the gene target are employed in PCR amplifications.

E. Cultivation and Use of Transgenic Plants

A transgenic plant comprising one or more ELPs and/or nucleic acid molecule of interest, inserted by targeted recombination at the ELP site according to the present invention, may have one or more desirable traits. Such traits can include, for example: resistance to insects, other pests, and disease-causing agents; tolerances to herbicides; enhanced stability, yield, or shelf-life; environmental tolerances; pharmaceutical production; industrial product production; and nutritional enhancements. The desirable traits may be conferred by one or more nucleic acid molecules inserted by targeted recombination at an ELP site that are expressed in the plant exhibiting the desirable traits. Thus, in some embodiments, the desired trait can be due to the presence of a transgene(s) in the plant, which is introduced into the genome of the plant at the site of an ELP. In an additional embodiment, the desirable trait can be obtained through conventional breeding, which trait may be conferred by one or more nucleic acid molecules inserted by targeted recombination at an ELP site.

A transgenic plant according to the invention may be any plant capable of being transformed with a nucleic acid molecule of the invention. Accordingly, the plant may be a dicot or monocot. Non-limiting examples of dicotyledonous plants usable in the present methods include alfalfa, beans, broccoli, cabbage, carrot, cauliflower, celery, Chinese cabbage, cotton, cucumber, eggplant, lettuce, melon, pea, pepper, peanut, potato, pumpkin, radish, rapeseed, spinach, soybean, squash, sugarbeet, sunflower, tobacco, tomato, and watermelon. Non-limiting examples of monocotyledonous plants usable in the present methods include corn, onion, rice, sorghum, wheat, rye, millet, sugarcane, oat, triticale, switchgrass, and turfgrass.

Transgenic plants according to the invention may be used or cultivated in any manner, wherein presence the ELP(s) and/or nucleic acid molecules of interest is desirable. Accordingly, may be engineered to, inter alia, have one or more desired traits, by being transformed with nucleic acid molecules according to the invention, and cropped and cultivated by any method known to those of skill in the art.

EXAMPLES

The following examples are included to illustrate embodiments of the invention. It will be appreciated by those of skill in the art that the techniques disclosed in the Examples represent techniques discovered by the inventors to function well in the practice of the invention. However, those of skill in the art, in light of the present disclosure, will appreciate that many changes can be made in the specific embodiments which are disclosed and still obtain a like or similar result without departing from the scope of the invention. More specifically, it will be apparent that certain agents which are both chemically and physiologically related may be substituted for the agents described herein, while the same or similar results would be achieved. All such similar substitutes and modifications apparent to those skilled in the art are deemed to be within the scope of the invention as defined by the appended Claims.

Example 1

Vector Construction

Two different ELPs were synthesized that consisted of a 1 kbp 5' region of homology ("engineered landing pad region 1" (SEQ ID NO: 11) in pDAB100610/pDAB100640 and "engineered synthetic homology region 3" (SEQ ID NO: 12) in pDAB100611/pDAB100641) and a 1 kbp 3' region of homology ("engineered landing pad region 2" (SEQ ID NO: 13) in pDAB100610 and "engineered synthetic homology region 4" (SEQ ID NO: 14) in pDAB100611/pDAB100641). These regions of homology were separated by two different EXZACT Zinc Finger Nuclease (eZFN) binding sites.

The two ELPs used for pDAB100610 and pDAB100611, designated ELP1 (SEQ ID NO: 15) and ELP2 (SEQ ID NO: 16), respectively, were transferred using the GATEWAY® LR clonase reaction (Invitrogen, Carlsbad, Calif.) into pDAB100704, a destination superbinary vector which is derived from pSB11 (WO94/00977 and WO95/06722). pDAB100704 contains the ZmUbi1 promoter (promoter, 5' untranslated region (UTR) and intron derived from the Zea mays ubiquitin 1 promoter (Christensen et al., (1992) Plant Molecular Biology, 18(4); 675-89)), the AAD-1 selectable marker gene (a synthetic, plant-optimized version of an aryloxyalkanoate dioxygenase gene from Sphingobium herbicidovorans (ATCC® 700291) encoding an enzyme with an alpha ketoglutarate-dependent dioxygenase activity that confers resistance to aryloxyphenoxypropionate herbicides (WO 2005/107437, WO 2008/141154A2, and US 2009/0093366, each of which is incorporated herein by reference), and the ZmLip 3' UTR (3' untranslated region (UTR) comprising the transcriptional terminator and polyadenylation site of the Zea mays LIP gene; GenBank accession L35913).

The two ELPs used for pDAB100640 and pDAB100641, designated ELP1 (SEQ ID NO: 15) and ELP2 (SEQ ID NO: 16), respectively, were transferred using the GATEWAY® LR clonase reaction (Invitrogen, Carlsbad, Calif.) into pDAB101849, a binary vector, pDAB101849 contains the OsAct1 promoter (promoter, and intron derived from the rice actin promoter (U.S. Pat. No. 5,641,876)), the pat selectable marker gene (phosphinothricin acetyl transferase gene; Wohlleben et al., (1988) Gene 70:25-37), and the ZmLip 3' UTR (3' untranslated region (UTR) comprising the transcriptional terminator and polyadenylation site of the Zea mays LIP gene; GenBank accession L35913).

Figure 2:
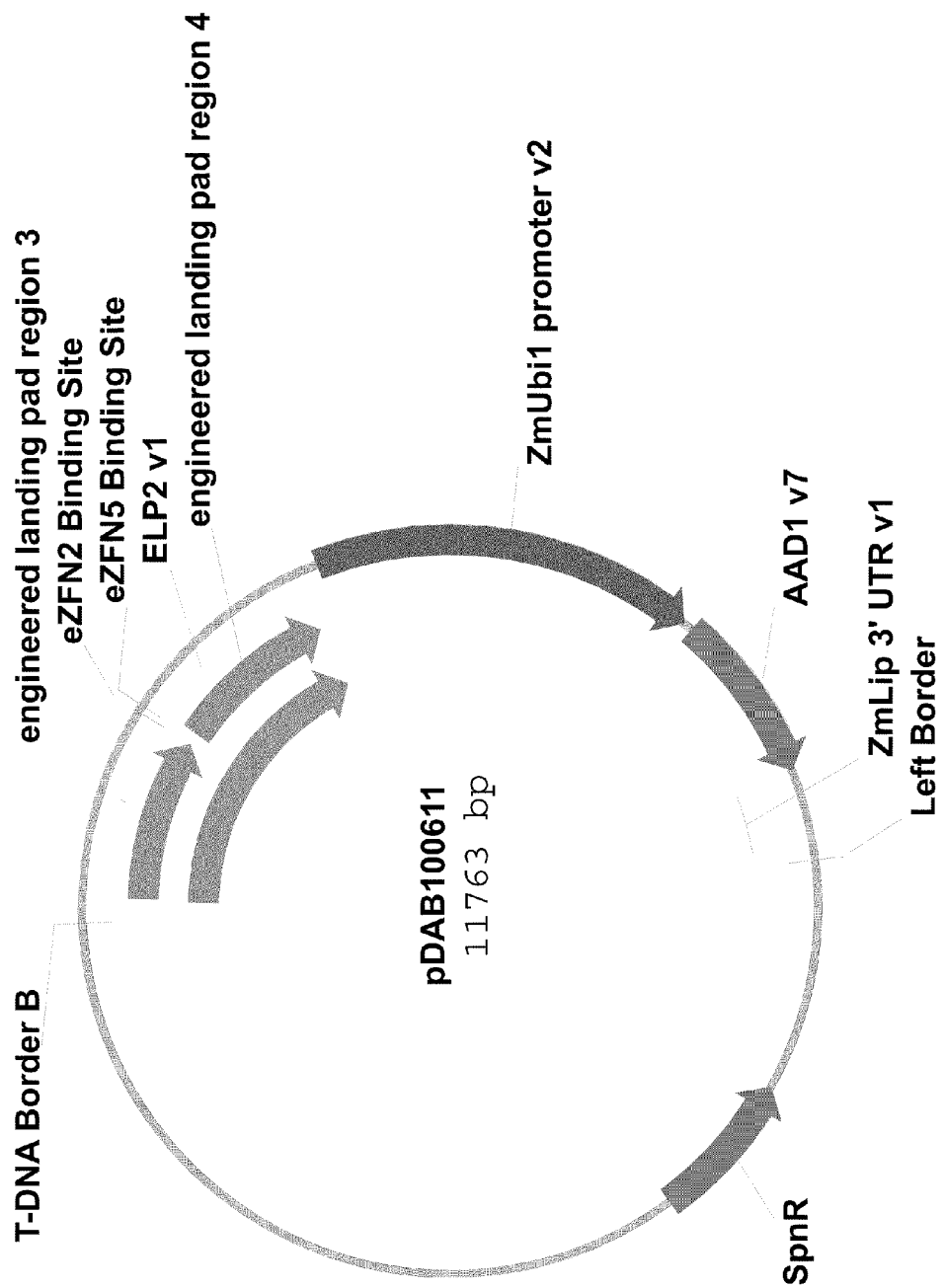
FIG. 2 includes a depiction of a representative vector comprising an ELP, pDAB100611.
Figure 3:
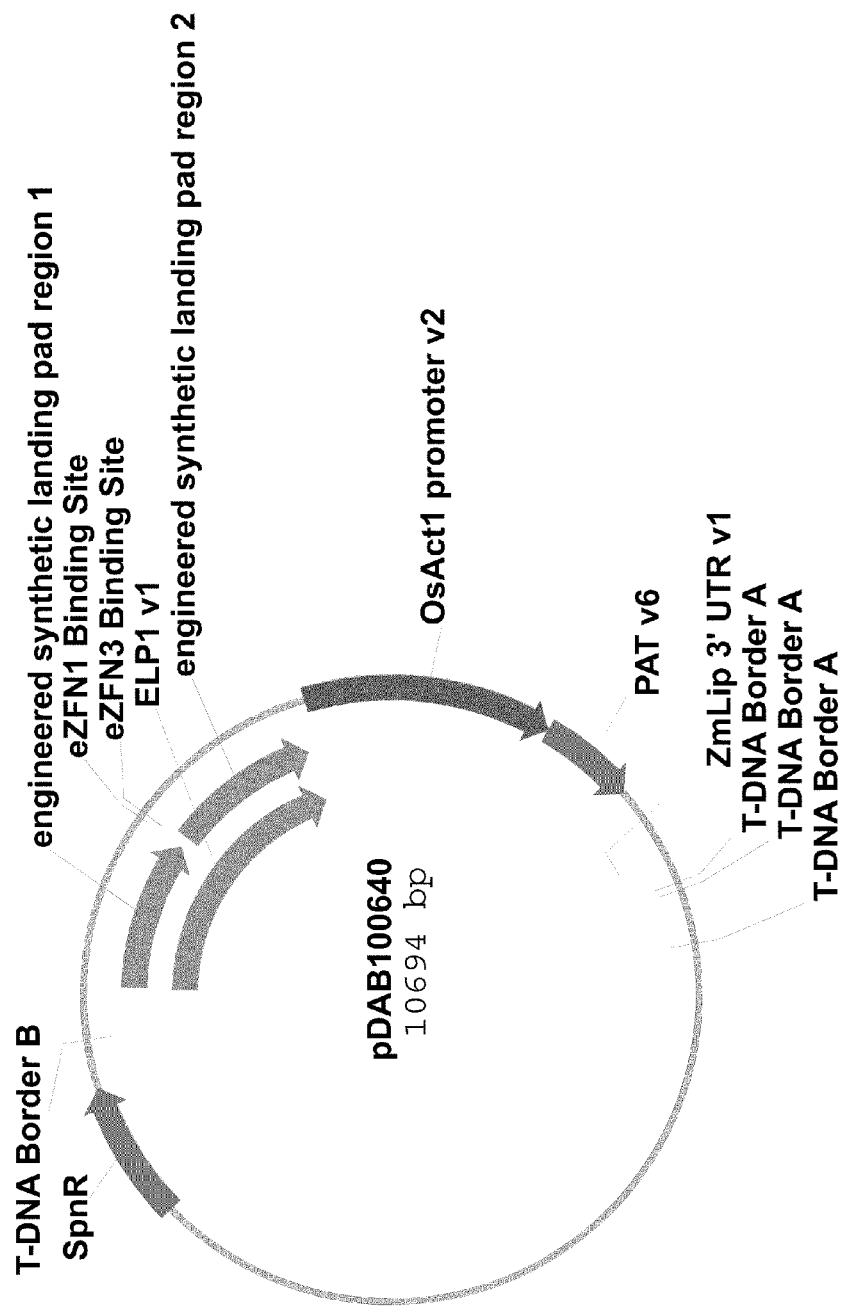
FIG. 3 includes a depiction of a representative vector comprising an ELP, pDAB100640
Figure 4:
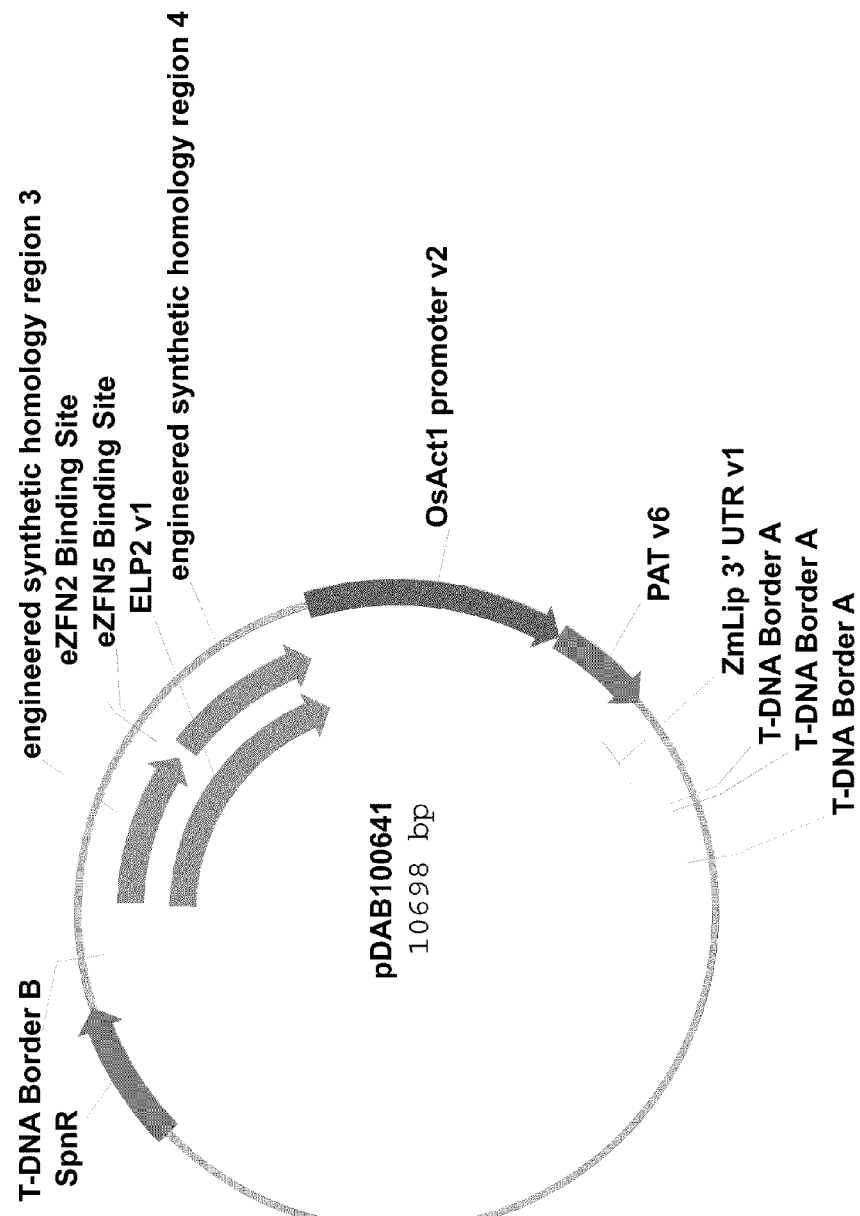
FIG. 4 includes a depiction of a representative vector comprising an ELP, pDAB100641

The resultant clones, pDAB100610 (FIG. 1), pDAB100611 (FIG. 2), pDAB100640 (FIG. 3), and pDAB100641 (FIG. 4) were sequence verified. The pDAB100610 and pDAB100611 vectors were transferred into an *Agrobacterium tumefaciens* strain LBA4404 harboring the pSB1 binary plasmid, and the T-strand region was integrated into pSB1 via homolgous recombination. The pDAB100640 and pDAB100641 vectors were transferred into *Agrobacterium tumefaciens* strain LBA4404. The structure of each plasmid was confirmed by restriction enzyme digestion.

Vectors containing nucleic acid molecules of interest (donor DNA) were assembled by inserting a YFP expression cassette and either the PAT or AAD-1 expression cassette in-between truncated versions of the 5' and 3' regions of homology (noted as versions 2 (v2)) for ELP1 and ELP2. The PAT expression cassette contains the OsAct1 promoter (rice actin1 promoter; McElroy et al., (1990) Plant Cell 2:163-171) which was used to express a pat gene (phosphinothricin acetyl transferase gene; Wohlleben et al., (1988) Gene 70:25-37) that is flanked by a ZmLip 3' untranslated region. The AAD-1 expression cassette contains the ZmUbi 1 promoter to drive the aad-1 gene and the ZmPer 5 3'UTR (U.S. Pat. No. 6,384,207). The YFP expression cassette consists of the ZmUbi1 promoter which is used to drive expression of the PhiYFP gene (yellow fluorescent protein (US PAT App. US2007/0298412)) and is flanked by the ZmPer5 3'UTR (U.S. Pat. No. 6,384,207).

Figure 5:
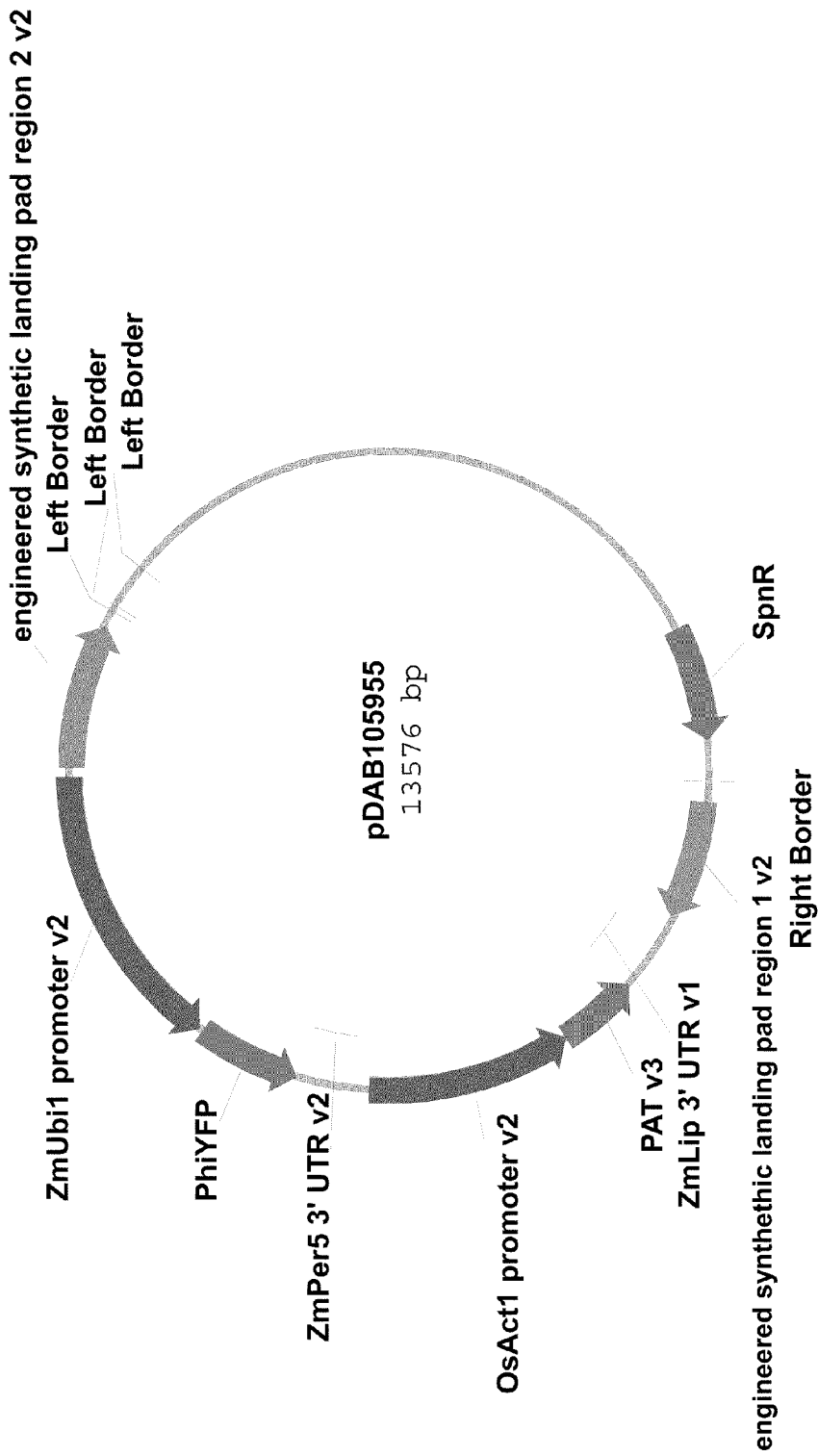
FIG. 5 includes a depiction of a representative vector comprising a donor fragment to be integrated into an ELP, pDAB105955.
Figure 6:
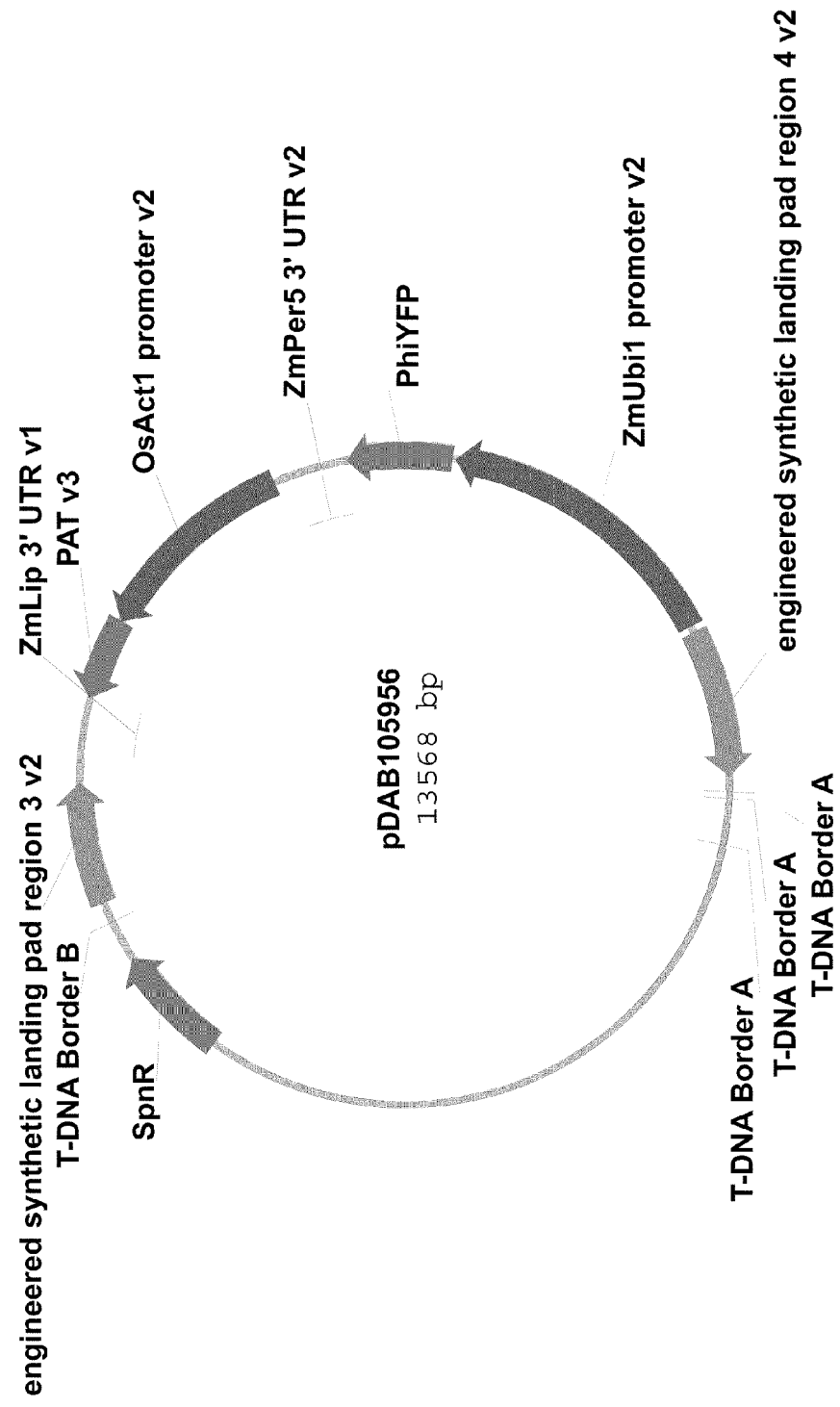
FIG. 6 includes a depiction of a representative vector comprising a donor fragment to be integrated into an ELP, pDAB105956.
Figure 7:
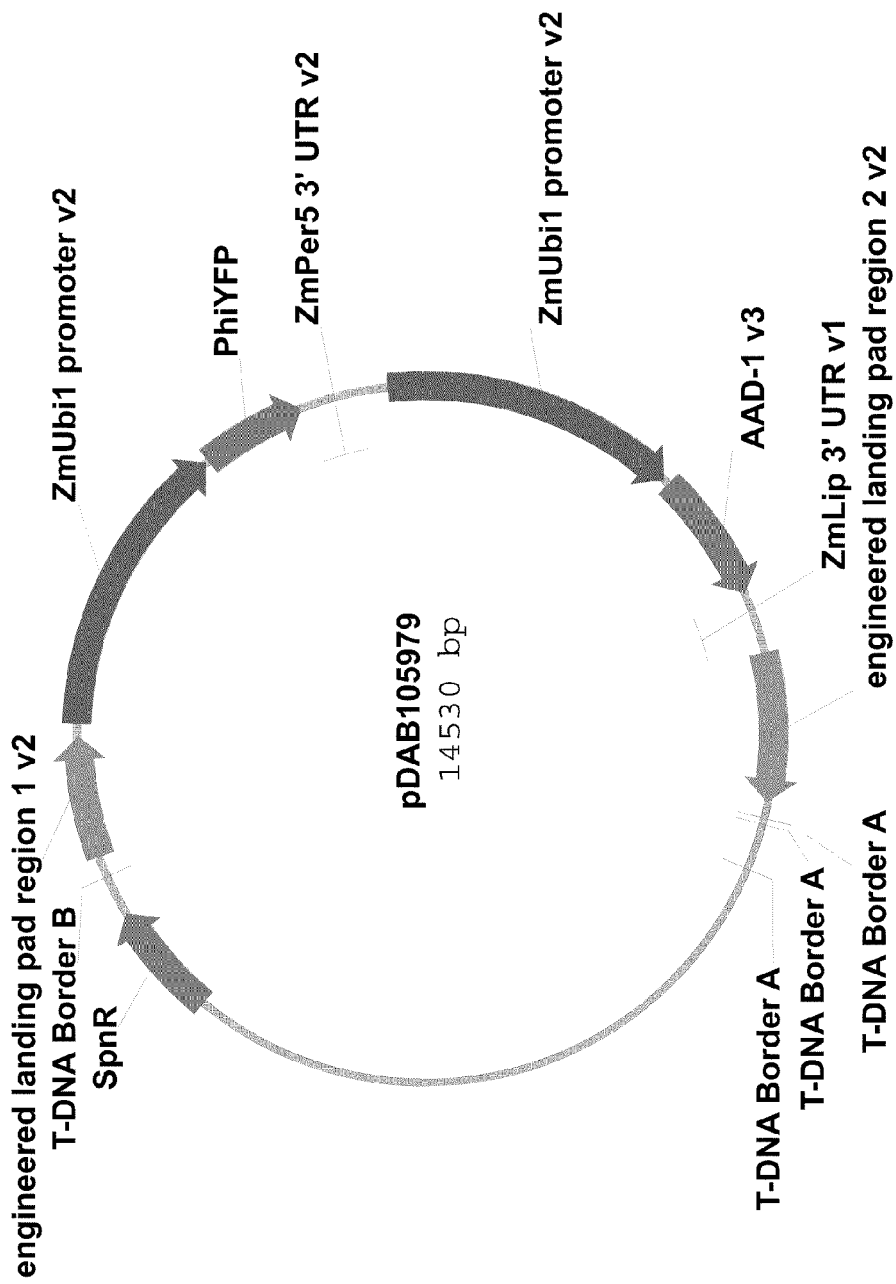
FIG. 7 includes a depiction of a representative vector comprising a donor fragment to be integrated into an ELP, pDAB105979.
Figure 8:
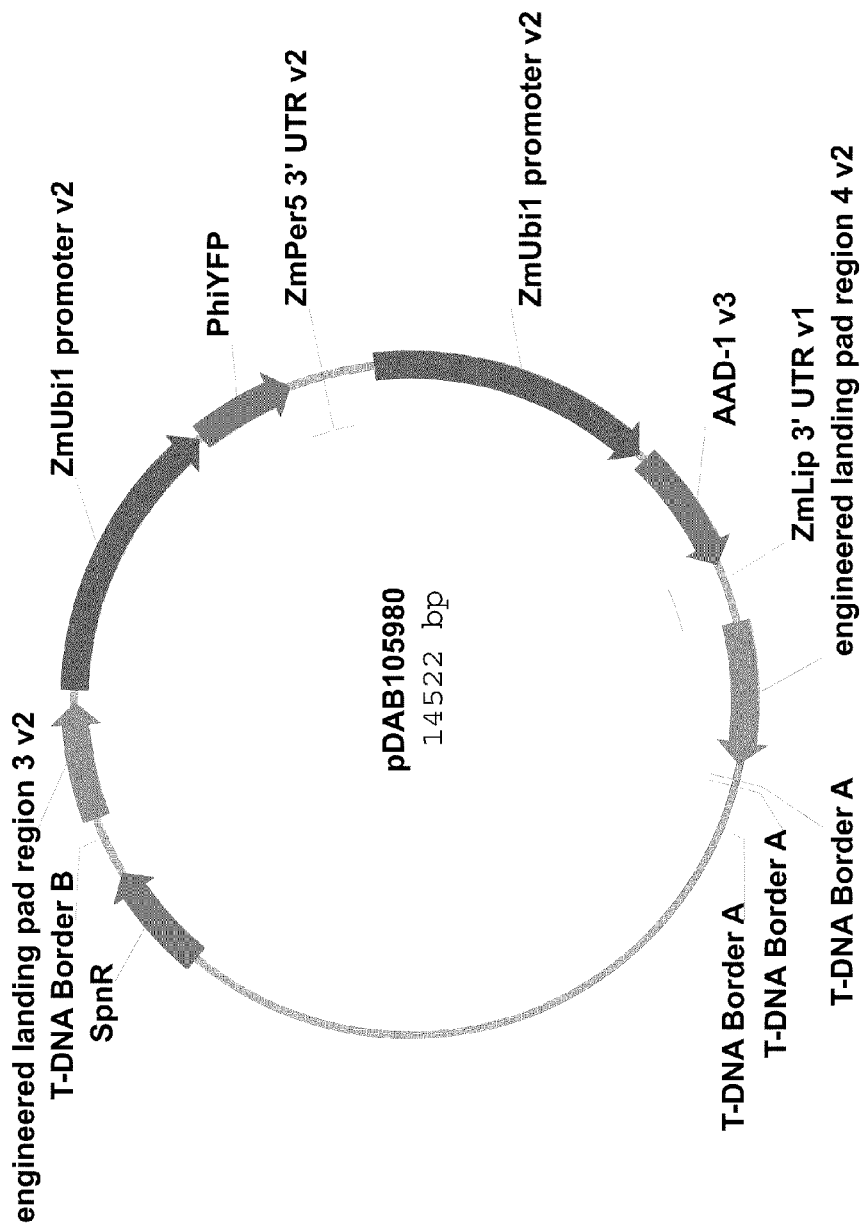
FIG. 8 includes a depiction of a representative vector comprising a donor fragment to be integrated into an ELP, pDAB105980.

The PAT and YFP expression cassettes were cloned between truncated versions of "engineered landing pad region 1" and "engineered landing pad region 2" in ELP1 (pDAB105955, FIG. 5). Alternatively, the PAT and YFP expression cassettes were cloned between truncated versions of "engineered homology region 3" and "engineered homology region 4" in ELP2 (pDAB105956, FIG. 6). Likewise, the AAD-1 and YFP expression cassettes were cloned between truncated versions of "engineered landing pad region 1" and truncated versions of "engineered landing pad region 2" in ELP1 (pDAB105979, FIG. 7). Alternatively, the AAD-1 and YFP expression cassettes were cloned between truncated versions of "engineered homology region 3" and truncated versions of "engineered homology region 4" in ELP2 (pDAB105980, FIG. 8). The donor DNA constructs were cloned into a binary vector for Biolistic, WHISKERS or *Agrobacterium*-mediated transformation. In addition, the DNA constructs can be cloned into a high-copy number plasmid (e.g., pBR322 derivatives bearing a ColE1 origin of replication) for generation of plasmid DNA used for direct DNA delivery transformation.

Example 2

Whiskers-Mediated DNA Delivery

Embryogenic Hi-II cell cultures of maize were produced as described in U.S. Pat. No. 7,179,902, and were used as the source of living plant cells in which targeted integration was exemplified.

Fragments containing the AAD-1 plant selectable marker cassette and the ELP1 and ELP2, respectively, from pDAB100610 and pDAB100611 and fragments containing the PAT plant selectable marker cassette and the ELP1 and ELP2, respectively, from pDAB100640 and pDAB100641 were used to generate transgenic events. Transgenic events were isolated and characterized. These events were then targeted using homology-directed homologous recombination, wherein a nucleic acid molecule of interest can be integrated within the engineered landing pad.

12 mL of packed cell volume (PCV) from a previously cryo-preserved cell line plus 28 mL of conditioned medium was subcultured into 80 mL of GN6 liquid medium (N6 medium (Chu et al., (1975) Sci Sin. 18:659-668), 2.0 mg/L 2,4-D, 30 g/L sucrose, pH 5.8) in a 500 mL Erlenmeyer flask, and placed on a shaker at 125 rpm at 28° C. This step was repeated two times using the same cell line, such that a total of 36 mL PCV was distributed across three flasks. After 24 hrs, the GN6 liquid media was removed and replaced with 72 mL GN6 S/M osmotic medium (N6 Medium, 2.0 mg/L 2,4-D, 30 g/L sucrose, 45.5 g/L sorbitol, 45.5 g/L mannitol, 100 mg/L myo-inositol, pH 6.0). The flask was incubated in the dark for 30-35 minutes at 28° C. with moderate agitation (125 rpm). During the incubation period, a 50 mg/mL suspension of silicon carbide whiskers (Advanced Composite Materials, LLC, Greer, S.C.) was prepared by adding 8.1 mL of GN6 S/M liquid medium to 405 mg of sterile, silicon carbide whiskers.

Following incubation in GN6 S/M osmotic medium, the contents of each flask were pooled into a 250 mL centrifuge bottle. After all cells in the flask settle to the bottom, content volume in excess of approximately 14 mL of GN6 S/M liquid was drawn off and collected in a sterile 1-L flask for future use. The pre-wetted suspension of whiskers was mixed at maximum speed on a vortex for 60 secs, and then added to the centrifuge bottle.

170 µg of purified fragment from either pDAB100610 or pDAB100611 plasmid DNA were added to each bottle. Once DNA was added, the bottle was immediately placed in a modified Red Devil 5400 commercial paint mixer (Red Devil Equipment Co., Plymouth, Minn.), and agitated for 10 secs. Following agitation, the cocktail of cells, media, whiskers and DNA were added to the contents of a 1-L flask along with 125 mL fresh GN6 liquid medium to reduce the osmoticant. The cells were allowed to recover on a shaker set at 125 rpm for 2 hrs. Six milliliters of dispersed suspension was filtered onto Whatman #4 filter paper (5.5 cm) using a glass cell collector unit connected to a house vacuum line such that 60 filters were obtained per bottle. Filters were placed onto 60×20 mm plates of GN6 solid medium (same as GN6 liquid medium except with 2.5 g/L Gelrite gelling agent) and cultured at 28° C. under dark conditions for 1 week.

Example 3

Identification and Isolation of Putative Transgenic Events

One week post-DNA delivery, filter papers were transferred to 60×20 mm plates of GN6 (1H) selection medium (N6 medium, 2.0 mg/L 2,4-D, 30 g/L sucrose, 100 mg/L myo-inositol, 2.5 g/L Gelrite, pH 5.8) containing the appropriate selective agent. These selection plates were incubated at 28° C. for one week in the dark. Following 1 week of selection in the dark, the tissue was embedded onto fresh media by scraping ½ the cells from each plate into a tube containing 3.0 mL of GN6 agarose medium held at 37-38° C. (N6 medium, 2.0 mg/L 2,4-D, 30 g/L sucrose, 100 mg/L myo-inositol, 7 g/L SEAPLAQUE® agarose, pH 5.8, autoclaved for 10 minutes at 121° C.).

The agarose/tissue mixture was broken up with a spatula and, subsequently, 3 mL of agarose/tissue mixture was evenly poured onto the surface of a 100×15 mm petri dish containing GN6 (1 H) medium. This process was repeated for both halves of each plate. Once all the tissue was embedded, plates were individually sealed with NESCOFILM® or PARAFILM® M, and cultured at 28° C. under dark conditions for up to 10 weeks. Putatively transformed isolates that grew under these selection conditions were removed from the embedded plates and transferred to fresh selection medium in 60×20 mm plates. If sustained growth was evident after approximately 2 weeks, an event was deemed to be resistant to the applied herbicide (selective agent) and an aliquot of cells was subsequently harvested for genotype analysis.

Example 4

Molecular Characterization of Events

Genomic DNA Extraction.

Genomic DNA (gDNA) was extracted from isolated maize cells and utilized as template for PCR genotyping experiments. gDNA was extracted from approximately 100-300 µl packed cell volume (PCV) of Hi-II callus that was isolated according to the manufacturer's protocols detailed in the DNEASY® 96 Plant Kit (QIAGEN Inc., Valencia, Calif.). Genomic DNA was eluted in 100 µl of kit-supplied elution buffer yielding final concentrations of 20-200 ng/µL, and subsequently analyzed via PCR-based genotyping methods.

Molecular Analysis of Copy Number.

Transgene copy number determination by hydrolysis probe assay, analogous to TAQMAN® assay, was performed by real-time PCR using the LIGHTCYCLER480® system (Roche Applied Science, Indianapolis, Ind.). Assays were designed for the AAD-1 and PAT genes and an internal reference gene using LIGHTCYCLER® Probe Design Software 2.0. For amplification, LIGHTCYCLER®480 Probes Master mix (Roche Applied Science, Indianapolis, Ind.) was prepared at 1× final concentration in a 10 µL, volume multiplex reaction containing 0.4 µM of each primer and 0.2 µM of each probe. A two-step amplification reaction was performed with an extension at 58° C. for 38 secs with fluorescence acquisition. All samples were run in triplicate and the averaged Cycle threshold (Ct) values were used for analysis of each sample. Analysis of real time PCR data was performed using LIGHTCYCLER® software release 1.5 using the relative quant module and was based on the ΔΔCt method. For this, a sample of genomic DNA from a single copy calibrator and known 2 copy check were included in each run (identical to those used for INVADER® assays above). From this data, the apparent AAD-1 or PAT copy number was then estimated for each sample.

Primer Design for PCR Genotyping.

Oligonucleotide primers were synthesized (e.g., by Integrated DNA Technologies, Inc. (Coralville, Iowa)) under conditions of standard desalting and diluted with water to a concentration of 100 μM. The oligonucleotide primer was designed to anneal to the end regions of the DNA insert. The primers were tested using dilutions of the plasmid DNA in the presence of DNA isolated from non-transgenic organisms. The insert of pDAB100610, pDAB100611 pDAB100640 and pDAB100641 was PCR amplified from genomic DNA of the putative events using the primers. The resulting fragment was cloned into a plasmid vector and sequenced to confirm that the engineered landing pad was completely integrated into the plant genome during the transformation.

Southern Blot Analysis.

Southern analysis was performed to confirm the transgene copy number. For this analysis, genomic DNA was digested with appropriate restriction enzymes and probed.

Maize tissue with identified as containing a putative ELP by locus specific PCR were advanced for Southern blots analysis. For Southern analysis, tissue samples were collected in 2 ml eppendorf tubes and lyophilized for 2 days. Tissue maceration was performed with a Kleco tissue pulverizer and tungsten beads (Kleco, Visalia, Calif.). Following tissue maceration, genomic DNA was isolated using the DNeasy Plant Mini kit (Qiagen, Germantown, Md.) according to the manufacturer's suggested protocol.

Genomic DNA was quantified by Quant-IT Pico Green DNA assay kit (Molecular Probes, Invitrogen, Carlsbad, Calif.). Quantified DNA was adjusted to 4 μg for the Southern blot analysis and digested using appropriate restriction enzymes overnight at 37° C. Digested DNA was purified using Quick-Precip (Edge BioSystem, Gaithersburg, Md.) according to the manufacturer's suggested protocol. Precipitated DNA was resupended in 10× dye and subjected to electrophoresis for 17 hrs on a 0.8% SeaKem LE agarose gel (Lonza, Rockland, Me.) at 40 volts. DNA was transferred to nylon charged membranes (Millipore, Bedford, Mass.) overnight and crosslinked to the membrane using the UV Strata linker 1800 (Stratagene, La Jolla, Calif.). Blots were prehbridized with 20 mL of PerfectHyb Plus (Sigma, St. Louis, Mo.) and probed with appropriate radio labeled probe overnight. Blots were washed and placed on phosphor image screens for 24 hrs and then analyzed using a STORM™ 860 scanner (Molecular Dynamics).

Example 5

Selection of Transgenic Events with Insert DNA

Events were screened by hydrolysis probe assay and PCR, as described above, for an intact plant transcriptional unit (PTU) containing the AAD-1 or PAT gene cassettes and intact ELPs. Copy number was further confirmed by Southern analysis using standard methods with an AAD-1 and PAT gene and an ELP probe. Callus from selected transgenic events harboring single copy, intact inserts from pDAB100610 and pDAB100611 were maintained for subsequent testing for expression of the AAD-1 gene. Screening using an AAD-1 qRT-PCR method and ELISA (below) identified the events expressing AAD-1.

qRT-PCR Analysis of AAD-1 Expressing Events.

Quantitative Real-Time PCR (qRT-PCR) was used to quantify the mRNA expression of the AAD-1 gene expression. The assay was developed to quantify the relative AAD-1 mRNA expression from transgenic Hi-II callus samples by normalizing these levels against mRNA expression from an internal reference gene. The normalization of the AAD-1 mRNA against mRNA from an internal reference gene permits comparison of AAD-1 expression between different samples, and can be used to identify events that appear to be highly expressing.

Total RNA was prepared from the fresh callus tissue using Qiagen RNeasy® 96 Kit (Qiagen, Valencia, Calif.). The RNA was treated with RNase-free DNase according to the kit's instructions to remove any genomic DNA contaminants. First strand synthesis was set up according to the Superscript® III Reverse Transcriptase Enzyme (Invitrogen, Carlsbad, Calif.) manufacturer's instructions and primed using random hexamers. The synthesized cDNA strands were diluted in water at ratios of 1:10 and 1:50 (this provides sufficient template to PCR amplify multiple targets). Each aliquot was saved at −20° C. indefinitely. qRT-PCR reaction mixes were set up for amplification of the AAD-1 cDNA as follows: 7.5 μL of 2× LC480 Probes Master Buffer (Roche Diagnostic, Indianapolis, Ind.), 0.34 gene specific forward primer from 10 μM stock, 0.3 μL gene specific reverse primer from 10 μM stock, 0.15 μL UPL probe from LightCycler® 480 Probes Master, Roche Diagnostic, Indianapolis, Ind.), 1.5 μL of 10% (w/v) polyvinyl pyrrolidone-40 (PVP-40), and 3.9 μL water. The UPL probe (Roche Diagnostics, Indianapolis, USA) was a locked nucleic acid and therefore has a higher than otherwise calculated. All components were put back in the freezer prior to handling standards and unknowns. A 384-well microplate was demarcated and labeled, 13.5 μL of master mix was added per well. A sealing foil was gently attached to the microplate. The plate was centrifuged for 1 minute at 3,000 rpm in a Qiagen microplate centrifuge. 1.5 μL of thawed, diluted synthesized cDNA strands were added. Additionally, 1.5 μL of plasmid DNA copy number standards were added to separate wells in a dilution series from lowest to highest concentrations, these standards were compared to the AAD-1 cDNA (synthesized from total mRNA) to quantitate the copy number. AAD-1 DNA copy number standard series were made by cloning the target amplicon into a pCR2.1 plasmid (Invitrogen, Carlsbad, Calif.) and making a dilution series for quantifying the copy number. A foil seal was firmly affixed to the plate and centrifuged as previously described. A PCR program was performed and DNA was amplified in Real-time PCR instrumentation LC480 (Roche, Indianapolis, Ind.) or equivalent.

Example 6

Determination of AAD-1 Protein in Maize Tissues by ELISA

A method to quantitatively determine the AAD-1 protein in maize callus using an enzyme-linked immunosorbent assay (ELISA) technique was developed. The method described herein can be used to detect the AAD-1 protein and analyze plant tissue samples from transgenic maize calli.

The AAD-1 protein was extracted from maize samples with callus-specific buffers based on phosphate buffered saline solution containing 0.05% Tween 20 (PBST), and possibly containing bovine serum albumin, protease inhibitors or ascorbic acid. The extract was centrifuged; the aqueous supernatant collected, diluted and assayed using a specific AAD-1 ELISA. A simultaneous sandwich ELISA format was applied in this assay. An aliquot of the diluted sample and a biotinylated anti-AAD-1 monoclonal antibody (MAb 473F185) were incubated in the wells of a microtiter plate coated with an immobilized anti-AAD-1 monoclonal antibody (MAb 473H274). These antibodies bound with maize expressed AAD-1 protein in the wells to form a "sandwich" with AAD-1 protein bound between soluble and the immobilized antibody. The unbound samples and conjugate were then removed from the plate by washing with PBST. An excess amount of streptavidin-enzyme (alkaline phosphatase) conjugate was added to the wells for incubation. The presence of AAD-1 was detected by incubating the enzyme conjugate with an enzyme substrate; generating a colored product. Since the AAD-1 was bound in the antibody sandwich, the level of color development is related to the concentration of AAD-1 in the sample (i.e., lower protein concentrations result in lower color development). The absorbance at 405 nm was measured using a plate reader.

High expressing AAD-1 events were identified from the selected transgenic events and were maintained for subsequent targeting with donor DNA.

Example 7

Biolistic-Mediated DNA Delivery into Plant Cells Containing an ELP

Regeneration of Transgenic Events with Target DNA

Events from pDAB100160 and pDAB100611 confirmed to be low copy and contain intact PTU were regenerated to produce immature embryo donor material for targeting. Healthy growing tissue was transferred first to 28+100 haloxyfop (MS medium (Murashige and Skoog (1962) Physiol Plant 15:473-497), 0.025 mg/L 2,4-D, 5 mg/L BAP, 0.0362 mg/L haloxyfop, 30 g/L sucrose, 2.5 g/L gelrite, pH 5.7) and incubated in low light (14 µE/m$^2$·sec 16 hr photoperiod) for 7 days followed by high light (89 µE/m$^2$·sec 16 hr photoperiod) for another 7 days. Greening structures were transferred to 36+100 haloxyfop (same as 28±100 haloxyfop minus the BAP and 2,4-D) and incubated in high light (40 g/m$^2$·sec 16 hr photoperiod) until shoot structures developed sufficient roots for transplanting to greenhouse. Plants were grown to maturity in greenhouse using mix of 95% Metro-Mix 360® and 5% clay/loam soil and pollinated dependent on health of plant. Vigorously growing plants were selfed or sibbed (plants from same event) and less vigorous plants were crossed with Hi-II, A188 or B104 to maintain embryogenic capacity of donor material.

Example 8

Biolistic-Mediated DNA Delivery into Plant Cells Containing an ELP

Targeting of Events Produced from pDAB100610 and pDAB100611.

Targeting of the donor sequence was completed using two different transformation protocols. For transgenic intact ELP events that contained AAD-1 as selectable marker (pDAB100610 and pDAB100611 events), targeting was performed via biolistic-mediated DNA delivery into pre-callused immature embryos. Embryos 1.2-2.0 mm in size were harvested 10-13 days post pollination and plated onto N6E medium (N6 medium, 2.0 mg/L 2,4-D, 2.8 g/L L-proline, 100 mg/L casein hydrolysate, 100 mg/L myo-inositol, 4.25 mg/L silver nitrate, 30 g/L sucrose, pH 5.8) and incubated at 28° C. for 2-3 days in dark. Swollen embryos were transferred to N6OSM (same as N6E with addition of 36.4 g/l sorbitol, 36.4 g/L mannitol and L-proline reduced to 0.7 g/L) that filled a 2.5 cm diameter circle on Whatman #4 filter paper. A 1,000 mm screen was used to contain the embryos for blasting and embryos were incubated in dark at 28° C. for 4 hr prior to blasting. To coat the biolistic particles with DNA, 3 mg of 0.60 micron diameter gold particles were washed once with 100% ethanol, twice with sterile distilled water, and resuspended in 50 µl water in a siliconized microfuge tube. A total of 5 µg of plasmid DNA separate vectors encoding the zinc finger nuclease and Donor DNA fragment; pDAB105955 or pDAB105956), 2 µl spermidine (0.1 M) and 5 µl calcium chloride (2.5 M) were added separately to the gold suspension and mixed on a vortex. The mixture was incubated at room temperature for 10 min, pelleted at 10,000 rpm in a benchtop microcentrifuge for 10 secs, resuspended in 60 ml cold 100% ethanol, and 8-9 µl was distributed onto each macrocarrier.

Bombardment took place using the Biolistic PDS-1000/HE™ system (Bio-Rad Laboratories, Hercules, Calif.). Plates containing the embryos were placed on the middle shelf under conditions of 650 psi and 27 inches of Hg$^{++}$ vacuum, and were bombarded once following the operational manual. Twenty four hrs post-bombardment embryos were transferred directly (no filter paper) to N6E (same as above) for recovery and incubated for 13 days at 28° C. in the dark. Embryos were transferred to selection medium N6S(N6 medium, 2.0 mg/L 2,4-D, 100 mg/L myo-inositol, 0.85 mg/L silver nitrate, 2 mg/L bialaphos, 30 g/L sucrose, 2.5 g/L gelrite and pH 5.8) for every 2 weeks for 3 transfers on selection medium and incubated at 28° C. in dark conditions for up to 10 weeks. Putatively transformed isolates that grew under these selection conditions were removed from the embedded plates and transferred to fresh selection medium in 60×20 mm plates. If sustained growth was evident after approximately 2 weeks, an event was deemed to be resistant to the applied herbicide (selective agent) and an aliquot of cells was subsequently harvested for genotype analysis (analysis described below).

Targeting of Events Produced from pDAB100640 and pDAB100641.

For transgenic intact ELP events that contained PAT as selectable marker (pDAB100640 and pDAB100641) targeting was performed via biolistic-mediated DNA delivery into embryogenic maize callus. Six to eight days post subculture, embryogenic maize tissue ((approximately 0.4 mL PCV of cells) was thinly spread in a circle 2.5 cm in diameter on top of Whatman #4 filter paper placed on a 100×15 mm petri dish containing GN6 S/M media (N6 medium, 2.0 mg/L 2,4-D, 30 g/L sucrose, 45.5 g/L sorbitol, 45.5 g/L mannitol, 100 mg/L myo-inositol, pH 5.8) solidified with 2.5 g/L gelrite. The cells were incubated under dark conditions for 4 hrs. DNA was prepped for blastings as described previously, pDAB105979 and pDAB105980 was used for the targeting.

Bombardment took place using the Biolistic PDS-1000/HE™ system (Bio-Rad Laboratories, Hercules, Calif.). Plates containing the cells were placed on the middle shelf under conditions of 1,100 psi and 27 inches of Hg$^{++}$ vacuum, and were bombarded once following the operational manual. Twenty-four hrs post-bombardment, the filter paper containing the plant cells was transferred to GN6 solid medium (N6 medium, 2.0 mg/L 2,4-D, 100 mg/L myo-inositol, 30 g/L sucrose, pH 5.8) solidified with 2.5 g/L Gelrite and incubated for 24 hrs at 28° C. under dark conditions. After the 24 hrs recovery period, the filter paper containing the plant cells was transferred to GN6+100 haloxyfop (N6 medium, 2.0 mg/L 2,4-D, 100 mg/L myo-inositol, 30 g/L sucrose, 0.0362 mg/L haloxyfop, 2.5 g/L Gelrite, pH5.8), spreading the cells out in a thin layer on the filter paper. Transfers continued every 2 weeks for 3 transfers on selection medium. Tissue was incubated for up to 12 weeks until putative transgenic isolates resulting from integration of donor DNA began to appear. Putatively transformed isolates that grew under these selection conditions were removed from the embedded plates and transferred to fresh selection medium in 60×20 mm plates. If sustained growth was evident after approximately 2 weeks, an event was deemed to be resistant to the applied herbicide (selective agent) and an aliquot of cells was subsequently harvested for genotype analysis (analysis described below).

Example 9

Screening for Targeted Integration Events Via PCR Genotyping

Targeting of donor molecules (pDAB105979, pDAB105980, pDAB105955, pDAB105956) into ELPs in transgenic maize is analyzed by using a combination of: 1) locus specific PCR; 2) donor specific TaqMan, and; 3) locus specific Southern blots to assess insert precision, intactness and copy number. A positive retargeted event is expected to have a) a positive out-out PCR or overlapping in-out PCR outcome and 2) a Southern image diagnostic of the presence of a donor.

DNA Extraction

Tissue from retargeted transgenic maize (callus tissue or plant leaves) is lyophilized for at least 2 days in 96-well collection plates (Qiagen, Germantown, Md.). DNA is extracted from lyophilized tissue using a BioSprint 96 workstation (Qiagen, Germantown, Md.) following the manufacturer's instructions and resuspended in 200 µl of water. A Model 2-96A Mew tissue pulverizer (Garcia Manufacturing, Visalia Calif.) is used for tissue disruption.

DNA Quantification: Resulting genomic DNA is quantified using a QUANT-IT® Pico Green DNA assay kit (Molecular Probes, Invitrogen. Carlsbad, Calif.). Five prequantified DNA standards ranging from 20 ng/µL to 1.25 ng/µL (serially diluted) are used for standard curve generation. Unknown samples are first diluted 1:10 or 1:20 dilutions to be within the linear range of the assay. 5 µL of diluted samples and standards are mixed with 100 µL of diluted Pico Green substrate (1:200) and incubated for ten minutes in the dark. Fluorescence is then recorded using a Synergy2 plate reader (Biotek). Genomic DNA concentration is estimated from the standard curve calculated after background fluorescence corrections. DNA is subsequently normalized to concentrations of 2 ng/µL using a Biorobot-3000 automated liquid handler (Qiagen, Germantown, Md.). Normalized DNA is used for PCR, and copy number analysis.

PCR Analysis

Figure 9A:
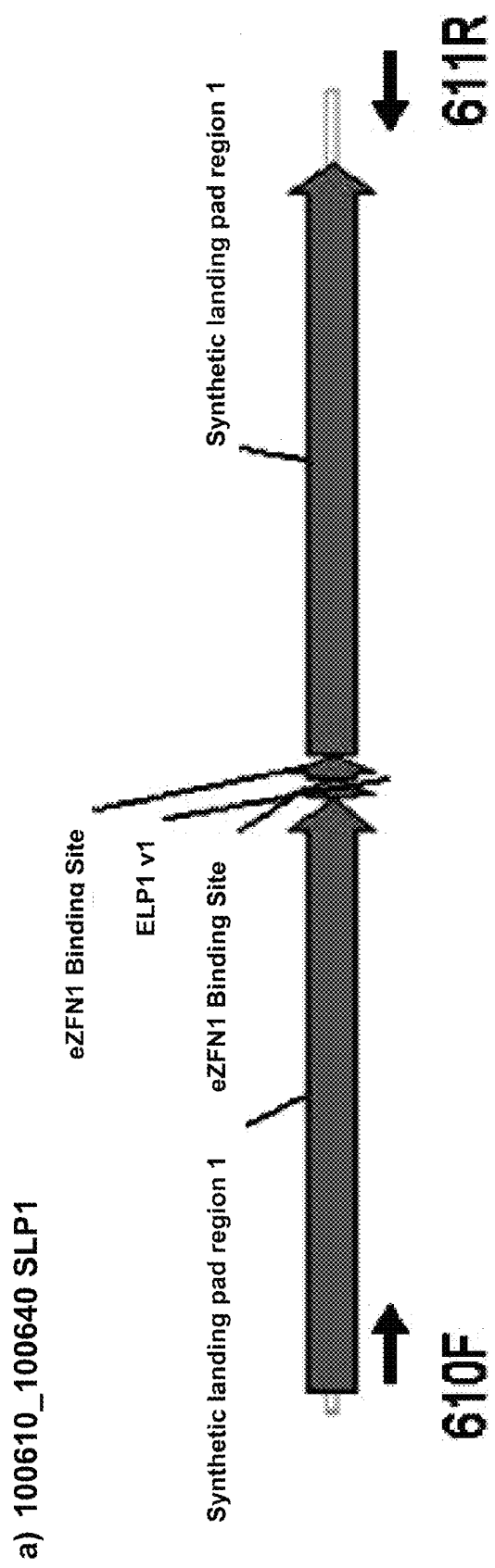
FIGS. 9a-9c include schematics of: 9a) ELP 1 in maize; 9b) donor construct for ELP1 retargeting; and 9c) Retargeted ELP1 locus.
Figure 9B:
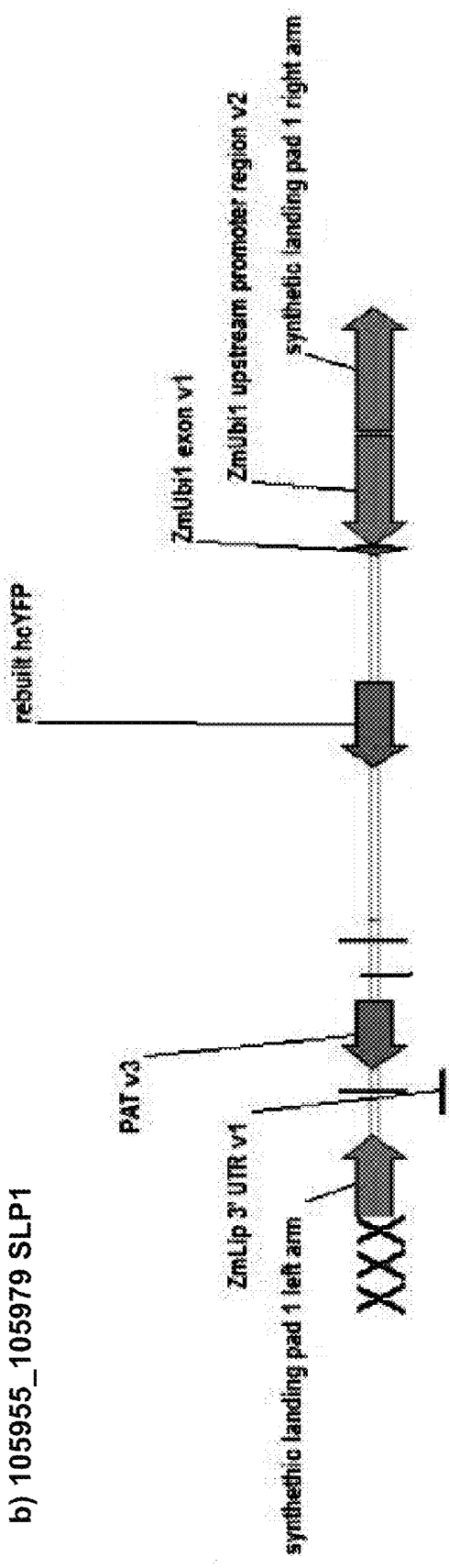
Figure 9C:
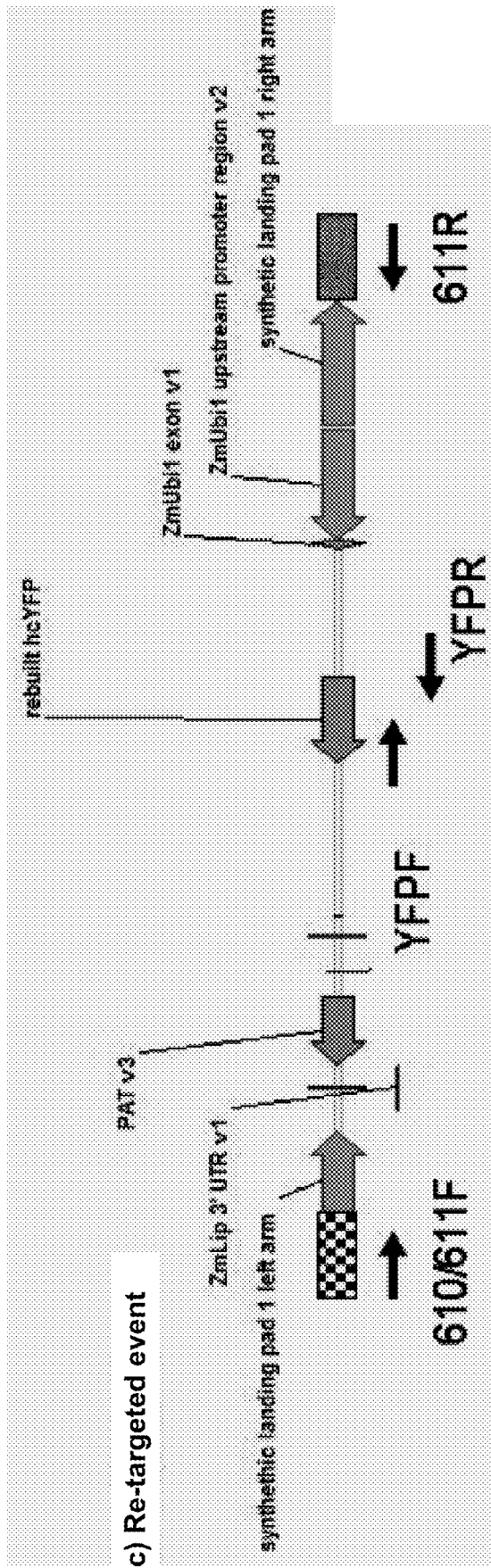

Three types of locus specific PCR (out-out, 5' out-in, 3' out-in) are performed to evaluate whether donor plasmids are targeted to the ELPs. PCR reactions are performed to investigate the presence of an intact copy of the donor DNA (out-out PCR). Additional PCR reactions focus on the 5'-boundary between target and donor and the 3'-boundary between donor and target (in-out PCR). A schematic with positions of the primers used for the analysis is exemplified in FIGS. 9a-9c. The expected PCR products for each donor and ELP target are outlined in Table 1. The sequences of primers used for the analysis are shown in Table 2.

TABLE 1

Expected amplicon sizes for locus specific PCR for targeted donor integration analysis.

| Target ELP Plasmid ID | Retargeting Donor | Primers * | Expected Amplicon (kB) |
|---|---|---|---|
| pDAB100640 | pDAB105979 | 610F-611R | 8.5 |
|  | sLP1L-YFP-AAD1- | 610-YFP | 3.5 |
|  | sLP1R | YFP-611 | 5.4 |
| pDAB100641 | pDAB105980 | 611/611 | 7.6 |
|  | sLP2L-YFP-AAD1- | 611/YFP | 4.4 |
|  | sLP2R | YFP/611 | 3.5 |
| pDAB106685 | pDAB105979 | 610F-611R | 8.5 |
|  | sLP1L-YFP-AAD1- | 610-YFP | 3.5 |
|  | sLP1R | YFP-611 | 5.4 |
| pDAB106686 | pDAB105980 | 611/611 | 7.6 |
|  | sLP2L-YFP-AAD1- | 611/YFP | 4.4 |
|  | sLP2R | YFP/611 | 3.5 |
| pDAB100610 | pDAB105955 | 610F-611R | 8.5 |
|  | sLP1L-YFP-PAT-sLP1R | 610-YFP | 3.5 |
|  |  | YFP-611 | 5.4 |
| pDAB100611 | pDAb105956 | 611/611 | 7.6 |
|  | sLP2L-YFP-PAT-sLP2R | 611/YFP | 4.4 |
|  |  | YFP/611 | 3.5 |

\* primers listed in order for:
out-out
5' in-out
3' out- in

TABLE 2

Sequences of primers used for targeted integration analysis

| Oligo | SEQ ID NO: | Sequence |
|---|---|---|
| 610F | SEQ ID NO: 21 | GCTACTAAGAACAATACCTAAGTTGC |
| 611F | SEQ ID NO: 22 | TGCACTCATGTTCATATCC |
| 611R | SEQ ID NO: 23 | TGTACAAGAAAGCTGGGTG |
| YFPF_3302 | SEQ ID NO: 24 | TATGGTCCAGAGTTGAAGG |
| YFPR_4577 | SEQ ID NO: 25 | TCATCTGCACAACTGGTGA |
| YFPF_4302 | SEQ ID NO: 26 | TCTTTCCCAACACATGACC |

PCR Amplification:

The polymerase chain reaction (PCR) is performed to evaluate and confirm retargeting of the ELPs. PCR reactions are prepared in a 25 µl volume with Phusion DNA polymerase (New England Biolabs, Ipswich, Mass.) or AccuPrime (Invitrogen, Carlsbad, Calif.). For Phusion PCR each reaction contains 1× Phusion GC buffer, 0.2 mM dNTPs, 0.2 µM of forward and reverse oligos, 2.5 units of Phusion DNA polymerase and 20 ng of genomic DNA. Ten to twenty ng of plasmid DNA constructed to mimic a retargeted event is run as a positive control. A non template control (water as template) is also run. PCR conditions are as follows: 35 cycles of 98° C., 1 min, 98° C. 10 sec, 65° C., 20 sec, 72° C. for 2.5 min followed by 72° C. for 10 min.

Twenty five microliter PCR reactions performed with AccuPrime (Invitrogen, Carlsbad, Calif.) contained 1× buffer II, 0.2 µM of forward and reverse oligos, 2.5 units of AccuPrime Taq polymerase, and 20 ng of genomic DNA. Positive and negative controls are run as described above for Phusion. Conditions for AccuPrime are as follows: 35 cycles of 98° C., 1 min, 98° C. 10 sec, 65° C., 20 sec, 68° C. for 2.5 min followed by 68° C. for 10 min.

Amplified fragments are gel-excised and purified according to manufacturer's directions. Purified fragments are subsequently cloned into a plasmid vector and transformed into competent E. coli cells.

Individual colonies are selected and confirmed to contain the amplified PCR fragment. Double-stranded sequencing reactions of plasmid clones are performed to confirm that the PCR amplified genomic sequence contains the integrated donor. Events identified to contain the donor fragment represent a target in which homology-driven repair of a ZFN-mediated double-stranded break and targeted integration of a donor DNA at a specific gene target have occurred.

Hydrolysis Probe/TaqMan Assay

TaqMan analysis is conducted to define copy number of donors in putative retargeted events. Copy number determination by hydrolysis probe assay, analogous to TAQMAN® assay, is performed by real-time PCR using the LIGHTCYCLER®480 system (Roche Applied Science, Indianapolis, Ind.). Assays are designed for PAT and AAD1 and the internal reference gene GLP1 and Invertase using LIGHTCYCLER® Probe Design Software 2.0. For amplification, LIGHTCYCLER®480 Probes Master mix (Roche Applied Science, Indianapolis, Ind.) is prepared at 1× final concentration in a 10 µL volume multiplex reaction containing 0.4 35 cycles of 98° C., 1 min, 98° C. 10 sec, 65° C., 20 sec, 72° C. for 2.5 min followed by 72° C. for 10 min. M of each primer and 0.2 35 cycles of 98° C., 1 min, 98° C. 10 sec, 65° C., 20 sec, 72° C. for 2.5 min followed by 72° C. for 10 min. M of each probe (Table 3). A two step amplification reaction is performed with an extension at 58° C. for 38 secs for PAT/GLP1 and 60° C. for 40 secs for AAD-1 and Invertase with fluorescence acquisition. All samples are run in triplicate and the averaged Cycle threshold (Ct) values are used for analysis of each sample.

Analysis of real time PCR data is performed using LIGHTCYCLER® software release 1.5 using the relative quant module and is based on the ΔΔCt method. For this, a sample of gDNA from a single copy calibrator and known 2 copy check were included in each run.

TABLE 3

Primer and probe information for hydrolysis probe assay of pat and internal reference (HMG)

| Primer Name | Sequence | Detection |
|---|---|---|
| TQPATS | SEQ ID NO: 27; 5' ACAAGAG TGGATTGATGATCTAGAGAGGT 3' | |
| TQPATA | SEQ ID NO: 28; 5' CTTTGAT GCCTATGTGACACGTAAACAGT 3' | |
| TQPATFQ | SEQ ID NO: 29; 5' CY5-GGTGTT GTGGCTGGTATTGCTTACGCTGG-BHQ2 3' | Cy5 |
| ZGP3S | SEQ ID NO: 30; 5' CCTGCTC CACTACCAGTACAA 3' | |
| ZGP3A | SEQ ID NO: 31; 5' GTCCAAG AAGGTGACCTTCTC 3' | |
| TQZGP3 | SEQ ID NO: 32; 5' FAM-AGA TCACCGACTTTGCGCTCTTT-BHQ1 3' | FAM |
| GAAD1F | SEQ ID NO: 33; 5' TGTTCGGT TCCCTCTACCAA 3' | |
| GAAD1R | SEQ ID NO: 34; 5' CAACATCC ATCACCTTGACTGA 3' | |

TABLE 3-continued

Primer and probe information for hydrolysis probe assay of pat and internal reference (HMG)

| Primer Name | Sequence | Detection |
|---|---|---|
| GAAD1P | SEQ ID NO: 35; 5' FAM-CACA GAACCGTCGCTTCAGCAACA 3' | FAM |
| IVF-Taq | SEQ ID NO: 36; 5' TGGCGGAC GACGACTTGT 3' | |
| INR-Taq | SEQ ID NO: 37; 5' AAAGTTTG GAGGCTGCCGT 3' | |
| IV-Probe | SEQ ID NO: 38; 5' HEX CGAG CAGACCGCCGTGTACTTCTACC 3' | HEX |

Southern Analysis

Southern analysis is performed to confirm targeting of the donor DNA at the ELP locus. For this analysis, genomic DNA is digested with appropriate restriction enzymes and probed with a locus specific radiolabeled fragment (not present in the donor).

Maize callus (pDAB100640 and pDAB100641 target experiments) or T0 maize plants (pDAB100610 and pDAB100611 target experiments) are used. Tissue samples are collected in 2 ml microfuge tubes and lyophilized for 2 days. Tissue maceration is performed with a Kleco tissue pulverizer and tungsten beads as above. Following tissue maceration, genomic DNA is isolated using the DNeasy Plant Mini kit (Qiagen, Germantown, Md.) according to the manufacturer's suggested protocol.

Genomic DNA is quantified by Quant-IT Pico Green DNA assay kit (Molecular Probes, Invitrogen, Carlsbad, Calif.). Four micrograms of DNA for each sample is digested using appropriate restriction enzymes overnight at 37° C. Digested DNA is purified using Quick-Precip (Edge BioSystem, Gaithersburg, Md.) according to the manufacturer's suggested protocol. After electrophoresis on a 0.8% SeaKem LE agarose gel (Lonza, Rockland, Me.), DNA is transferred to nylon charged membranes (Millipore, Bedford, Mass.) overnight and crosslinked to the membrane using the UV Strata linker 1800 (Stratagene, La Jolla, Calif.). Blots are prehybridized with 20 ml of PerfectHyb Plus (Sigma, St. Louis, Mo.) and probed with appropriate radio-labeled probe overnight. Blots are washed and placed on phosphor image screens for 24 hr and then analyzed using a Storm 860 scanner (Molecular Dynamics).

Example 10

Construction of an Intermediate Plant Transformation Vector that Will Accept ELPS, Selectable Markers and are Enabled for in Planta Excision of Independent Construct Elements Engineered zinc finger nuclease (eZFN) binding sites and ELP elements can be incorporated, individually or together, into plant transformation vectors such that the resulting transformed plant cells, tissues or plants will have the following properties: 1) ability to be re-transformed with additional transgenes in a precise, targeted manner within the ELP at the original transgenic insertion site and 2) the ability to modify transgenic loci by removing transgenes, particularly plant selectable marker genes, in a predictable and efficient manner. A series of vectors were constructed for transforming a range of plant species. This was accomplished by use of an "intermediate plant transformation vector" (described below), a vector to affect incorporation of eZFNs flanking all selectable markers and ELPs into base vectors known as primary transformation vectors.

Figure 10:
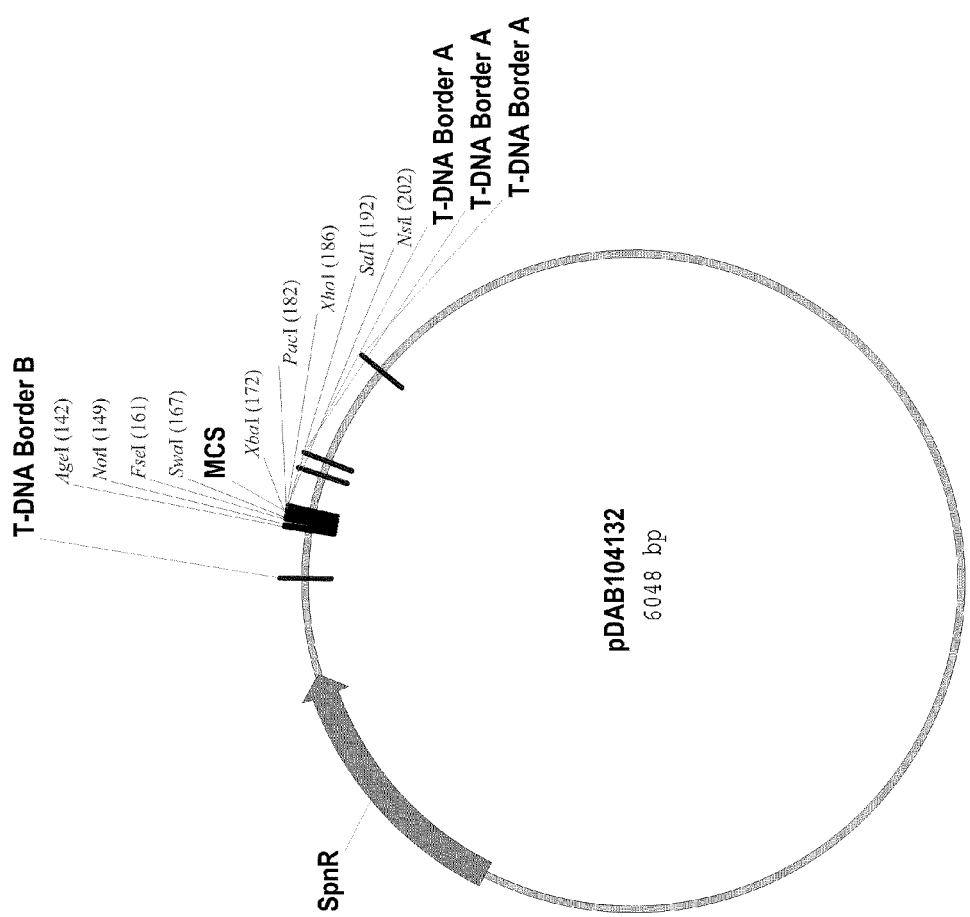
FIG. 10 includes a depiction of a representative vector pDAB104132.

An intermediate plant transformation vector was constructed that comprised an *Agrobacterium* binary transformation vector backbone with a unique multiple cloning site (MCS) positioned between the right and left T-DNA borders. This intermediate vector is pDAB104132 (FIG. 10). The MCS used in pDAB104132 contains unique restriction enzyme sites for AgeI, NotI, FseI, SwaI, XbaI, AseI, PadI, XhoI, SalI, and NsiI. In this example, these sites are used to incorporate key functional elements into the final primary transformation vectors. The unique NotI site can be used to introduce a NotI fragment carrying a GATEWAY™ destination vector cassette, which can then be subsequently used to stack multiple transgenes into the transformation vector using Invitrogen's GATEWAY™ system. The unique FseI site can be used to introduce ELPs which have FseI sites at their termini. As described previously in these examples, when present in a transgenic plant, ELPs can be used as target sites to insert additional genes using eZFNs. Other sites in the MCS can be used to insert other genes of interest, including selectable marker genes. Using the unique restriction sites described above, intermediate plant transformation vectors such as pDAB104132 can be used to bring together into a single plant transformation vector any and all combinations of functional elements including GATEWAY™ destination vector cassettes, ELPs, selectable marker-ZFN modules, and any other transgenes that may or may not be enabled for eZFN excision.

Example 11

Construction of Excision-Enabled Plant Selectable Marker Cassettes Using Zinc Finger Nuclease Modules In this example, eZFN binding sites are used to enable in planta deletion of any transgene, including selectable marker genes, from a transformed plant. See U.S. Provisional Patent Application No. 61/297,628, herein incorporated by reference. This capability is achieved by flanking the transgenes with one or more eZFN binding sites and then incorporating these excisable gene modules into plant transformation vectors which are then used to generate transgenic plant cells. Construction of such modules and vectors can be accomplished by one skilled in the art using standard molecular biology techniques.

Figure 11:
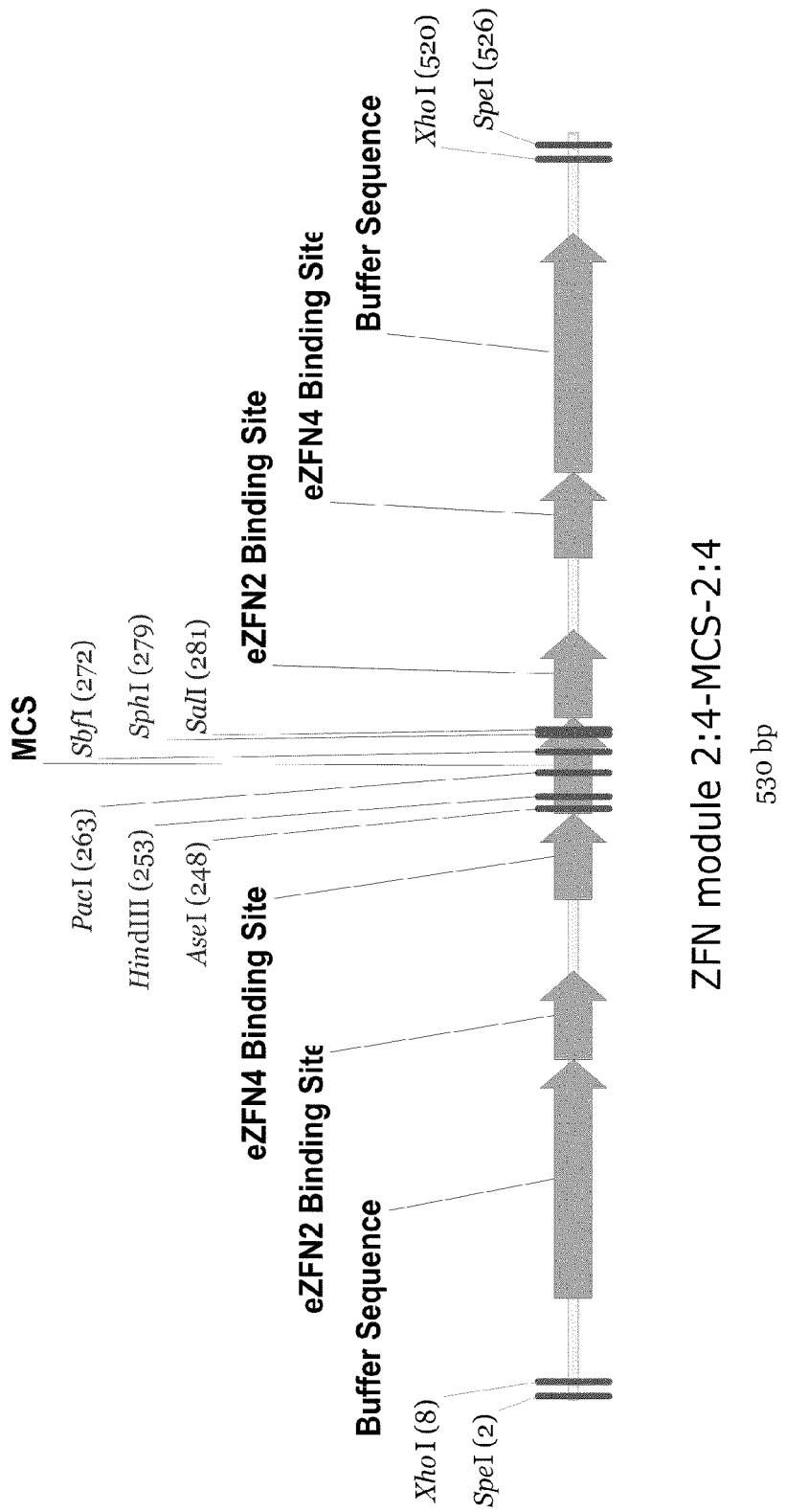
FIG. 11 includes a depiction of a representative DNA fragment of a Multiple Cloning Site which is flanked by engineered Zinc Finger binding sites and buffer sequences.
Figure 12:
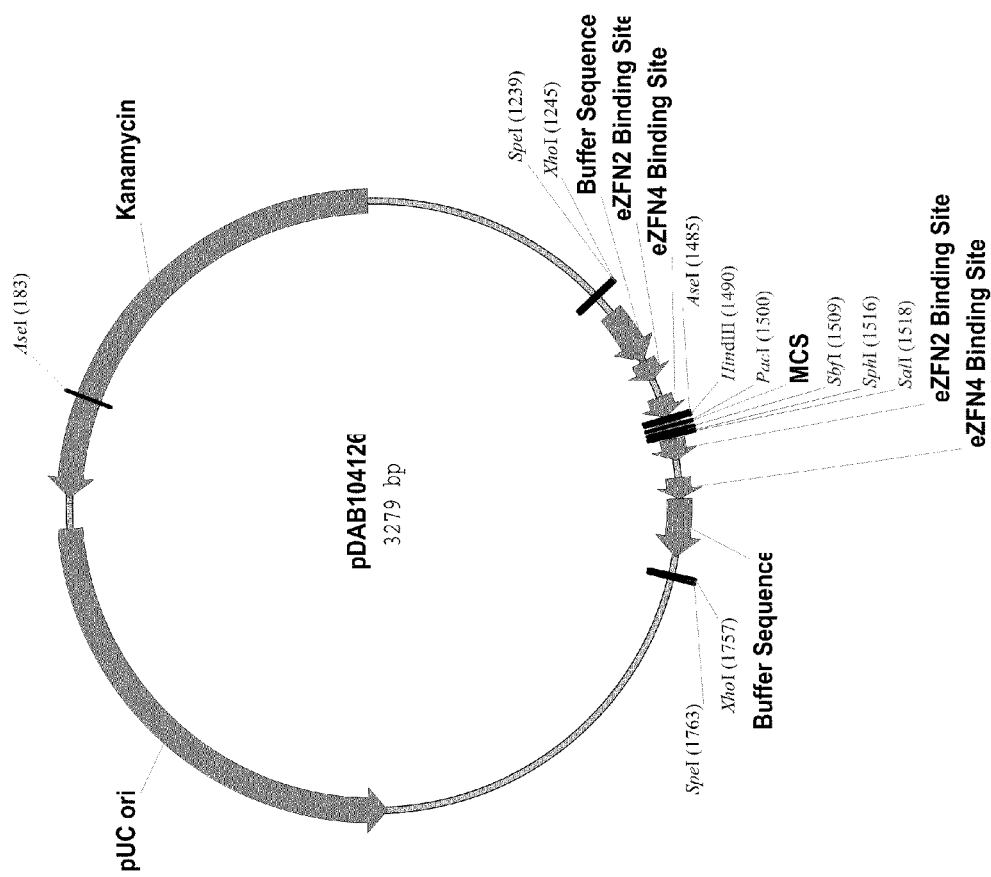
FIG. 12 includes a depiction of a representative vector pDAB104126.

An intermediate plasmid carrying a ZFN binding site module is a useful first step towards constructing excisable gene cassettes. An eZFN binding site module is a segment of DNA that contains at least two eZFN binding sites flanking one or more restriction enzyme sites into which transgenes can be cloned. An example is the ZFN module 2:4-MCS-2:4 represented by SEQ ID: 20 and FIG. 11. This module contains a multiple cloning site (MCS) consisting of restriction sites AseI, HindIII, PadI, SbfI, SphI and SalI that are flanked by pairs of binding sites for eZFN2 and eZFN4. Also within this ZFN module are two identical copies of a sequence consisting of 100 bp random sequence that flank the eZFN binding sites. Additionally, pairs of restriction enzyme sites SpeI and XhoI flank the entire functional module, allowing for its cloning into a plant transformation vector. pDAB104126, a plasmid carrying ZFN module 2:4-MCS-2:4 is shown in FIG. 12.

Figure 13:
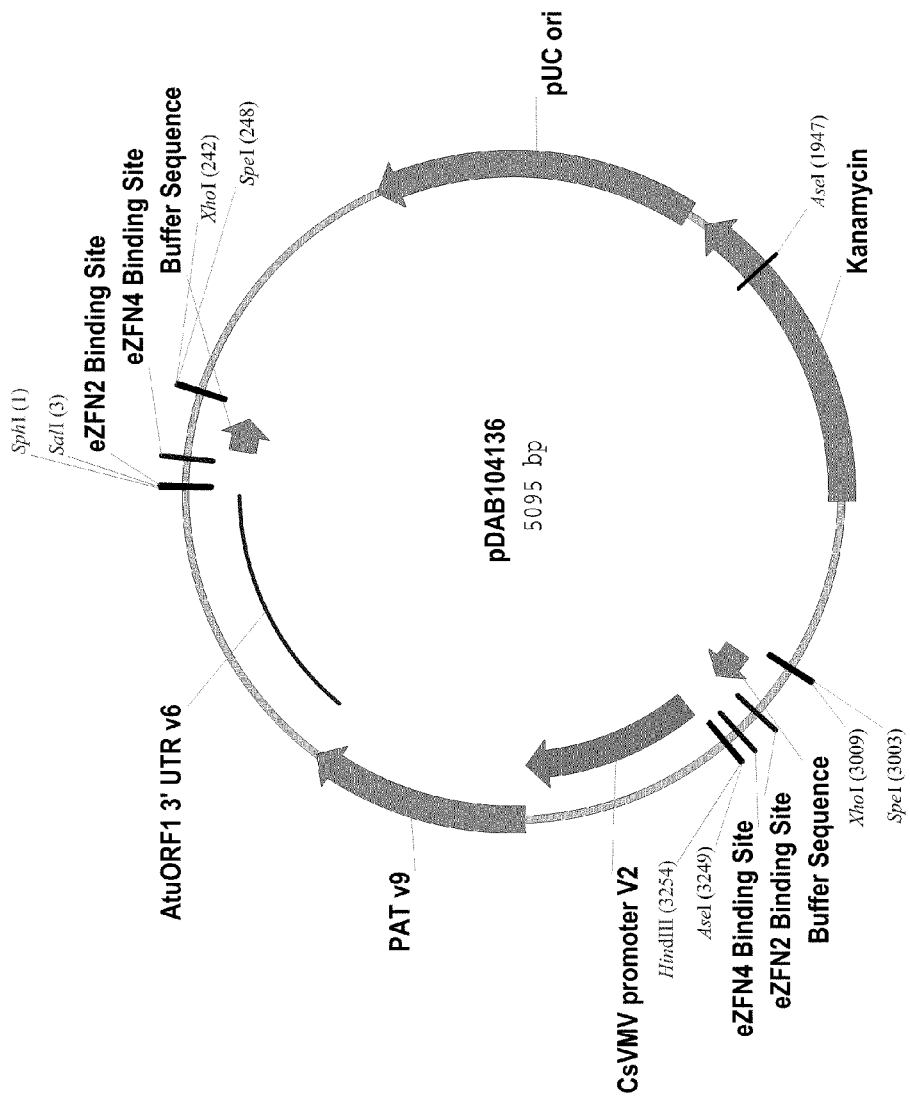
FIG. 13 includes a depiction of a representative vector pDAB104136.

Four different plant selectable marker genes were individually inserted into the ZFN module 2:4-MCS-2:4 in pDAB104126 using standard molecular cloning techniques. One selectable marker gene was a functional PAT gene designed to confer glufosinate tolerance in dicot plants. This PAT gene was comprised of a PAT coding sequence operably linked to a CsVMV promoter (promoter and 5' untranslated region derived from the Cassava Vein Mosaic virus; Verdaguer et al. (1996) Plant Molecular Biology 31(6):1129-1139) and the AtuORF1 3' UTR. The PAT gene cassette was inserted as a HindIII-SphI fragment into the HindIII-SphI sites of the ZFN module to yield plasmid pDAB104136 (FIG. 13).

Figure 14:
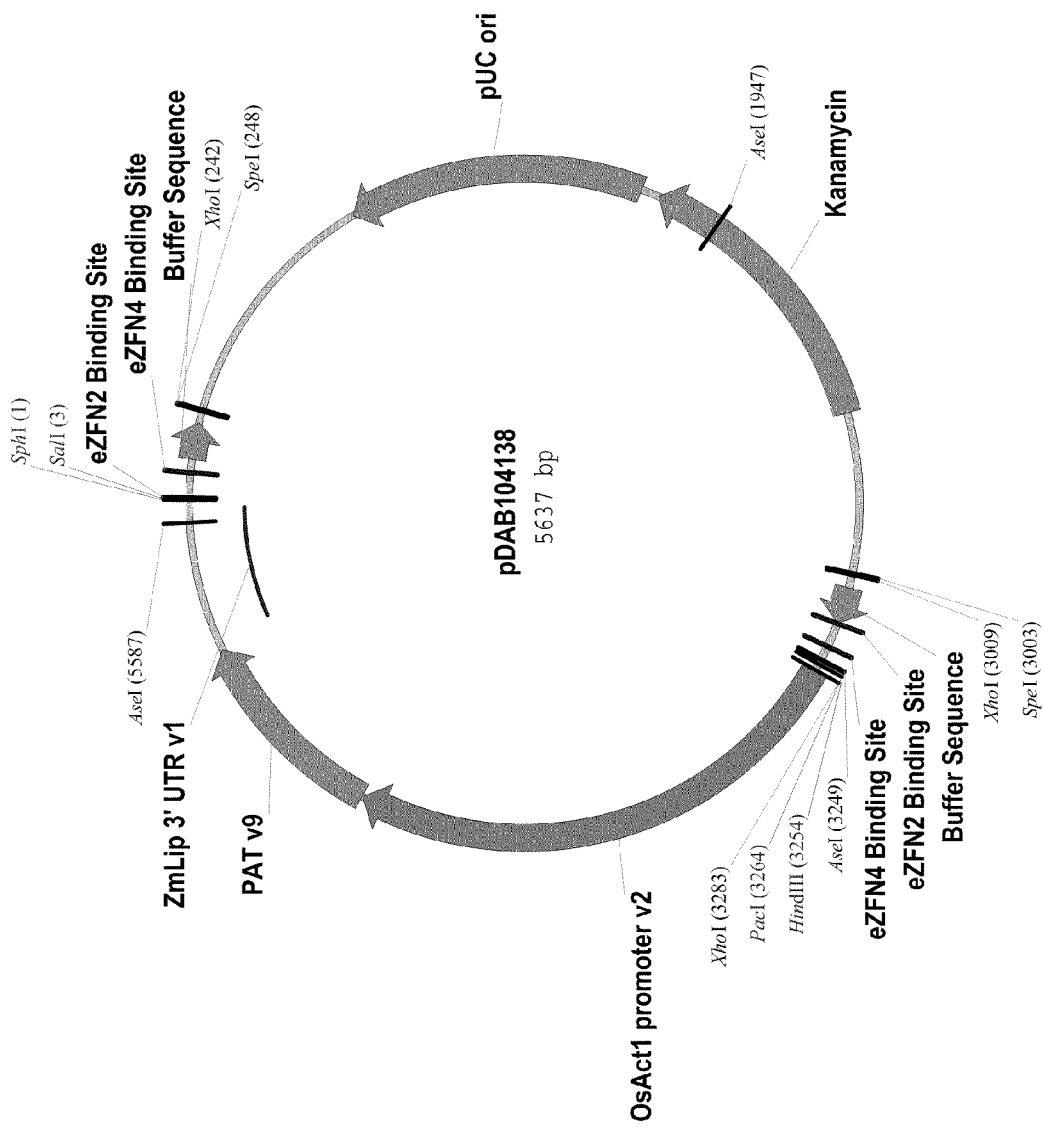
FIG. 14 includes a depiction of a representative vector pDAB104138.

A second selectable marker gene was a PAT gene designed to confer glufosinate tolerance in monocot plants. This PAT gene comprised a PAT coding sequence operably linked to a OsAct1 promoter and a ZmLip 3' UTR. This monocot PAT gene was inserted as a PacI-SphI fragment into the PacI-SphI sites of the ZFN module to yield plasmid pDAB104138 (FIG. 14).

Figure 15:
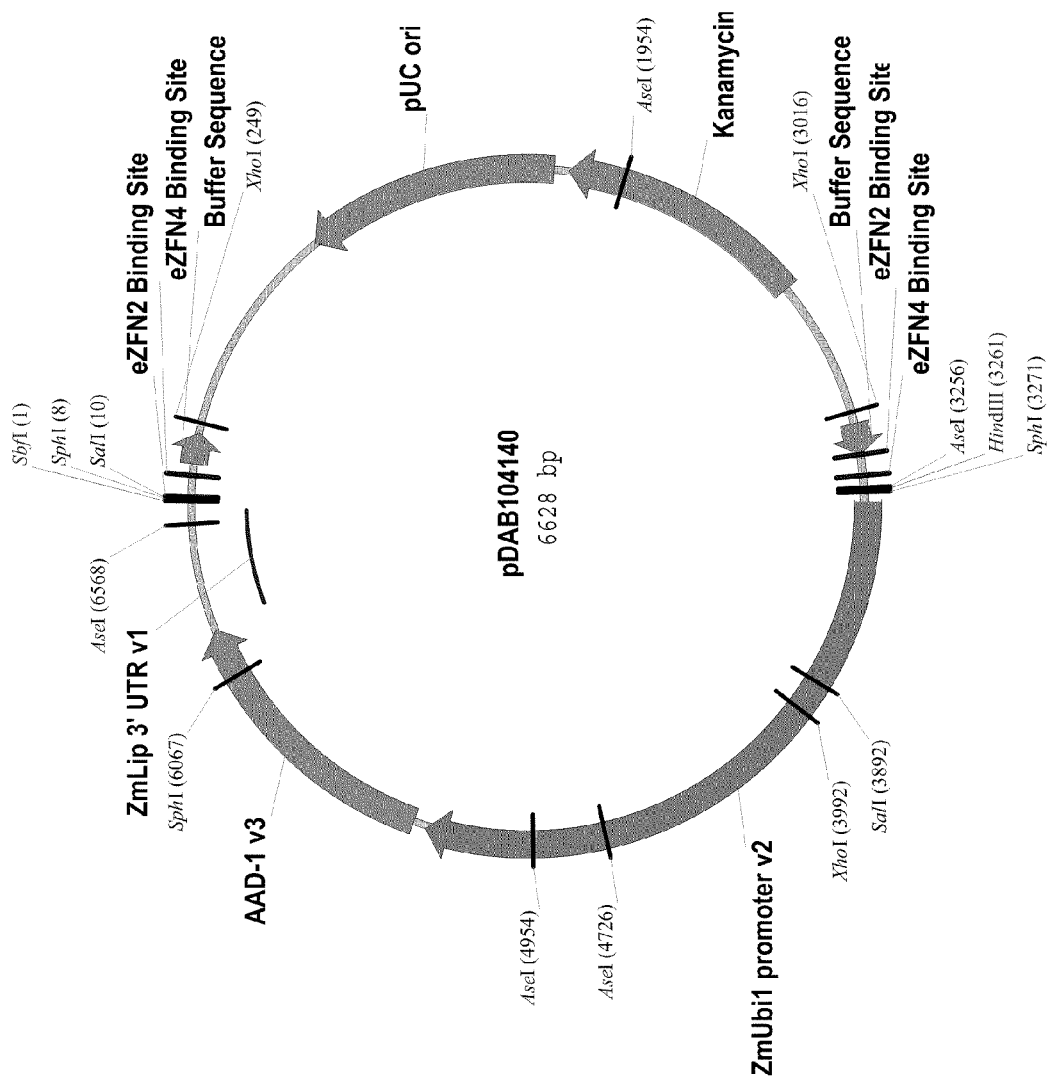
FIG. 15 includes a depiction of a representative vector pDAB104140.

A third selectable marker gene comprised an AAD-1 gene designed to confer haloxyfop or 2,4-D tolerance in monocot plants. This AAD-1 gene comprised a AAD-1 coding sequence operably linked to the ZmUbi1 promoter and a ZmLip 3' UTR. This monocot AAD-1 gene was inserted as a HindIII-SbfI fragment into the HindIII-SbfI sites of the ZFN module to yield plasmid pDAB104140 (FIG. 15).

Figure 16:
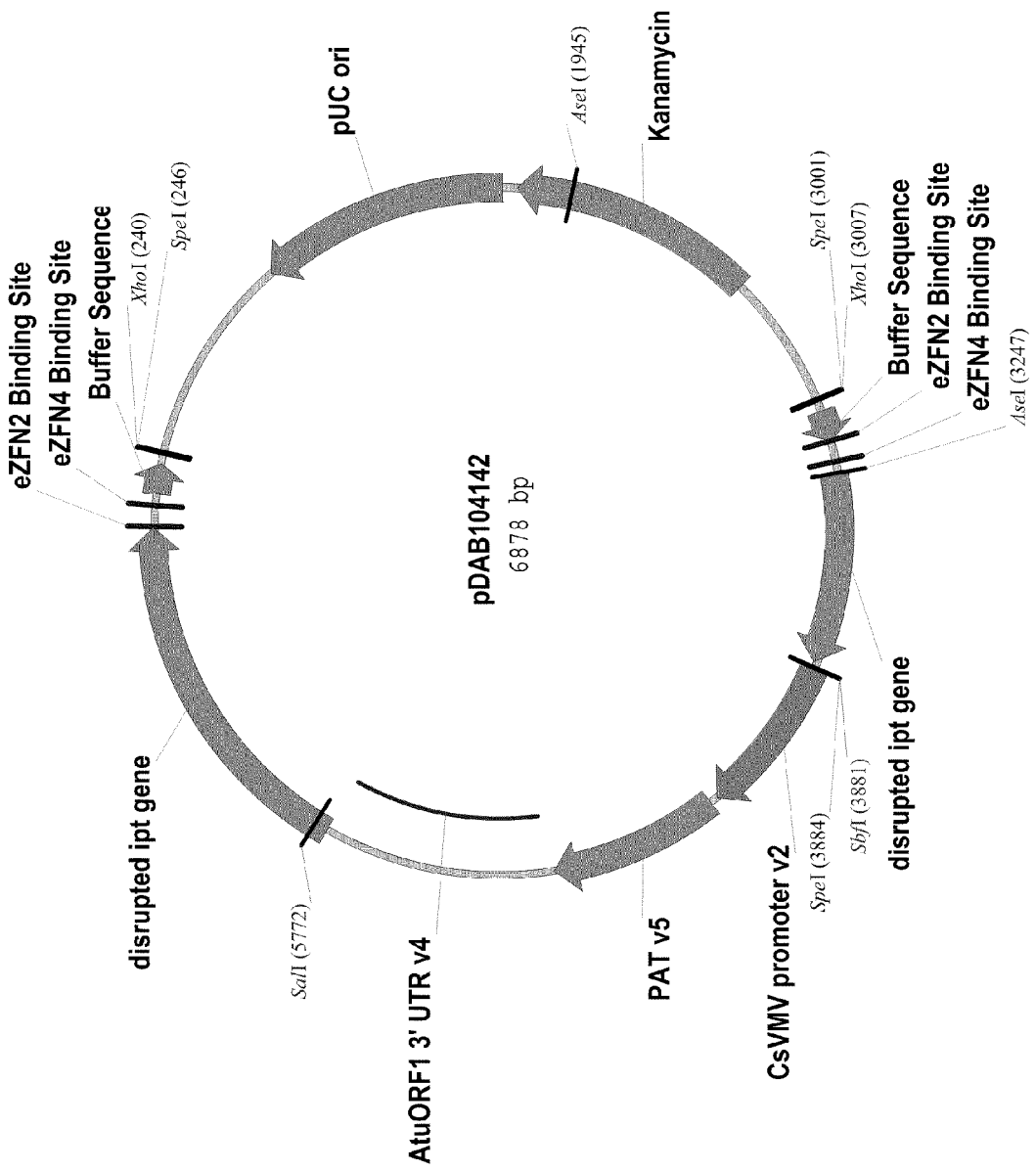
FIG. 16 includes a depiction of a representative vector pDAB104142.

A fourth selectable marker gene comprised a PAT gene designed to confer glufosinate tolerance in canola plants. This PAT gene comprised a PAT coding sequence operably linked to a CsVMV promoter and an AtuORF1 3' UTR and placed within a disrupted isopentenyl transferase (ipt) gene. The PAT gene was inserted as a AseI-SalI fragment into the Ase-XhoI sites of the ZFN module to yield plasmid pDAB104142 (FIG. 16).

Thus, pDAB104136, pDAB104138, pDAB104140 and pDAB104142 are intermediate plasmids which carry different ZFN excision enabled selectable marker genes that can be incorporated into plant transformation vectors. When finally incorporated into a plant genome by transformation, the selectable marker ZFN modules allow for the subsequent removal of the selectable marker gene. This can be achieved by producing eZFN2 or eZFN4 proteins in the plant cells either by transient expression or stable expression of genes encoding them. For example eZFN2, or alternately eZFN4, can be expressed in previously transformed plant cells by transient expression of the eZFN from either eZFN2 or eZFN4 genes. The eZFN enzymes will recognize and bind the specific eZFN binding sites and causes double strand breaks to occur in the genome at these positions. Double strand breaks on both sides of the selectable marker gene within the module will result in excision of the selectable marker gene from the genome DNA. Subsequently, the double strand break will be repaired, either by non-homologous end joining or by homologous single-strand repair between the repeated 100 bp sequences that were included in the ZFN module. This process will result in permanent deletion of the selectable marker gene for its original genomic location.

Example 12

Assembly of Primary Plant Transformation Vectors

Figure 17:
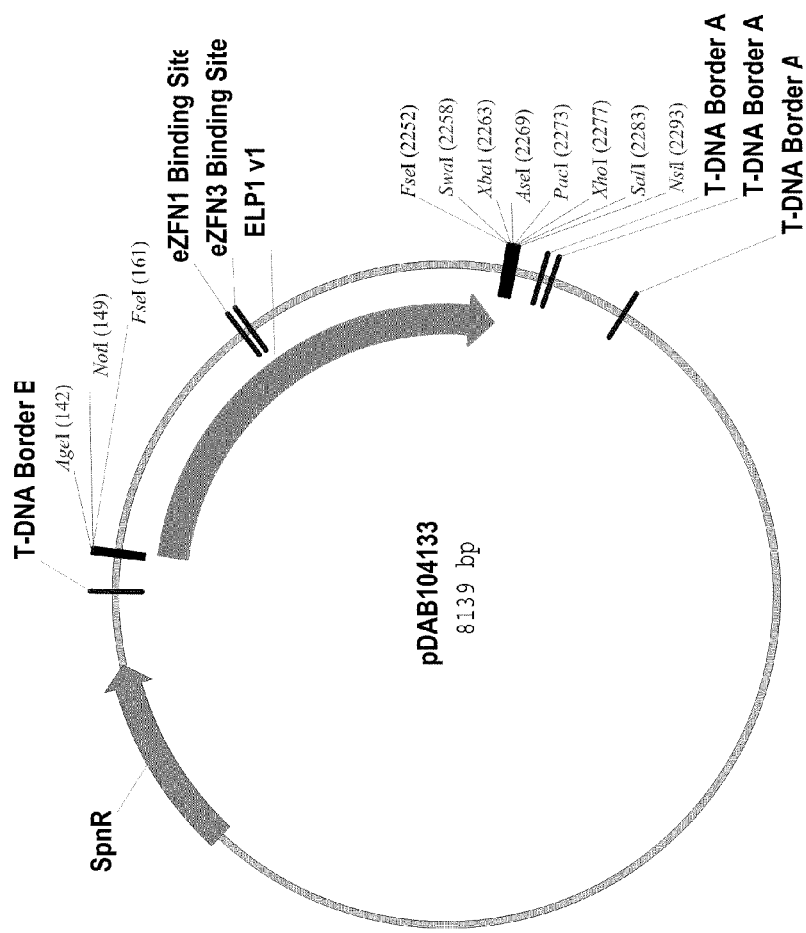
FIG. 17 includes a depiction of a representative vector pDAB104133.
Figure 18:
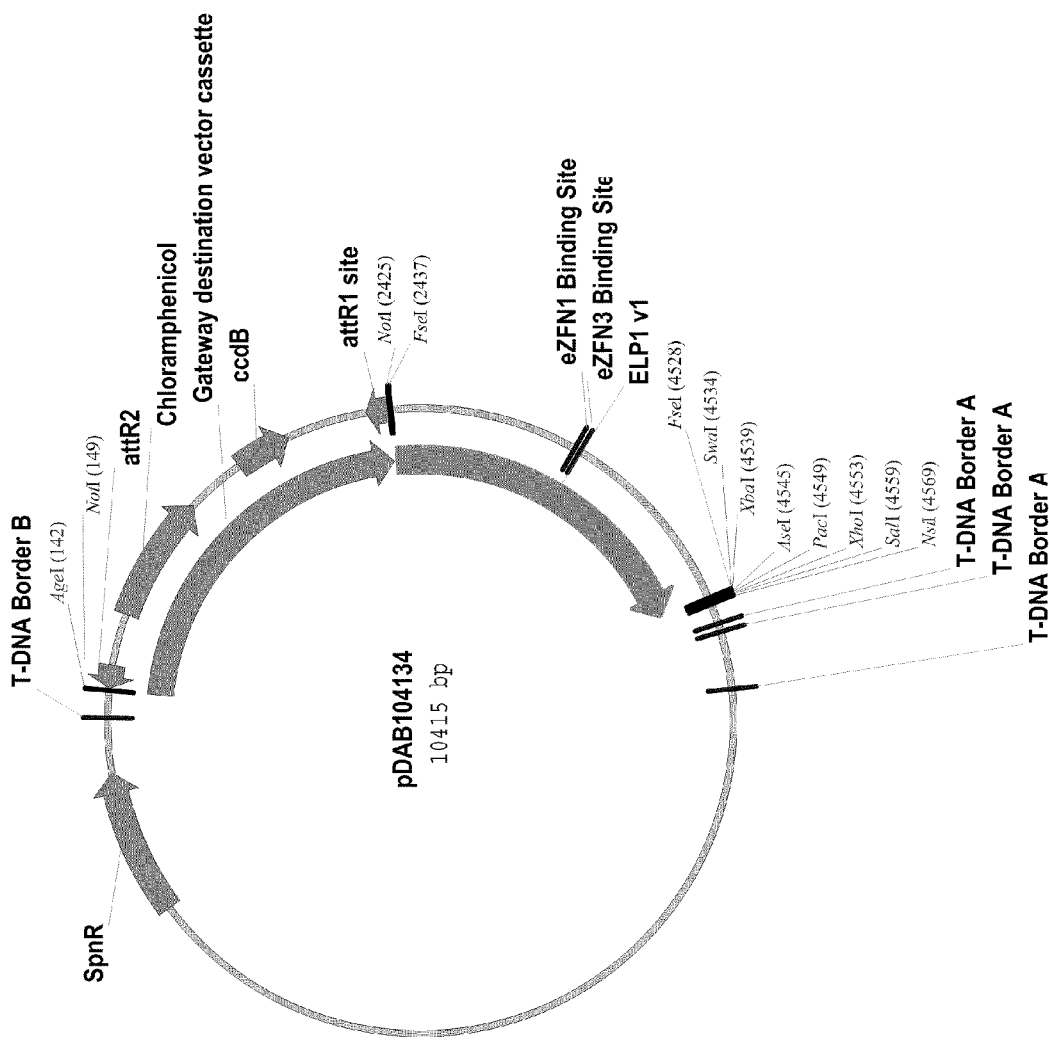
FIG. 18 includes a depiction of a representative vector pDAB104134.
Figure 19:
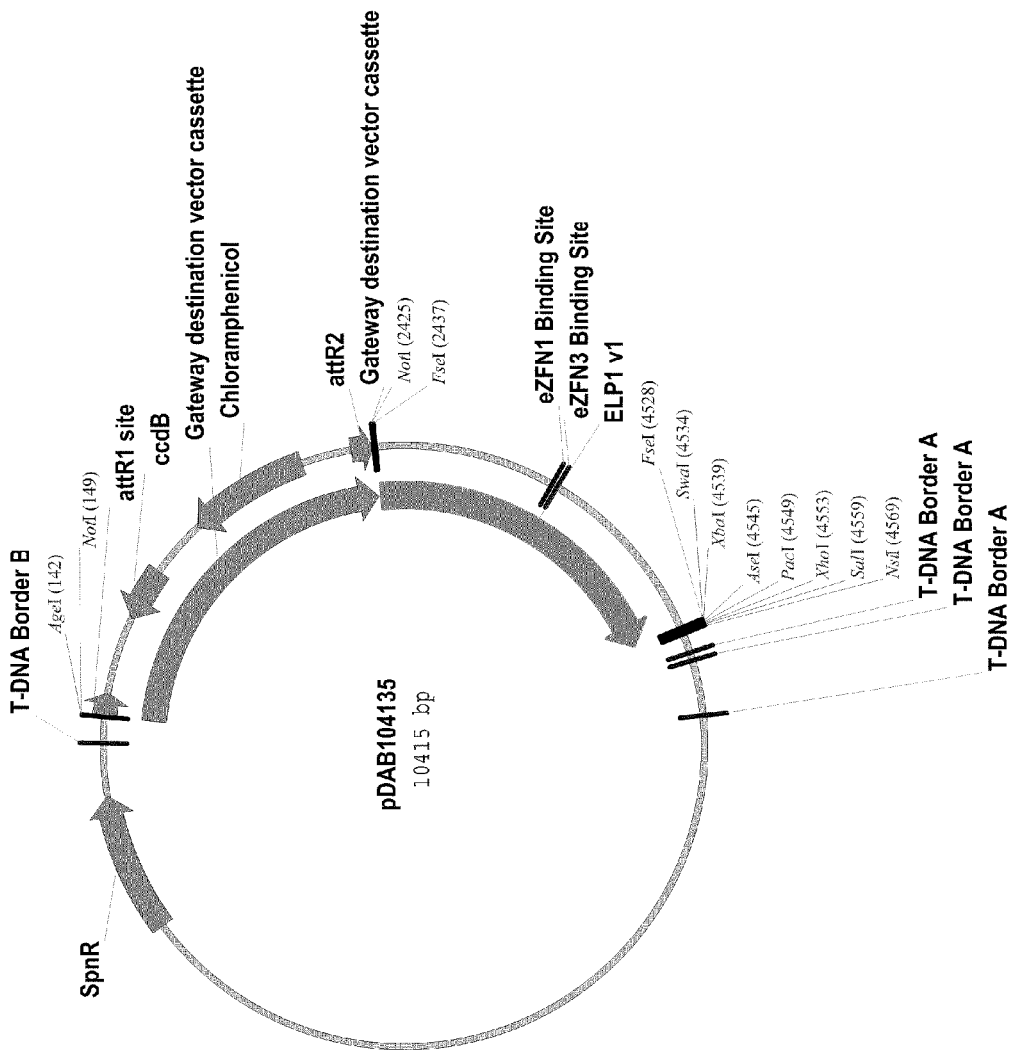
FIG. 19 includes a depiction of a representative vector pDAB104135.

One skilled in the art can assemble the elements described above stepwise in combination to produce primary transformation vectors for use in different crop plants. ELP1 was inserted into the FseI site of pDAB104132 to yield pDAB104133 (FIG. 17). Next, a GATEWAY™ destination vector cassette was inserted into the NotI site of pDAB104133 to yield pDAB104134 (FIG. 18) and pDAB104135 (FIG. 19) which differ only in their orientation of the Gateway cassette relative to the ELP sequence. Then, the four selectable marker ZFN modules described above were cloned into pDAB104135 to yield four novel Plant Transformation Vectors (PTV). This assembly can be accomplished by anyone skilled in the art using standard DNA cloning methods as described below.

Figure 20:
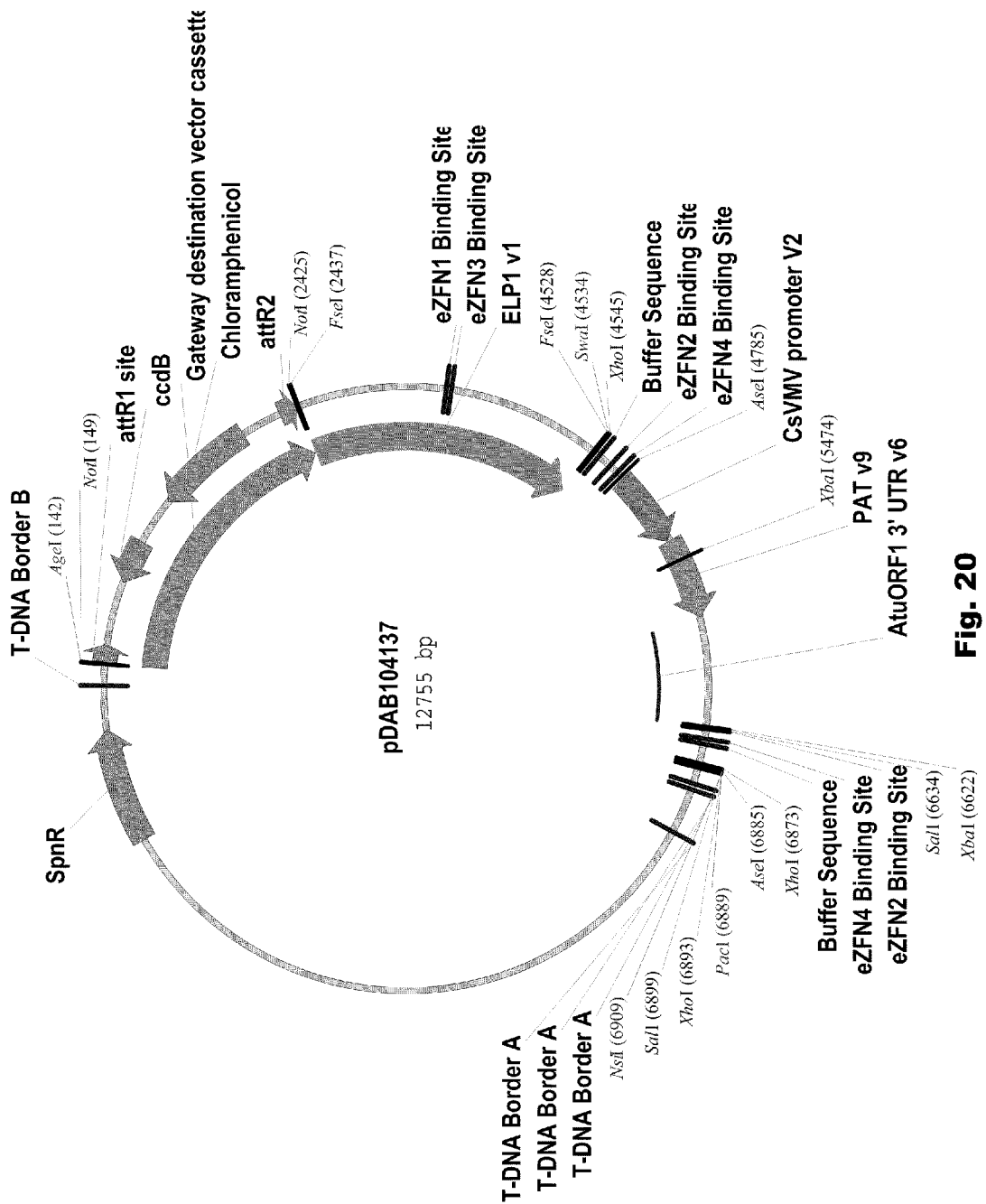
FIG. 20 includes a depiction of a representative vector pDAB104137.

The dicot PAT ZFN module was excised from pDAB104136 using SpeI and cloned into the XbaI site of pDAB104135 to yield PTV pDAB104137 (FIG. 20). pDAB104137 is a binary plant transformation vector carrying ELP1 and a ZFN excisable dicot PAT selectable marker, and is also a GATEWAY™ destination vector that allows for GATEWAY™ cloning of additional transgenes.

Figure 21:
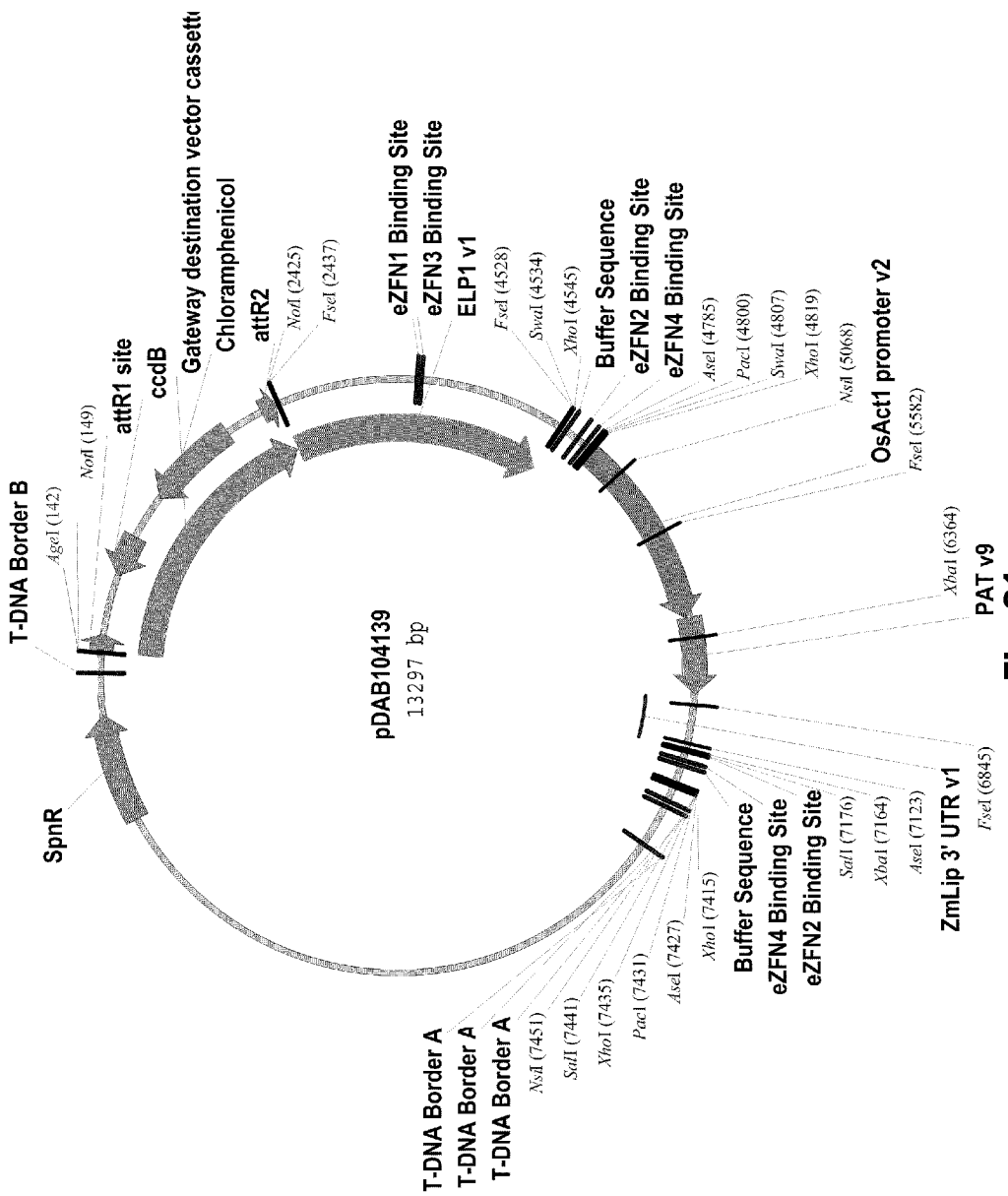
FIG. 21 includes a depiction of a representative vector pDAB104139.

The monocot PAT ZFN module was excised from pDAB104138 using SpeI and cloned into the XbaI site of pDAB104135 to yield PTV pDAB104139 (FIG. 21). pDAB104139 is a binary plant transformation vector carrying ELP1 and a ZFN excisable monocot PAT selectable marker, and is also a GATEWAY™ destination vector.

Figure 22:
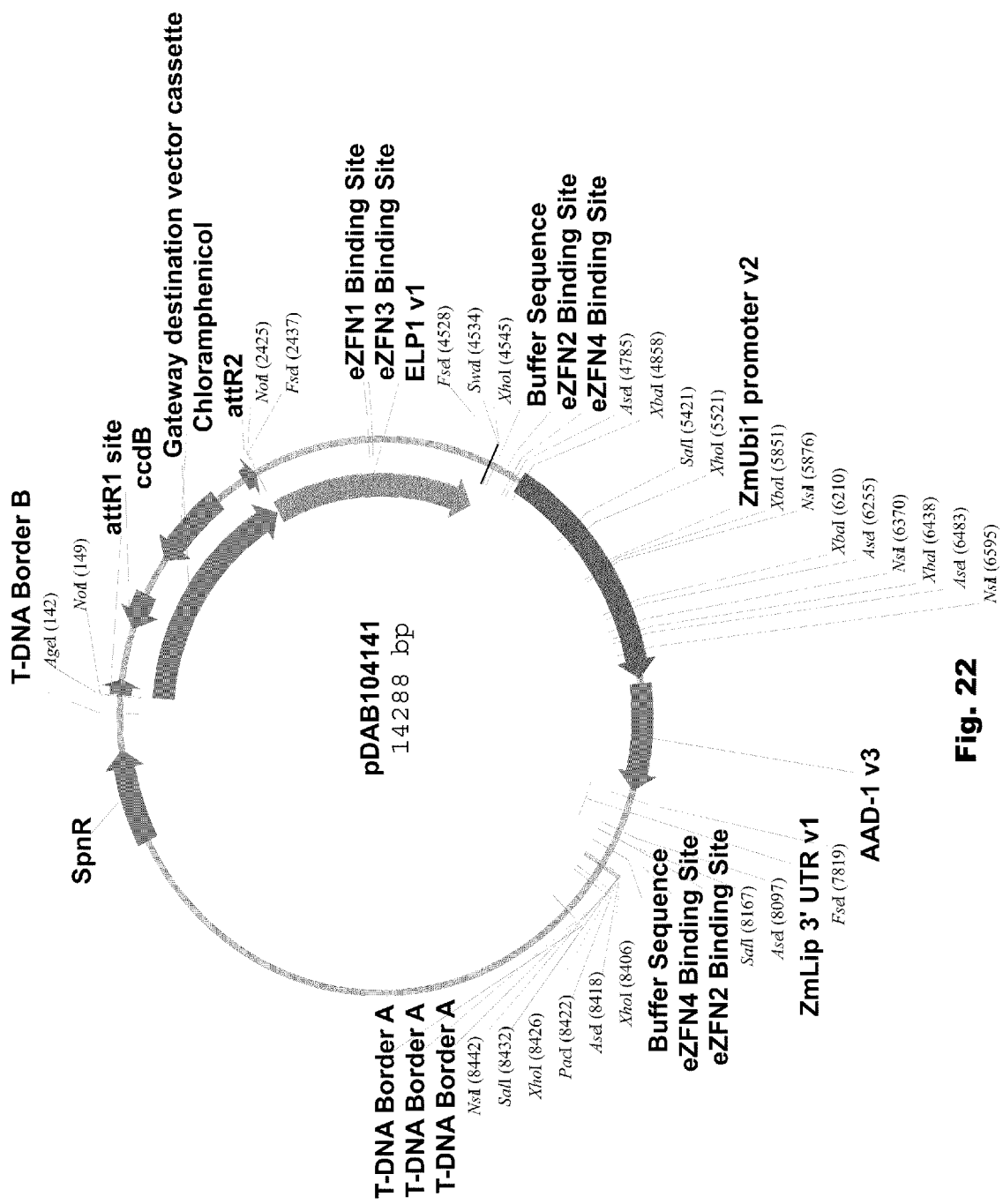
FIG. 22 includes a depiction of a representative vector pDAB104141.
Figure 23:
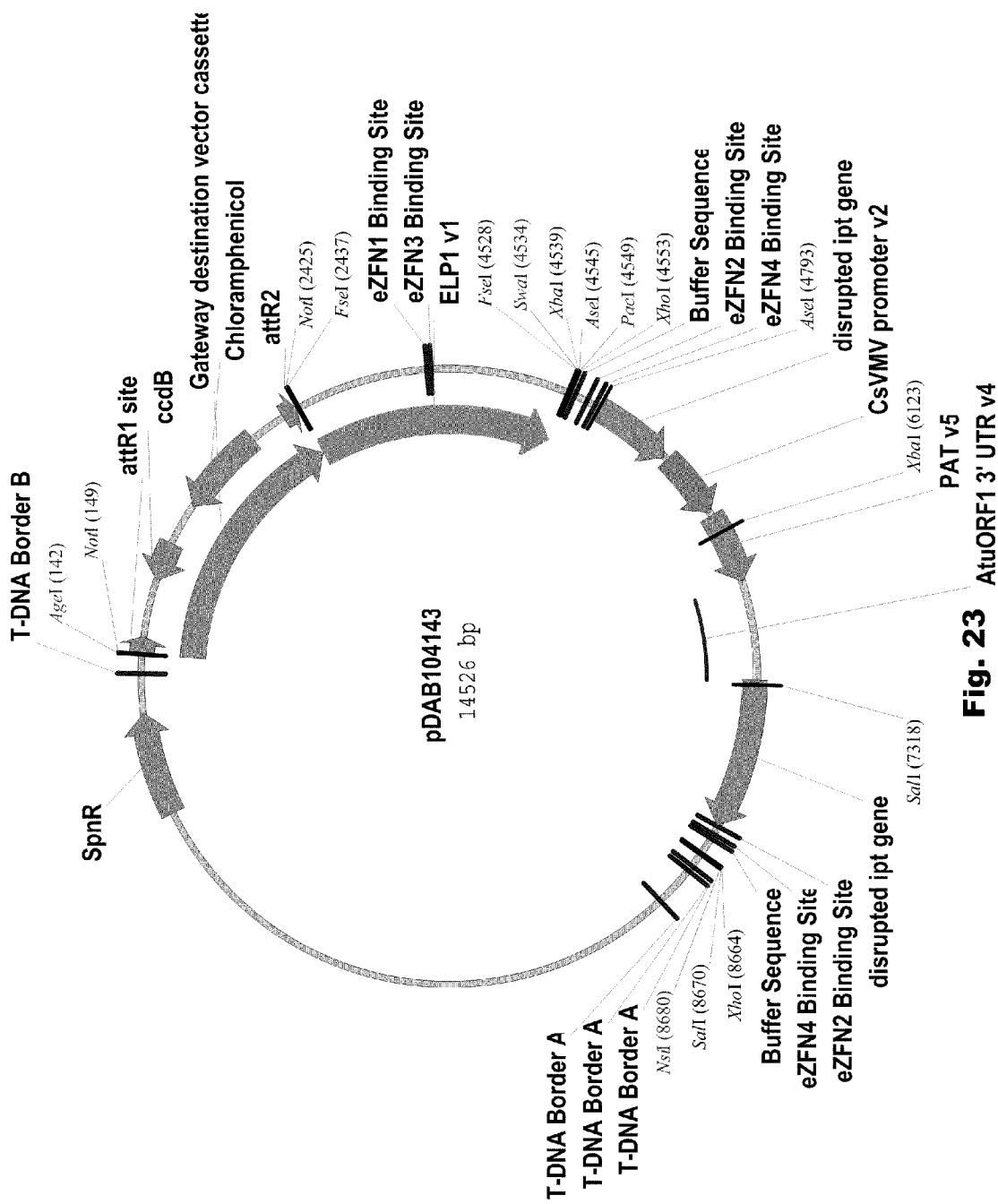
FIG. 23 includes a depiction of a representative vector pDAB104143.

The monocot AAD1 ZFN module was excised from pDAB104140 using SpeI and cloned into the XbaI site of pDAB104135 to yield PTV pDAB104141 (FIG. 22). pDAB104141 is a binary plant transformation vector carrying ELP1 and a ZFN excisable monocot AAD1 selectable marker, and is also a Gateway™ destination vector The canola PAT ZFN module was excised from pDAB104142 using XhoI and cloned into the XhoI site of pDAB104135 to yield PTV pDAB104143 (FIG. 23). pDAB104143 is a binary plant transformation vector carrying ELP1 and a ZFN excisable canola PAT selectable marker, and is also a GATEWAY™ destination vector.

These constructs can be used to transform crop plants using plant transformation methods. The resulting transgenic events can be subsequently targeted with additional new transgenes. Wherein, the new transgene is targeted via homologous recombination to the ELPs. In addition, the selectable marker expression cassette may be removed or excised. The resulting ELP which is produced from the excision of the selectable marker cassette can be subsequently retargeted with a new transgene, via homologous recombination, using the techniques described above.

What is claimed is:

1. A method for producing a transgenic plant cell, the method comprising:
   providing a nucleic acid molecule comprising at least two polynucleotides selected from the group consisting of SEQ ID NOs:1-10, and at least one targeting endonuclease recognition site, wherein the at least two polynucleotides selected from the group consisting of SEQ ID NOs:1-10 flank the at least one targeting endonuclease recognition site; and
   transforming the plant cell with the nucleic acid molecule, wherein the nucleic acid molecule is stably integrated into the genome of the plant cell.

2. The method according to claim 1, wherein the nucleic acid molecule further comprises non-identical restriction sites.

3. The method according to claim 2, wherein the non-identical restriction sites comprise compatible single-stranded ends that allow concatemerization of multiple nucleic acids that each comprise:
   at least two regions of nucleic acid sequence that are not identical to any DNA sequence from the genome of a plant cell, and at least one targeting endonuclease recognition site, wherein the at least two regions of nucleic acid sequence that are not identical to any genomic DNA of the plant cell flank the at least one targeting endonuclease recognition site.

4. The method according to claim 1, wherein the targeting endonuclease is a zinc finger nuclease.

5. The method according to claim 1, wherein the nucleic acid molecule is stably integrated randomly in the genome of the plant cell.

6. The method according to claim 1, wherein the nucleic acid molecule is stably integrated at one or more known target sites in the genome of the plant cell.

7. A transgenic plant cell produced by the method according to claim 1.

8. A method for producing a transgenic plant or plant tissue, the method comprising:

providing a transgenic plant cell having a transgenic nucleic acid molecule stably integrated into the genome of the plant cell, wherein the transgenic nucleic acid molecule comprises:
- at least two polynucleotides selected from the group consisting of SEQ ID NOs:1-10, and at least one targeting endonuclease recognition site, wherein the at least two polynucleotides selected from the group consisting of SEQ ID NOs:1-10 flank the at least one targeting endonuclease recognition site; and regenerating the transgenic plant or plant tissue from the transgenic plant cell.

9. A transgenic plant produced by the method according to claim 8.

10. A seed produced by the transgenic plant of claim 9, wherein the seed comprises the transgenic nucleic acid molecule.

11. A method for producing a transgenic plant cell, the method comprising:
providing a transgenic plant cell having a transgenic nucleic acid molecule stably integrated into the genome of the plant cell, wherein the transgenic nucleic acid molecule comprises:
at least two polynucleotides selected from the group consisting of SEQ ID NOs: 1-10, and at least one targeting endonuclease recognition site, wherein the at least two polynucleotides selected from the group consisting of SEQ ID NOs:1-10 flank the at least one targeting endonuclease recognition site;
providing at least one targeting endonuclease or a first nucleic acid molecule comprising a nucleic acid sequence encoding the at least one targeting endonuclease, wherein the targeting endonuclease(s) recognize targeting endonuclease recognition site(s);
providing a second nucleic acid molecule comprising a nucleic acid sequence of interest and two additional nucleic acid sequences flanking the nucleic acid sequence of interest, wherein each of the two additional nucleic acid sequences is homologous with one of the polynucleotides selected from the group consisting of SEQ ID NOs: 1-10; and
introducing into the plant cell the at least one targeting endonuclease or first nucleic acid molecule, and the second nucleic acid molecule, so as to stably integrate the nucleic acid sequence of interest via homology-driven integration into the genome of the plant cell.

12. A transgenic plant cell produced by the method according to claim 11.

13. A method for producing a transgenic plant or plant tissue, the method comprising:
providing the transgenic plant cell of claim 12; and
regenerating the transgenic plant or plant tissue from the transgenic plant cell.

14. A transgenic plant produced by the method according to claim 13.

15. A seed produced by the transgenic plant of claim 14, wherein the seed comprises the transgenic nucleic acid molecule.

16. The method according to claim 1, wherein the nucleic acid molecule is flanked on each end by one or more additional targeting endonuclease recognition sites.

17. The method according to claim 16, further comprising introducing into the plant tissue or plant one or more targeting endonucleases that recognize the one or more additional targeting endonuclease recognition sites, wherein the nucleic acid molecule is excised from the genome of the plant tissue or plant.

18. The method according to claim 11, wherein the targeting endonuclease is a zinc finger nuclease.

19. A transgenic plant tissue produced by the method according to claim 8.

20. A transgenic plant tissue produced by the method according to claim 13.

* * * * *